(12) United States Patent
Wright et al.

(10) Patent No.: US 7,968,526 B2
(45) Date of Patent: Jun. 28, 2011

(54) ANTISENSE OLIGONUCLEOTIDES DIRECTED TO RIBONUCLEOTIDE REDUCTASE R2 AND USES THEREOF IN THE TREATMENT OF CANCER

(75) Inventors: Jim A. Wright, Oakville (CA); Aiping H. Young, North York (CA)

(73) Assignee: Lorus Therapeutics Inc., Ontario (CA)

( * ) Notice: Subject to any disclaimer, the term of this patent is extended or adjusted under 35 U.S.C. 154(b) by 0 days.

(21) Appl. No.: 12/691,664

(22) Filed: Jan. 21, 2010

(65) Prior Publication Data

US 2010/0197766 A1    Aug. 5, 2010

Related U.S. Application Data

(63) Continuation of application No. 10/545,152, filed as application No. PCT/CA2004/000175 on Feb. 10, 2004, now abandoned.

(60) Provisional application No. 60/448,117, filed on Feb. 20, 2003, provisional application No. 60/320,240, filed on May 31, 2003.

(30) Foreign Application Priority Data

Feb. 10, 2003 (CA) .................................... 2418605

(51) Int. Cl.
*A61K 48/00* (2006.01)
*C07H 21/04* (2006.01)

(52) U.S. Cl. ..... 514/44; 536/23.1; 536/24.3; 536/24.31; 536/24.5

(58) Field of Classification Search .................. None
See application file for complete search history.

(56) References Cited

U.S. PATENT DOCUMENTS

| | | | |
|---|---|---|---|
| 3,687,808 | A | 8/1972 | Merigan et al. |
| 5,834,279 | A | 11/1998 | Rubin et al. |
| 5,998,383 | A | 12/1999 | Wright et al. |
| 6,121,000 | A | 9/2000 | Wright et al. |
| 6,593,305 | B1 * | 7/2003 | Wright ........................ 514/44 A |
| 7,405,205 | B2 | 7/2008 | Wright et al. |
| 2004/0009948 | A1 | 1/2004 | Wright et al. |
| 2007/0274947 | A1 | 11/2007 | Young et al. |
| 2008/0311126 | A1 | 12/2008 | Young et al. |

FOREIGN PATENT DOCUMENTS

| | | |
|---|---|---|
| EP | 0 383 190 A2 | 8/1990 |
| JP | 2000-517167 A | 12/2000 |
| WO | WO 95/02069 A1 | 1/1995 |
| WO | WO 98/00532 | 1/1998 |
| WO | WO 98/05769 A2 | 2/1998 |
| WO | WO 99/02673 A2 | 1/1999 |
| WO | WO 00/47733 A1 | 8/2000 |
| WO | WO 02/085308 A2 | 10/2002 |

OTHER PUBLICATIONS

Agrawal, S. and Kandimalla, E.R, "Antisense and/or Immunostimulatory Oligonucleotide Therapeutics," *Curr. Cancer Drug Targets* 1:197-209, Hybridon, Inc. (2001).

Amara, F.M, et al., "Phorbol Ester Modulation of a Novel Cytoplasmic Protein Binding Activity at the 3'-Untranslated Region of Mammalian Ribonucleotide Reductase R2 mRNA and Role in Message Stability," *J. Biol. Chem.* 269:6709-6715, The American Society for Biochemistry and Molecular Biology, Inc. (1994).

Amara, F.M., et al., "Defining a Novel cis Element in the 3'-Untranslated Region of Mammalian Ribonucleotide Reductase Component R2 mRNA: Role in Transforming Growth Factor-$\beta_1$ Induced mRNA Stabilization," *Nucl. Acids Res.* 23:1461-1467, Oxford University Press (1995) Barker, R.H., et al., "Inhibition of Pasmodium falciparum Malaria using antisense oligodeoxynucleotides," *Proc. Natl. Acad. Sci.* USA 93:514-518, National Academy of Sciences (1996).

Barker, R.H., et al. "Inhibition of *Pasmodium falciparum* Malaria using antisense oligodeoxynucleotides," *Proc. Natl. Acad. Sci. USA* 93:514-518, National Academy of Sciences (1996).

Bitonti, A.J., et al., "Regression of Human Breast Tumor Xenografts in Response to (E)-2'-Deoxy-2'-(fluoromethylene) cytidine, an Inhibitor of Ribonucleoside Diphosphate Reductase," *Cancer Res.* 54(6):1485-1490, Marion Merrell Dow Research Institute (1994).

Björklund, S., et al., "S-Phase-Specific Expression of Mammalian Ribonucleotide Reductase R1 and R2 Subunit mRNAs," *Biochem.* 29:5452-5457, American Chemical Society (1990).

Branch, A., "A Good Antisense Molecule is Hard to Find," *TIBS* 23:45-50, Elsevier Science Ltd. (1998).

Caras, I.W., et al., "Cloned Mouse Ribonucleotide Reductase Subunit M1 cDNA Reveals Amino Acid Sequence Homology with *Escherichia coli* and Herpesevirus Ribonucleotide Reductases," *J Biol. Chem.* 260:7015-7022, The American Society of Biological Chemists, Inc. (1986).

Chakrabarti, D., et al., "Cloning and Characterization of Sununit Genes of Ribonucleotide Reductase, a cell-cycle-regulated enzyme, from *Plasmodium falciparum*," *Proc. Natl. Acad. Sci. USA* 90:12020-12024, National Academy of Sciences (1993).

Chaudhuri, M.M., et al. "cDNA Sequence of the Small Subunit of the Hamster Ribonucleotide Reductase," *Biochimi. et Biophys. Acta* 1171:117-121, Elsevier Science Ltd. (1992).

Chen, F.Y., et al., "Defining a novel ribonucleotide reductase r1 mRNA cis element that binds to an unique cytoplasmic trans-acting protein," *Nucl. Acids Res.* 22:4796-4797, Oxford University Press (1994).

Chen, F.Y., et al., "Mammalian ribonucleotide Reductase R1 mRNA stability under Normal and phorbol ester stimulating conditions: involvement of a cis-trans interaction at the 3' untranslated region," *EMBO J.* 12:3977-3986, Oxford University Press (1993).

Chitambar, C.R. and Wereley, J.P., "Effect of Hydroxyurea on Cellular Iron Metabolism in Human Leukemic CCRF-CEM Cells: Changes in Iron Uptake and the Regulation of Transferrin Receptor and Ferritin Gene Expression following Inhibition of DNA Synthesis," *Cancer Res.* 55:4361-4366, American Association for Cancer Research (1995).

Chiu, C.S.M., et al., "Inhibition of mammalian ribonucleotide reductase by cisdiamminedichloroplatinum(II)," *Biochem. and Cell Biol.* 70:1332-1338, NRC Research Press (1992).

(Continued)

*Primary Examiner* — Amy Bowman
(74) *Attorney, Agent, or Firm* — Sterne, Kessler, Goldstein & Fox PLLC

(57) ABSTRACT

The present invention provides antisense oligonucleotides directed to a mammalian ribonucleotide reductase R2 gene and combinations of the antisense oligonucleotides with one or more chemotherapeutic agents for use in the treatment of cancer.

19 Claims, 42 Drawing Sheets

OTHER PUBLICATIONS

Cory, J.G., et al., "Structural Aspects of N-Hydroxy-N'-Aminoguanidine Derivatives as Inhibitors of L1210 Cell Growth and Ribonucleotide Reductase Activity," *Advan. Enzyme Regul.* 33:129-140, Pergamon Press Ltd. (1993).

Crooke, S.T. ed., "Chapter 1. Basic Principles of Antisense Therapeutics," in: *Antisense Research and Application*, Springer-Verlag, Berlin, DE, pp. 1-50 (1998).

Davis, R., et al., "Purification, Characterization, and Localization of Subunit Interaction Area of Recombinant Mouse Ribonucleotide Reductase R1 Subunit," *J. Biol. Chem.* 269:23171-23176, The American Society for Biochemistry and Molecular Biology, Inc. (1994).

Fabianowska-Majewska, K., et al., "2-Chloro-2'-Deoxyadenosine (2CdA)—Biochemical Aspects of Antileukemic Efficacy," *Acta Pol. Pharm.-Drug Res.* 53:231239, Polish Pharm. Society (1996).

Fan, H., et al., "Ribonucleotide reductase R2 component is a novel malignancy determinant that cooperates with activated oncogenes to determine transformation and malignant potential," *Proc. Natl. Acad. Sci. USA* 93:14036-14040, National Academy of Sciences (1996).

Fan, H., et al., "A link between ferritin gene expression and ribonucleotide reductase R2 protein, as demonstrated by retroviral vector mediated Stable Expression of R2 cDNA," *FEBS Letters* 382:145-148, Elsevier Science Ltd. (1996).

Fan, H., et al., "The R1 component of mammalian ribonucleotide reductase has malignancy-supressing activity as demonstrated by gene transfer experiments," *Proc. Natl. Acad. Sci. USA* 94:13181-13186, National Academy of Sciences (1997).

Gandhi, V., et al., "Chlorodeoxyadenosine and Arabinosylcyosine in Patients with Acute Myelogenous Leukemia: Pharmacokinetic, Pharmacodynamic, and Molecular Interactions," *Blood* 87:256-264, American Society of Hematology (1996).

Giacca, M., et al., "Synergistic Antiviral Action of Ribonucleotide Reductase Inhibitors and 3'-azido-3'-deoxythymidine on HIV Type 1 Infection in Vitro," *Aids Res. Human Retroviruses* 12:677-682, Mary Ann Liebert, Inc. (1996).

Gura, T., "Systems for Identifying New Drugs Are Often Faulty," *Science* 278:1041-1042, American Association for Advancement of Science (1997).

Huang, a., et al., "Ribonucleotide Reductase R2 Gene Expression and Changes in Drug Sensitivity and Genome Stability," *Cancer Res.* 57:4876-4881, American Association for Cancer Research (1997).

Hurta, R.A.R. and Wright, J.A., "Alterations in the Cyclic AMP Signal Transduction Pathway Regulating Ribonucleotide Reductase Gene Expression in Malignant H-ras Transformed Cell Lines," *J. Cell. Physiol.* 158:187-197, Wiley-Liss. Inc. (1994).

Hurta, R.A.R., et al., "Early Induction of Ribonucleotide Reductase Gene Expression by Transforming Growth Factor $\beta_1$ in Malignant H-ras Transformed Cell Lines," *J. Biol. Chem.* 266:24097-24100, The American Society for Biochemistry and Molecular Biology, Inc. (1991).

Jensen, R.A., et al., "Identification of genes expressed in premalignant breast disease by microscopy-directed cloning," *Proc. Natl. Acad. Sci. USA* 91:9257-9261, National Academy of Sciences (1994).

Lee, Y., et al., "GTI-2040, an Antisense Agent Targeting the Small Subunit Component (R2) of Human Ribonucleotide Reductase, Shows Potent Antitumor Activity Against a Variety of Tumors," *Cancer Res.* 63:2802-2811, American Association for Cancer Research (Jun. 2003).

Lepoivre, M., et al., "Alterations of Ribonucloetide Reductase Activity Following Induction of the Nitrite-generating Pathway in Adenocarcinoma Cells," *Biol. Chem.* 265:14143-14149, The American Society for Biochemistry and Molecular Biology, Inc. (1990).

Letsinger, R.L., et al., "Cholesteryl-Conjugated Oligonucleotides: Synthesis, Properties, and Activity as Inhibitors of Replication of Human Immunodeficiency Virus in Cell Culture," *Proc. Natl. Acad. Sci. USA* 86:6553-6556, National Academy of Sciences (1989).

Mader, R.M., et al., "Transcription and Activity of 5-Fluorouracil Converting Enzymes in Fluoropyrimidine Resistance in Colon Cancer in Vitro," *Biochem. Pharmacol.* 54:1233-1242, Elsevier Science Ltd. (1997).

Parker, N. J., et al., "Human M1 Subunit of Ribonucleotide Reductase: cDNA Sequence and Expression in Stimulated Lymphocytes," *Nucl. Acids Res.* 19:3741, Oxford University Press (1991).

Pavloff, N., et al., "Sequence Analysis of the Large and Small Subunits of Human Ribonucleotide Reductase," *J. DNA Sequencing and Mapping* 2:227-234, Harwood Academic Publishers GmbH (1992).

Pearson, W.R., and Lipman, D.J., "Improved Tools for Biological Sequence Comparison," *Proc. Natl. Acad. Sci. USA* 85:2444-2448, National Academy of Sciences (1988).

Piepmeier, J.M., et al., "In Vitro and in Vivo Inhibition of Glioblastoma and Neuroblastoma with MDL101731, A Novel Ribonucleoside Diphosphate Reductase Inhibitor," *Cancer Res.* 56:359-361, American Association for Cancer Research (1996).

Reichard, P., "From RNA to DNA, Why so Many Ribonucleotide Reductases?", *Science* 260:1773-1777, American Association for Advancement of Science (1993).

Rojanasakul, Y., "Antisense Oligonucleotide Therapeutics: Drug Delivery and Targeting," *Adv. Drug Deliv. Rev.* 18:115-131, Elsevier Science Ltd. (1995).

Roy, B., et al., "Inhibition of Ribonucleotide Reductase by Nitric Oxide Derived from Thionitrites: Reversible Modifications of Both Subunits," *Biochem.* 34:5411-5418, American Chemical Society (1995).

Santarossa, S., et al., "Ribonucleotide Reductase Inhibition in the Treatment of Advanced Prostate Cancer: An Experimental Approach with Hydroxyurea and Gallium Nitrate in 20 Patients," *Eur. J. Cancer* 31:1718, Elsevier Science Ltd. (1995).

Slabaugh, M.B., et al., "Vaccinia Virus Ribonucleotide Reductase Expression and Isolation of the Recombinant Large Subunit," *J. Biol. Chem.* 268:17803-17810, The American Society for Biochemistry and Molecular Biology, Inc. (1993).

Standart, N., et al., "Maternal mRNA from Clam Oocytes Can Be Specifically Unmasked in Vitro by Antisense RNA complementary to the 3'-Untranslated Region," *Genes & Development* 4:2157-2168, Cold Spring Harbor Laboratory Press (1990).

Szekeres, T., et al., "Biochemical and Antitumor Activity of Trimidox, a New Inhibitor of Ribonucleotide Reductase," *Cancer Chemother Pharmacol.* 34:63-66, Springer-Verlag (1994).

Thelander, L. and Berg, P., "Isolation and Characterization of Expressible cDNA Clones Encoding the M1 and M2 Subunits of Mouse Ribonucleotide Reductase," *Molec. and Cell. Biol.* 6:3433-3442, American Society for Microbiology (1986).

Thelander, M. and Thelander, L., "Molecular Cloning and Expression of the Functional Gene Encoding the M2 Subunit of Mouse Ribonucleotide Reductase: a New Dominant Marker Gene," *EMBO J.* 8:2475-2479, IRL Press (1989).

Vose, J.M., et al., "Update on Epidemiology and Therapeutics for Non-Hodgkin's Lymphoma," *Hematol.* 2002:241-262, American Society of Hematology (2002).

Wahlestedt, C., et al., "Potent and Nontoxic Antisense Oligonucleotides Containing Locked Nucleic Acids," *Proc. Natl. Acad. Sci. USA* 97:5633-5638, National Academy of Sciences (2000).

Weber, G., "Biochemical Strategy of Cancer Cells and the Design of Chemotherapy: G.H.A. Clowes Memorial Lecture," *Cancer Res.* 43:3466-3492, American Association for Cancer Research (1983).

Weckbecker, G., et al., "Effects of N-Hydroxy-N'-aminoguanidine Derivatives on Ribonucleotide Reductase Activity, Nucleic Acid Synthesis, Clonogenicity, and Cell Cycle of L1210 Cells," *Cancer Res.* 47:975-978, American Association for Cancer Research (1987).

Wright, J.A., et al., "Regulation and Drug Resistance Mechanisms of Mammalian Ribonucleotide Reductase, and the Significance to DNA Synthesis," *Biochem. Cell Biol.* 68:1364-1371, NRC Research Press (1990).

Lorus Therapeutics Inc., "Lorus Therapeutics Signs Agreement to Acquire Genesense Technologies Inc.," *Lorus Therapeutics Inc. Press Release*, 3 pages, Lorus Therapeutics Inc. (1999).

Lorus Therapeutics Inc., "Lorus Therapetuics Files IND Application following positive Preclinical Results of Anti-Cancer Drug GTI 2040," *Lorus Therapeutics Inc. Press Release*, 2 pages, Lorus Therapeutics Inc. (1999).

Lorus Therapeutics Inc., "Lorus Therapeutics Announces Dramatic Anti-Tumor Results for GTI 2040," Lorus Therapeutics Inc. Press Release, 4 pages, Lorus Therapeutics Inc. (1999).

Lorus Therapeutics Inc., "Lorus Therapeutics Reports Results of International Scientific Study," *Lorus Therapeutics Inc.* Press Release, 2 pages, Lorus Therapeutics Inc. (1999).

Lorus Therapeutics Inc., "Lorus Therapeutics Announces FDA Approval to Begin Clinical Trials of Anti-Cancer Drug GTI 2040," *Lorus Therapeutics Inc. Press Release*, 2 pages, Lorus Therapeutics Inc. (1999).

Lorus Therapeutics Inc., "Lorus Therapeutics' Anti-Cancer Drug NC 381 Inhibits the Spread of Human Melanoma Tumor Cells in Mice," *Lorus Therapeutics Inc. Press Release*, 2 pages, Lorus Therapeutics Inc. (2000).

Lorus Therapeutics Inc., "Lorus Announces Intention to Enter Phase II Clinical Trials for GTI-2040 with Strategic Supply Alliance," *Lorus Therapeutics Inc. Press Release*, 2 pages, Lorus Therapeutics Inc. (2000).

Lorus Therapeutics Inc., "Lorus Therapeutics Presents Anticancer Drug GTI-2040 At International Oncology Meeting in Greece," *Lorus Therapeutics Inc. Press Release*, 2 pages, Lorus Therapeutics Inc. (2000).

Lorus Therapeutics Inc., "Progress in Lorus Therapeutics' GTI-2040 Phase I/II Clinical Trial," *Lorus Therapeutics Inc.* Press Release, 2 pages, Lorus Therapeutics Inc. (2000).

Lorus Therapeutics Inc., "Lorus Therapeutics' Lead Anti-Cancer Drugs Reduce Tumor Growth in Mouse Models with Human Prostate Cancer Cells," *Lorus Therapeutics Inc. Press Release*, 2 pages, Lorus Therapeutics Inc. (2000).

Lorus Therapeutics Inc., "Findings on Lorus Therapeutics' Lead Anti-Cancer Drug Presented at Annual Meeting of American Association for Cancer Research," *Lorus Therapeutics Inc. Press Release*, 2 pages, Lorus Therapeutics Inc. (2000).

Lorus Therapeutics Inc., "Lorus Therapeutics Receives Issued United States Patent for Invention of Key Anti-Cancer Drugs," *Lorus Therapeutics Inc. Press Release*, 2 pages, Lorus Therapeutics Inc. (2000).

Lorus Therapeutics Inc., "Lorus Therapeutics Reports First Quarter Results," *First Quarter Report*, 3 pages, Lorus Therapeutics Inc. (2001).

Lorus Therapeutics Inc., "Lorus Therapeutics to Present Three Anti-Cancer Drugs at Annual meeting of The American Association for Cancer Research," *Lorus Therapeutics Inc. Press Release*, 2 pages, Lorus Therapeutics Inc. (2001).

Lorus Therapeutics Inc., "Lorus Therapeutics to Present Research of Lead Antisense Drug at Industry Conference," *Lorus Therapeutics Inc. Press Release*, 2 pages, Lorus Therapeutics Inc. (2001).

Lorus Therapeutics Inc., "Lorus Therapeutics's GTI-2040 Prolongs Survival Rates of Mice Models with Lymphoma in Pre-Clinical Testing," *Lorus Therapeutics Inc. Press Release*, 2 pages, Lorus Therapeutics Inc. (2001).

Lorus Therapeutics Inc., "Lorus Therapeutics Inc. Announces Two New Members to its Board of Directors," *Lorus Therapeutics Inc. Press Release*, 2 pages, Lorus Therapeutics Inc. (2001).

Lorus Therapeutics Inc., "Lorus Therapeutics Inc. to Present Clinical Results for Lead Antisense Anti-Cancer Drug at ASCO," *Lorus Therapeutics Inc. Press Release*, 2 pages, Lorus Therapeutics Inc. (2001).

Lorus Therapeutics Inc., "Lorus Advances Its Antisense Clinical Program for Renal Cell Carcinoma," *Lorus Therapeutics Inc. Press Release*, 2 pages, Lorus Therapeutics Inc. (2001).

Lorus Therapeutics Inc., "Lorus Therapeutics Reports Year-End Results," *Fourth Quarter Report*, 2 pages, Lorus Therapeutics Inc. (2001).

Lorus Therapeutics Inc., "Lorus Therapeutics Reports Year-End Results," *Fourth Quarter Report*, 3 pages, Lorus Therapeutics Inc. (2001).

Lorus Therapeutics Inc., "Lorus Therapeutics and U.S. National Cancer Institute to Collaborate on the Conduct of Mulitple Phase II Clinical Trials with Lorus' GTI-2040," *Lorus Therapeutics Inc. Press Release*, 2 pages, Lorus Therapeutics Inc. (Jun. 2002).

Lorus Therapeutics Inc., "Lorus Therapeutics Reports First Quarter Results," *First Quarter Report*, 3 pages, Lorus Therapeutics Inc. (Oct. 2002).

Lorus Therapeutics Inc., "Scientific Publication Describes Oncogene Interaction with Lorus Anticancer Target," *Lorus Therapeutics Inc. Press Release*, 2 pages, Lorus Therapeutics Inc. (Feb. 2002).

Lorus Therapeutics Inc., "Lorus Therapeutics Reports Second Quarter Results," *Second Quarter Report*, 3 pages, Lorus Therapeutics Inc. (Jan. 2003).

Lorus Therapeutics Inc., "Lorus Announces Expansion of Renal Cell Carcinoma Clinical Trial to Major Oncology Centers in the United States," *Lorus Therapeutics Inc. Press Release*, 2 pages, Lorus Therapeutics Inc. (Feb. 2003).

Lorus Therapeutics Inc., "Lorus Therapeutics Allowed United States Patent to Protect Key Antisense Anticancer Target," *Lorus Therapeutics Inc. Press Release*, 2 pages, Lorus Therapeutics Inc. (Mar. 2003).

Office Action for U.S. Patent No. 5,998,383, Wright, J.A., issued Dec. 7, 1999, mailed Mar. 17, 1998.

Office Action for U.S. Patent No. 5,988,383, Wright, J.A., issued Dec. 7, 1999, mailed Aug. 17, 1998.

Office Action for U.S. Appl. No. 10/447,136, Wright, et al., filed May 29, 2003, mailed Jul. 9, 2007.

Office Action for U.S. Appl. No. 10/447,136, Wright, et al., filed May 29, 2003, mailed Mar. 28, 2006.

Office Action for U.S. Appl. No. 10/447,136, Wright, et al., filed May 29, 2003, mailed Sep. 11, 2006.

Office Action for U.S. Appl. No. 10/447,136, Wright, J.A., filed May 29, 2003, mailed Jan. 5, 2007.

Bitonti, A.J., et al., "Response of Human Colon and Prostate Tumor Xenografts to (E)-2'-Deoxy-2'-(Fluoromethylene)Cytidine, an Inhibitor of Ribonucleotide Reductase," *Anticancer Research* 15:1179-1182, International Institute of Anticancer Research (1995).

Hurta, R.A.R. and Wright, J.A., "Malignant Transformation by H-*ras* Results in Aberrant Regulation of Ribonucleotide Reductase Gene Expression by Transforming Growth Factor-β," *J. Cell. Biology* 57:543-556, Wiley-Liss, Inc. (1995).

Klisovic, R.B., et al., "Phase I Study of GTI-2040, an Antisense to Ribonucleotide Reductase, in Combination with High-Dose Cytarabine in Patients with Acute Myeloid Leukemia," *Clin. Cancer Res.* 14:3889-3895, American Association for Cancer Research (2008).

Morgan, S.E. and Kastan, M.B., "Foundations in Cancer Research p53 and ATM: Cell Cycle, Cell Death, and Cancer," *Advances in Cancer Research* 71:1-25, Academic Press (1997).

Pötsch, S., et al., "p-Alkoxyphenols, a New Class of Inhibitors of Mammalian R2 Ribonucleotide Reductase: Possible Candidates for Antimelanotic Drugs," *Molecular Pharmacology* 45:792-796, American Society for Pharmacology and Experimental Therapeutics (1994).

Saeki, T., et al., "Immunohistochemical detection of ribonucleotide reductase in human breast tumors," *International Journal of Oncology* 6:523-529, Spandidos Publications Ltd. (1995).

Standart, N. and Hunt, T., "Control of Translation of Masked mRNAs in Clam Oocytes," *Enzyme* 44:106-119, Karger AG Basel (1990).

Stull, R.A. and Szoka, Jr., F.C., "Antigene, Ribozyme and Aptamer Nucleic Acid Drugs: Progress and Prospectes," *Pharmaceutical Research* 12:465-483, Plenum Publishing Corp. (1995).

Takeda, E. and Weber, G., "Role of Ribonucleotide Reductase in Expression of the Neoplastic Program," *Life Sciences* 28:1007-1014, Pergamon Press Ltd. (1981).

Wright, J., "Altered Mammalian Ribonucleoside Diphosphate Reductase from Mutant Cell Lines," *Int. Encyclop. Pharmacol. Therapeut.* 128:89-111, Elsevier (1989).

Office Action mailed Oct. 14, 1999 in U.S. Appl. No. 09/249,247 to Wright, J.A., filed Feb. 11, 1999.

Office Action mailed Jul. 6, 2000 in U.S. Appl. No. 09/249,247 to Wright, J.A., filed Feb. 11, 1999.

Office Action mailed Mar. 27, 2001 in U.S. Appl. No. 09/249,247 to Wright, J.A., filed Feb. 11, 1999.

Office Action mailed Jun. 5, 2002 in U.S. Appl. No. 09/249,247 to Wright, J.A., filed Feb. 11, 1999.

Office Action mailed Nov. 13, 2007 in U.S. Appl. No. 10/557,853, Young, A.H., et al., filed Jan. 29, 2007.

Office Action mailed Apr. 14, 2008 in U.S. Appl. No. 10/557,853, Young, A.H., et al., filed Jan. 29, 2007.

Agrawal, S., "Antisense oligonucleotides: towards clinical trials," *Trends Biotechnol.* 14:376-87, Elsevier Science Ltd., England (1996).

Calabretta, B., et al., "Antisense strategies in the treatment of leukemias," *Semin. Oncol.* 23:78-87, W.B. Saunders Company, United States (1996).

Choy, B.K., et al., "Molecular mechanisms of drug resistance involving ribonucleotide reductase: hydroxyurea resistance in a series of clonally related mouse cell lines selected in the presence of increasing drug concentrations," *Cancer Res.* 48:2029-35, American Association for Cancer Research, United States (1988).

Crooke, S.T., "Progress in antisense therapeutics," *Hematol. Pathol.* 9:59-72, Marcel Dekker, Inc., United States (1995).

Dorigo, O., et al., "Combination of transforming growth factor β antisense and interleukin-2 gene therapy in the murine ovarian teratoma model," *Gynecol. Oncol.* 71:204-10, Academic Press, United States (1998).

Elford, H.L., et al., "New ribonucleotide reductase inhibitors with antineoplastic activity," *Cancer Res.* 39:844-51, American Association for Cancer Research, United States (1979).

Gewirtz, A.M., "Oligodeoxynucleotide-based therapeutics for human leukemias," *Stem Cells* 11(Suppl 3):96-103, AlphaMed Press, United States (1993).

Gewirtz, A.M., et al., "Facilitating oligonucleotide delivery: helping antisense deliver on its promise," *Proc. Natl. Acad. Sci. U.S.A.* 93:3161-63, National Academy of Sciences, United States (1996).

Hanania, E.G., et al., "Recent advances in the application of gene therapy to human disease," *Am. J. Med.* 99:537-52, Donnelly, United States (1995).

Hatanaka, K., et al., "Interferon-⊕ and antisense K-*ras* RNA combination gene therapy against pancreatic cancer," *J. Gene. Med.* 6:1139-48, John Wiley & Sons, Ltd., United States (2004).

Lefebvre d'Hellencourt, C., et al., "Immunomodulation by cytokine antisense oligonucleotides," *Eur. Cytokine Netw.* 6:7-19, John Libbey Eurotext Ltd., France (1995).

Lin, Z.P., et al., "Stable suppression of the R2 subunit of ribonucleotide reductase by R2-targeted short interference RNA sensitizes p53(-/-) HCT-116 colon cancer cells to DNA-damaging agents and ribonucleotide reductase inhibitors," *J. Biol. Chem.* 279:27030-38, The American Society for Biochemistry and Molecular Biology, Inc., United States (2004).

Marcucci, G., et al., "Phase 1 and pharmacodynamic studies of G3139, a Bcl-2 antisense oligonucleotide, in combination with chemotherapy in refractory or relapsed acute leukemia," *Blood* 101:425-32, The American Society of Hematology, United States (2003).

Nandy, P., et al., "Inhibition of ribonucleotide reductase by a new class of isoindole derivatives: drug synergism with cytarabine (Ara-C) and induction of cellular apoptosis," *Anticancer Res.* 19:1625-33, J.G. Delinassios, Anticancer Research, Greece (1999).

Orr, R.M., "Technology evaluation: leukemia therapy, University of Pennsylvania," *Curr. Opin. Mol. Ther.* 1:399-403, Current Drugs Ltd., England (1999).

Pavlick, A.C., et al., "Novel therapeutic agents under investigation for malignant melanoma," *Expert Opin. Investig. Drugs.* 12:1545-58, Ashley Publications Ltd., England (2003).

Salom, E., et al., "Management of recurrent ovarian cancer: evidence-based decisions," *Curr. Opin. Oncol.* 14:519-27, Lippincott Williams & Wilkins, Inc., United States (2002).

Scanlon, K.J., et al., "Oligonucleotide-mediated modulation of mammalian gene expression," *FASEB J.* 9:1288-96, The Federation of American Societies for Experimental Biology, United States (1995).

Wagner, R.W., "Gene inhibition using antisense oligodeoxynucleotides," *Nature* 372:333-35, Nature Publishing Group, England (1994).

Wright, J.A., and Anazodo, M., "Antisense molecules and their potential for the treatment of cancer and Aids," *The Cancer Journal* 8: 185-189, Lippincott Williams & Wilkins, Inc., United States (1995).

Wright, J.A., et al., "Hydoxyurea and related compounds," in *Drug Resistance in Mammalian Cells*: Antimetabolites and Cytotoxic Analogs, vol. 1, pp. 15-27, Gupta, R.S., ed., CRC Press, United States (1989).

International Search Report for International Patent Application No. PCT/CA2004/000175, European Patent Office, Rijswijk, Netherlands, mailed on Jul. 5, 2004.

International Search Report for International Patent Application No. PCT/CA2005/000040, Canadian Intellectual Property Office, Quebec, Canada, mailed on Jun. 7, 2005.

Notice of Allowance dated Feb. 18, 1999, issued in U.S. Appl. No. 08/904,901, to Wright et al., filed on Aug. 1, 1997.

Notice of Allowance dated Feb. 6, 2008, issued in U.S. Appl. No. 10/447,136, to Wright of al., filed on May 29, 2003.

Office Action mailed Nov. 13, 2007, in the U.S. Appl. No. 10/545,152, Wright et al., filed on Aug. 10, 2005.

Office Action mailed May 15, 2008, in the U.S. Appl. No. 10/545,152, Wright of al., filed on Aug. 10, 2005.

Office Action mailed Feb. 20, 2009, in the U.S. Appl. No. 10/545,152, Wright et al., filed on Aug. 10, 2005.

Office Action mailed Sep. 21, 2009, in the U.S. Appl. No. 10/545,152, Wright et al., filed on Aug. 10, 2005.

Office Action mailed Dec. 4, 2008, in the U.S. Appl. No. 10/585,772, Young et al., filed on Nov. 13, 2007.

Office Action mailed Apr. 2, 2009, in the U.S. Appl. No. 10/585,772, Young et al., filed on Nov. 13, 2007.

Office Action mailed Nov. 5, 2009, in the U.S. Appl. No. 10/585,772, Young et al., filed on Nov. 13, 2007.

Office Action mailed Aug. 30, 2010, in the U.S. Appl. No. 10/585,772, Young et al., filed on Nov. 13, 2007.

NCBI Entrez, GenBank Report, Accession No. AY032750, Zhou, B. and Yen, Y., Entry Date Apr. 2001.

NCBI Entrez, GenBank Report, Accession No. BC001886, Strausberg, R.L. et al., Entry Date Jan. 2001.

NCBI Entrez, GenBank Report, Accession No. NM_001033, Brissenden, J.E. et al., Entry Date Jan. 1988.

NCBI Entrez, GenBank Report, Accession No. NM_001034, Yang-Feng, T.L. et al., Entry Date Sep. 1987.

NCBI Entrez, GenBank Report, Accession No. NM_009103, Caras, I.W. et al., Entry Date Jun. 1985.

NCBI Entrez, GenBank Report, Accession No. NM_009104, Thelander, L. and Berg, P., Entry Date Oct. 1986.

NCBI Entrez, GenBank Report, Accession No. X68127 S49271, Srinivasan, P., Entry Date Aug. 1992.

* cited by examiner

Weight of Human Colon Adenocarcinoma (HT-29) in CD-1 Nude Mice Treated with Combination Therapy Pre-clinical Efficacy in
Combination Therapy: Kidney Tumors (Caki-1)

A

B

Weight of Human Prostate Carcinoma (PC-3) in SCID Mice

Weight of Human Prostate Carcinoma(DU145) in SCID Mice

A

Growth of Human Pancreatic Carcinoma (BxPC-3) in CD-1 Nude Mice

B

Weight of Human Pancreatic Carcinoma (BxPC-3) in CD-1 Nude Mice

Statistical Analysis:   P value

Saline: Gemcitabine 0.3965
Saline: SEQ ID NO:1 <0.0001

Growth Of Human Breast Cancer (MDA-CDDP-S4) In CB-17
SCID Mice Treated With Taxol, SEQ ID NO:1, and Taxol+ SEQ ID NO:1
(Orthotopical transplant)

B

SEQ ID NO:1: Taxol P=0.0133
SEQ ID NO:1: SEQ ID NO:1+Taxol P=0.0003
Taxol: SEQ ID NO:1+Taxol P<0.0001

C

Weight of Human Taxol-Resistant Breast Adenocarcinoma
(MDA-MB435-To.1) Implanted at the Fat Pad of SCID Mice Tumor Weight (mg)

Growth of Human Breast Adenocarcinoma (MDA-MB435-To. 1) in SCID Mice

A

Weight of Human Breast Adenocarcinoma (MDA-MB-435-To. 1) in SCID Mice

B

A

Growth of Promyelocytic Leukemia HL-60
(Taxol-Resistant) in SCID Mice

B

Weight of Human Promyelocytic Leukemia HL-60
(Taxol-Resistant) in SCID Mice

Growth of Human Multi-Drug Resistance Colon
Adenocarcinoma (LS513) in SCID Mice

A

B

C  Weight of Human Colon Multi-Drug Resistance Carcinoma (LS513) in SCID Mice

A. Growth of Human Colon Adenocarcinoma (HT-29) in CD-1 Nude Mice

B. Tumor Weight of Human Colon Adenocarcinoma (HT-29) in CD-1 Nude Mice

* Significant difference compared to control
T= SEQ ID NO:1 treatment with 0.4, 1.0, 2.0, 4.0 or 6.0 mg/kg A    Growth of Human Melanoma (A2058) in CD-1 Nude Mice 18 (Continued)
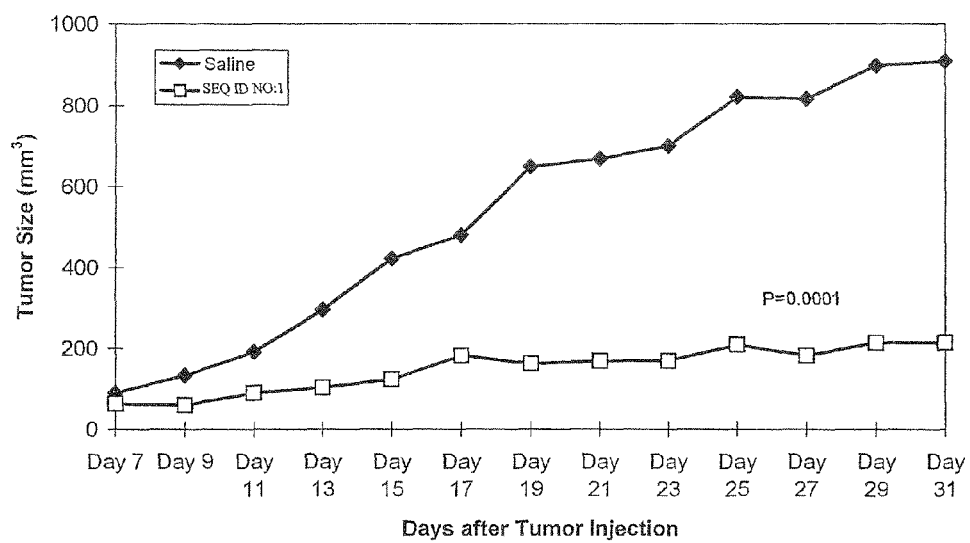
B  Growth of Human Breast Adenocarcinoma (MDA-MB-231) in CD-1 Nude Mice 18 (Continued)
C
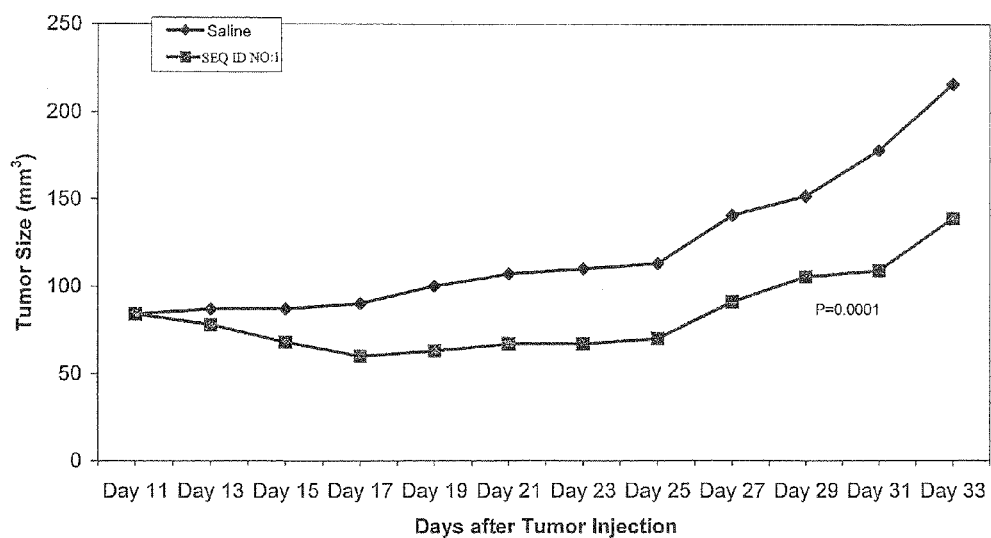
Growth of Human Ovary Adenocarcinoma (SK-OV-3) in Balb/c Nude Mice

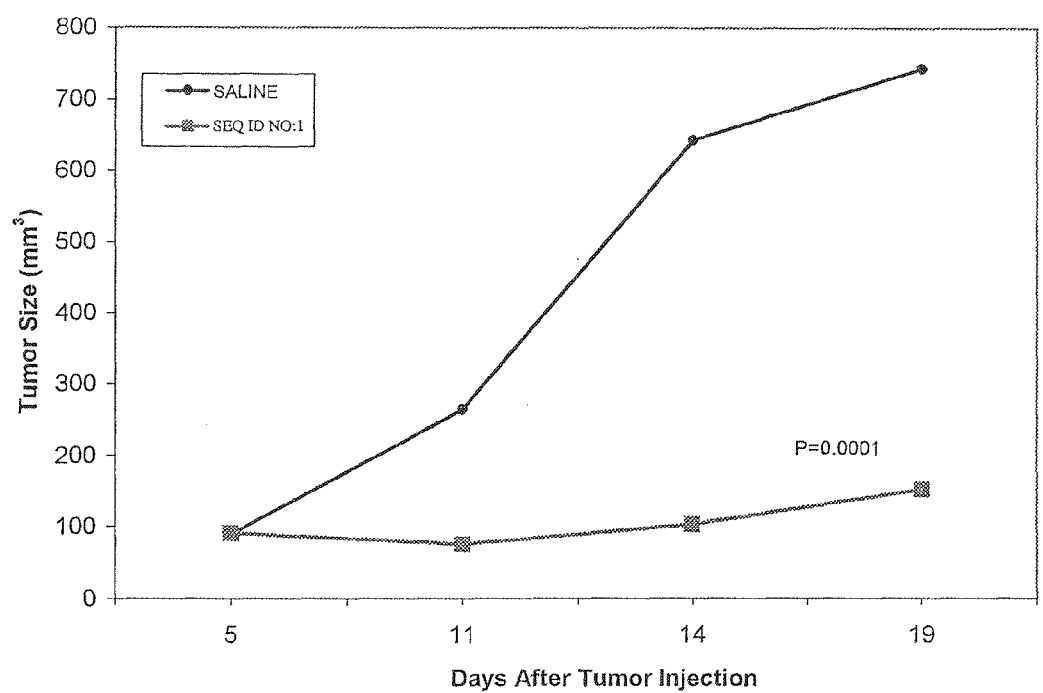
18 (Continued)
D  Growth of Human Lung Carcinoma (NCI-H460) in CD-1 Nude Mice Growth of Human Pancreatic Carcinoma (SU.86.86) in CD-1 Nude Mice Growth of Human Hepatocellular Carcinoma (HepG2) in CD-1 Nude Mice A Growth of Human Cervical Carcinoma (SIHA) in SCID Mice B Weight of Human Cervical Carcinoma (SIHA) in SCID Mice A  Growth of Human Cervix Epitheloid Carcinoma (Hela S3) in SCID Mice B  Weight of Human Cervix Epitheloid Carcinoma (Hela S3) in SCID mice A
Survival Time of SCID Mice Bearing Lymphoma (Raji)

B
Survival Time of SCID Mice Bearing Human Lymphoma (Raji)

Survival Time of CB-17 SCID Mice Bearing Erythroleukemia (CB7)

Days After I.V. Injection of Leukemia Cells Through Tail Vein

A

B 28 (Continued)
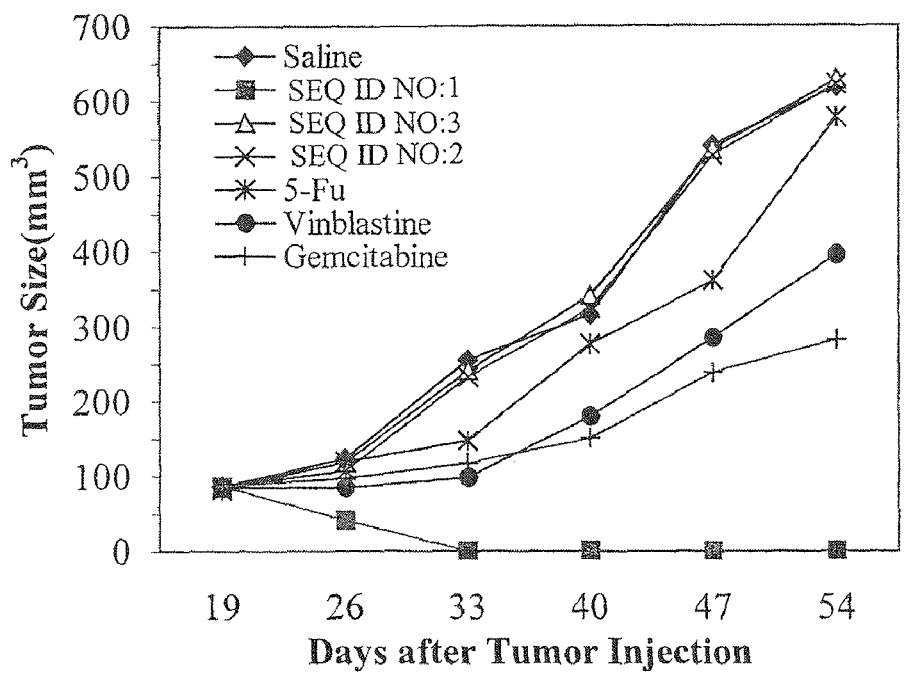
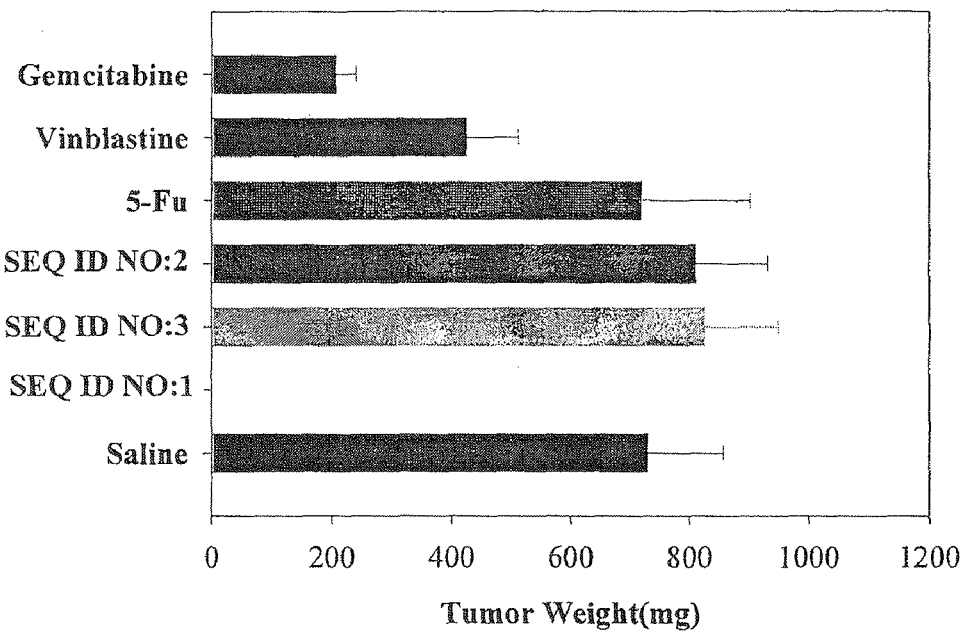

Days After I.V. Injection of Lymphoma Cell Line

SEQ ID NO:1 efficacy: growth of human tumor xenografts (Caki-1) in SCID/beige mice

A

B

A

SEQ ID NO:1 AUC vs Actual Dose

B

```
                              SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 1
ggctaaatcg ctccaccaag                                                  20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 2
ggctaaactc gtccaccaag                                                  20

<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 3
acgcactcag ctagtgacac                                                  20

<210> SEQ ID NO 4
<211> LENGTH: 20
<212> TYPE: DNA
<213> ORGANISM: Artificial Sequence
<220> FEATURE:
<223> OTHER INFORMATION: antisense oligonucleotide
<221> NAME/KEY: misc_feature
<222> LOCATION: (9)...(9)
<223> OTHER INFORMATION: "c" is methylated

<400> SEQUENCE: 4
ggctaaatcg ctccaccaag                                                  20

<210> SEQ ID NO 5
<211> LENGTH: 20
<212> TYPE: DNA
<213> ORGANISM: Artificial Sequence
<220> FEATURE:
<223> OTHER INFORMATION: antisense oligonucleotide
<221> NAME/KEY: misc_feature
<222> LOCATION: (11)...(11)
<223> OTHER INFORMATION: "c" is methylated

<400> SEQUENCE: 5
ggctaaatcg ctccaccaag                                                  20
```

ANTISENSE OLIGONUCLEOTIDES DIRECTED TO RIBONUCLEOTIDE REDUCTASE R2 AND USES THEREOF IN THE TREATMENT OF CANCER

FIELD OF THE INVENTION

The present invention pertains to the field of cancer therapeutics and in particular to the use of antisense oligonucleotides alone or in combination with one or more chemotherapeutic drugs for the treatment of cancer.

BACKGROUND

Regulation of ribonucleotide reductase, and particularly the R2 component, is altered in malignant cells exposed to some tumour promoters and to the growth factor TGF-β [Amara, et al., 1994; Chen et al., 1993; Amara et al., 1995b; Hurta and Wright, 1995; Hurta et al., 1991]. Higher levels of enzyme activity have been observed in cultured malignant cells when compared to nonmalignant cells [Weber, 1983; Takeda and Weber, 1981; Wright et al., 1989a], and increased levels of R2 protein and R2 mRNA have been found in premalignant and malignant tissues as compared to normal control tissue samples [Saeki et al., 1995; Jensen et al., 1994]. However, these correlative studies did not show a direct role for ribonucleotide reductase in cancer cell transformation and tumour progression, because like so many other enzyme activities found to be altered in cancer cells [e.g. Weber, 1983], the results could easily be explained by the increased cell proliferation and altered cell cycle regulation characteristics of transformed and malignant cell populations [Morgan and Kastan, 1997].

Antisense oligonucleotides directed to the R1 or R2 component of ribonucleotide reductase have been shown to be effective in reducing the growth of cancer cells [see, for example, U.S. Pat. Nos. 5,998,383 and 6,121,000].

In view of the high incidence of various types of cancer throughout the world, there remains a need for improved therapies for the treatment of cancer.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide antisense oligonucleotides directed to ribonucleotide reductase R2 and uses thereof in the treatment of cancer. In accordance with an aspect of the present invention, there is provided an antisense oligonucleotide of between 7 and 100 nucleotides in length comprising at least 7 consecutive nucleotides from SEQ ID NO:1 for use in the treatment of cancer in a mammal in need of such therapy.

In accordance with another aspect of the present invention, there is provided an antisense oligonucleotide of between 7 and 100 nucleotides in length comprising at least 7 consecutive nucleotides from SEQ ID NO:1 for use in combination with one or more chemotherapeutic agents in the treatment of cancer in a mammal in need of such therapy.

In accordance with another aspect of the present invention, there is provided an antisense oligonucleotide of between 20 and 100 nucleotides in length comprising the sequence as set forth in SEQ ID NO:1 for use in combination with one or more chemotherapeutic agents in the treatment of a human having a cancer selected from the group of: a solid tumour, renal cancer, breast cancer, lung cancer, prostate cancer, colon cancer and leukemia.

In accordance with another aspect of the present invention, there is provided a use of an antisense oligonucleotide of between 7 and 100 nucleotides in length comprising at least 7 consecutive nucleotides from SEQ ID NO:1 in the manufacture of a medicament for the treatment of cancer.

DETAILED DESCRIPTION OF THE INVENTION

Figure 1:
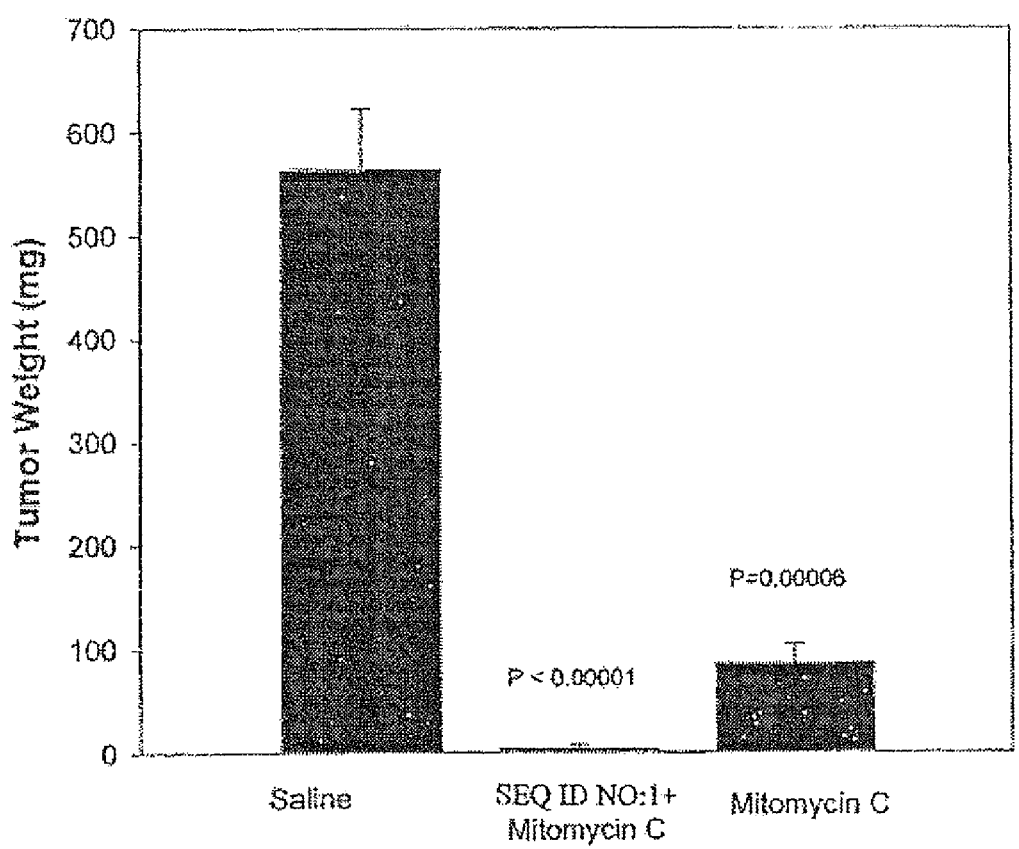
FIG. 1 depicts effects of combination therapy on HT-29 colon tumour growth in nude mice.

The present invention relates to antisense oligonucleotides against the gene encoding a mammalian ribonucleotide reductase R2 protein and combinations of such antisense oligonucleotides and one or more chemotherapeutic agents in the treatment of various cancers. The antisense oligonucleotides and combinations of antisense oligonucleotides with one or more chemotherapeutic agents are effective in decreasing the growth and/or metastasis of cancers, including refractory, advanced and drug resistant cancer cells, than treatment with the antisense oligonucleotide or the chemotherapeutic agent(s) alone.

Definitions

Unless defined otherwise, all technical and scientific terms used herein have the same meaning as commonly understood by one of ordinary skill in the art to which this invention pertains.

The term "antisense oligonucleotide" as used herein means a nucleotide sequence that is complementary to the mRNA for a desired gene. In the context of the present invention, the desired gene is the gene encoding a mammalian ribonucleotide redustase R2 protein.

The term "selectively hybridise" as used herein refers to the ability of a nucleic acid to bind detectably and specifically to a second nucleic acid. Oligonucleotides selectively hybridise to target nucleic acid strands under hybridisation and wash conditions that minimise appreciable amounts of detectable binding to non-specific nucleic acids. High stringency conditions can be used to achieve selective hybridisation conditions as known in the art and discussed herein.

Typically, hybridisation and washing conditions are performed at high stringency according to conventional hybridisation procedures. Washing conditions are typically 1-3× SSC, 0.1-1% SDS, 50-70° C. with a change of wash solution after about 5-30 minutes.

The term "corresponds to" as used herein with reference to nucleic acid sequences means a polynucleotide sequence that is identical to all or a portion of a reference polynucleotide sequence. In contradistinction, the term "complementary to" is used herein to mean that the polynucleotide sequence is identical to all or a portion of the complement of a reference polynucleotide sequence. For illustration, the nucleotide sequence "TATAC" corresponds to a reference sequence "TATAC" and is complementary to a reference sequence "GTATA".

The following terms are used herein to describe the sequence relationships between two or more polynucleotides: "reference sequence," "window of comparison," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence, or may comprise a complete cDNA or gene sequence. Generally, a reference polynucleotide sequence is at least 20 nucleotides in length, and often at least 50 nucleotides in length.

A "window of comparison", as used herein, refers to a conceptual segment of the reference sequence of at least 15 contiguous nucleotide positions over which a candidate sequence may be compared to the reference sequence and wherein the portion of the candidate sequence in the window of comparison may comprise additions or deletions (i.e. gaps) of 20 percent or less as compared to the reference sequence (which does not comprise additions or deletions) for optimal alignment of the two sequences. The present invention contemplates various lengths for the window of comparison, up to and including the full length of either the reference or candidate sequence. Optimal alignment of sequences for aligning a comparison window may be conducted using the local homology algorithm of Smith and Waterman (*Adv. Appl. Math.* (1981) 2:482), the homology alignment algorithm of Needleman and Wunsch (*J. Mol. Biol.* (1970) 48:443), the search for similarity method of Pearson and Lipman (*Proc. Natl. Acad. Sci. (U.S.A.)* (1988) 85:2444), using computerised implementations of these algorithms (such as GAP, BESTFIT, FASTA, and TFASTA in the Wisconsin Genetics Software Package Release 7.0, Genetics Computer Group, 573 Science Dr., Madison, Wis.), using publicly available computer software such as ALIGN or Megalign (DNASTAR), or by inspection. The best alignment (i.e. resulting in the highest percentage of identity over the comparison window) is then selected.

The term "sequence identity" means that two polynucleotide sequences are identical (i.e. on a nucleotide-by-nucleotide basis) over the window of comparison.

The term "percent (%) sequence identity," as used herein with respect to a reference sequence is defined as the percentage of nucleotide residues in a candidate sequence that are identical with the residues in the reference polynucleotide sequence over the window of comparison after optimal alignment of the sequences and introducing gaps, if necessary, to achieve the maximum percent sequence identity, without considering any conservative substitutions as part of the sequence identity.

The term "substantial identity" as used herein denotes a characteristic of a polynucleotide sequence, wherein the polynucleotide comprises a sequence that has at least 50% sequence identity as compared to a reference sequence over the window of comparison. Polynucleotide sequences at least 60% sequence identity, at least 70% sequence identity, at least 80% sequence identity, and at least 90% sequence identity as compared to a reference sequence over the window of comparison are also considered to have substantial identity with the reference sequence.

The terms "therapy," and "treatment," as used interchangeably herein, refer to an intervention performed with the intention of improving a recipient's status. The improvement can be subjective or objective and is related to the amelioration of the symptoms associated with, preventing the development of, or altering the pathology of a disease, disorder or condition being treated. Thus, the terms therapy and treatment are used in the broadest sense, and include the prevention (prophylaxis), moderation, reduction, and curing of a disease, disorder or condition at various stages. Prevention of deterioration of a recipient's status is also encompassed by the term. Those in need of therapy/treatment include those already having the disease, disorder or condition as well as those prone to, or at risk of developing, the disease, disorder or condition and those in whom the disease, disorder or condition is to be prevented.

The term "ameliorate" or "amelioration" includes the arrest, prevention, decrease, or improvement in one or more the symptoms, signs, and features of the disease being treated, both temporary and long-term.

The term "subject" or "patient" as used herein refers to a mammal in need of treatment.

Administration of the compounds of the invention "in combination with" one or more further therapeutic agents, is intended to include simultaneous (concurrent) administration and consecutive administration. Consecutive administration is intended to encompass administration of the therapeutic agent(s) and the compound(s) of the invention to the subject in various orders.

As used herein, the term "about" refers to a +/−10% variation from the nominal value. It is to be understood that such a variation is always included in any given value provided herein, whether or not it is specifically referred to.

Antisense Molecules
Selection and Characteristics

The antisense oligonucleotides of the present invention are targeted to the gene encoding a mammalian ribonucleotide reductase R2 protein. The sequences of various mammalian ribonucleotide reductase genes are known in the art, for example, the sequence for the human ribonucleotide reductase R2 gene is provided in Pavloff et al. [*J. DNA sequencing and Mapping*, 2; 227-234 (1992)]. This and other mammalian R2 sequences are also available from the GenBank database maintained by the NCBI.

The antisense oligonucleotides of the present invention comprise at least 7 contiguous nucleotides, or nucleotide analogues, that correspond to a part of the coding region of a mammalian ribonucleotide reductase R2 gene.

Examples of suitable antisense oligonucleotides for use alone or in the combinations of the present invention include those disclosed in U.S. Pat. Nos. 5,998,383 and 6,121,000 (herein incorporated by reference) which are targeted to the ribonucleotide reductase R2 gene. In one embodiment of the present invention, the antisense oligonucleotide comprises at least 7 consecutive nucleotides of the antisense oligonucleotide represented by the sequence:

5'-GGCTAAATCGCTCCACCAAG-3'    [SEQ ID NO: 1]

The antisense oligonucleotides in accordance with the present invention are selected such that the sequence exhibits the least likelihood of forming duplexes, hair-pins, dimers, or of containing homooligomer/sequence repeats. The oligonucleotide may further contain a GC clamp. One skilled in the art will appreciate that these properties can be determined qualitatively using various computer modelling programs, for example, the program OLIGO® Primer Analysis Software, Version 5.0 (distributed by National Biosciences, Inc., Plymouth, Minn.).

In order to be effective, antisense oligonucleotides are typically between 7 and 100 nucleotides in length. In one embodiment of the present invention, the antisense oligonucleotides are between about 7 to about 50 nucleotides in length. In other embodiments, the antisense oligonucleotides are between about 7 to about 35 nucleotides in length, between about 15 to about 25 nucleotides in length, and about 20 nucleotides in length.

It is understood in the art that an antisense oligonucleotide need not have 100% identity with the complement of its target sequence. The antisense oligonucleotides in accordance with the present invention have a sequence that is at least about 75% identical to the complement of target sequence. In one embodiment of the present invention, the antisense oligonucleotides have a sequence that is at least about 90% identical to the complement of the target sequence. In a related embodiment, they have a sequence that is at least about 95% identical to the complement of target sequence, allowing for gaps or mismatches of several bases. Identity can be determined, for example, by using the BLASTN program of the University of Wisconsin Computer Group (GCG) software or provided on the NCBI website.

The term "antisense oligonucleotides" as used herein includes other oligomeric antisense compounds, including oligonucleotide mimetics, modified oligonucleotides, and chimeric antisense compounds. Chimeric antisense compounds are antisense compounds that contain two or more chemically distinct regions, each made up of at least one monomer unit.

Thus, in the context of this invention, the term "oligonucleotide" refers to an oligomer or polymer of ribonucleic acid (RNA), deoxyribonucleic acid (DNA), or RNA or DNA mimetics. This term, therefore, includes oligonucleotides composed of naturally-occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of antisense compounds useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary antisense oligonucleotides having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In one embodiment of the present invention, the antisense oligonucleotide comprises one or more phosphorothioate internucleotide linkage. In another embodiment, the antisense oligonucleotide comprises phosphorothioate internucleotide linkages that link the four, five or six 3'-terminal nucleotides of the oligonucleotide. In a further embodiment, the antisense oligonucleotide comprises phosphorothioate internucleotide linkages that link all the nucleotides of the oligonucleotide.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridisation with an appropriate nucleic acid target compound. An example of such an oligonucleotide mimetic, which has been shown to have excellent hybridisation properties, is a peptide nucleic acid (PNA) [Nielsen et al., *Science*, 254:1497-1500 (1991)]. In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates oligonucleotides comprising "locked nucleic acids" (LNAs), which are novel conformationally restricted oligonucleotide analogues containing a methylene bridge that connects the 2'-O of ribose with the 4'-C (see, Singh et al., *Chem. Commun.*, 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron*, 1998, 54:3607-3630). Studies of mis-matched sequences show that LNA obey the Watson-Crick base pairing rules with generally improved selectivity compared to the corresponding unmodified reference strands.

Antisense oligonucleotides containing LNAs have been described (Wahlestedt et al., *Proc. Natl. Acad. Sci. U.S.A.*, 2000, 97:5633-5638), which were efficacious and non-toxic. In addition, the LNA/DNA copolymers were not degraded readily in blood serum and cell extracts.

LNAs form duplexes with complementary DNA or RNA or with complementary LNA, with high thermal affinities. The universality of LNA-mediated hybridization has been emphasized by the formation of exceedingly stable LNA:LNA duplexes (Koshkin et al., *J. Am. Chem. Soc.*, 1998, 120: 13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.*, 1998, 8:2219-2222).

Modified oligonucleotides may also contain one or more substituted sugar moieties. For example, oligonucleotides may comprise sugars with one of the following substituents at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy(2'-O—$CH_2CH_2OCH_3$, also known as 2'—O-(2-methoxyethyl) or 2'-MOE) [Martin et al., *Helv. Chim. Acta*, 78:486-504 (1995)], 2'-dimethylaminooxyethoxy($O(CH_2)_2ON(CH_3)_2$ group, also known as 2'-DMAOE), 2'-methoxy(2'-O—$CH_3$), 2'-aminopropoxy(2'-$OCH_2CH_2CH_2NH_2$) and 2'-fluoro (2'-F). In one embodiment of the present invention, the antisense oligonucleotide comprises at least one nucleotide comprising a substituted sugar moiety. In another embodiment, the antisense oligonucleotide comprises at least one 2'—O-(2-methoxyethyl) or 2'-MOE modified nucleotide.

Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.,* 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications*, pp 276-278, Crooke, S. T. and Lebleu, B., ed., CRC Press, Boca Raton].

Another oligonucleotide modification included in the present invention is the chemically linkage to the oligonucleotide of one or more moieties or conjugates which enhance the activity, cellular distribution or cellular uptake of the oligonucleotide. Such moieties include, but are not limited to, lipid moieties such as a cholesterol moiety [Letsinger et al., *Proc. Natl. Acad. Sci. USA,* 86:6553-6556 (1989)], cholic acid [Manoharan et al., *Bioorg. Med. Chem. Let.,* 4:1053-1060 (1994)], a thioether, e.g. hexyl-S-tritylthiol [Manoharan et al., *Ann. N.Y. Acad. Sci.,* 660:306-309 (1992); Manoharan et al., *Bioorg. Med. Chem. Lett.,* 3:2765-2770 (1993)], a thiocholesterol [Oberhauser et al., *Nucl. Acids Res.,* 20:533-538 (1992)], an aliphatic chain, e.g. dodecandiol or undecyl residues [Saison-Behmoaras et al., *EMBO J.,* 10:1111-1118 (1991); Kabanov et al., *FEBS Lett.,* 259:327-330 (1990); Svinarchuk et al., *Biochimie,* 75:49-54 (1993)], a phospholipid, e.g. di-hexadecyl-rac-glycerol or triethylammonium 1,2-di-O-hexadecyl-rac-glycero-3-H-phosphonate [Manoharan et al., *Tetrahedron Lett.,* 36:3651-3654 (1995); Shea et al., *Nucl. Acids Res.,* 18:3777-3783 (1990)], a polyamine or a polyethylene glycol chain [Manoharan et al., *Nucleosides & Nucleotides,* 14:969-973 (1995)], or adamantane acetic acid [Manoharan et al., *Tetrahedron Lett.,* 36:3651-3654 (1995)], a palmityl moiety [Mishra et al., *Biochim. Biophys. Acta,* 1264:229-237 (1995)], or an octadecylamine or hexylaminocarbonyl-oxycholesterol moiety [Crooke et al., *J. Pharmacol. Exp. Ther.,* 277:923-937 (1996)].

One skilled in the art will recognise that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide. The present invention further includes antisense compounds that are chimeric compounds. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridising to the same target region. Cleavage of the RNA target can be routinely detected by gel electrophoresis and, if necessary, associated nucleic acid hybridisation techniques known in the art.

In the context of the present invention, an antisense oligonucleotide is "nuclease resistant" when it has either been modified such that it is not susceptible to degradation by DNA and RNA nucleases or alternatively has been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes. In one embodiment of the present invention, the antisense oligonucleotides are nuclease resistant.

The present invention further contemplates antisense oligonucleotides that contain groups for improving the pharmacokinetic properties of the oligonucleotide, or groups for improving the pharmacodynamic properties of the oligonucleotide.

Preparation of the Antisense Oligonucleotides

The antisense oligonucleotides of the present invention can be prepared by conventional techniques well-known to those skilled in the art. For example, the oligonucleotides can be prepared using solid-phase synthesis using commercially available equipment, such as the equipment available from Applied Biosystems Canada Inc., Mississauga, Canada. As is well-known in the art, modified oligonucleotides, such as phosphorothioates and alkylated derivatives, can also be readily prepared by similar methods.

Alternatively, the antisense oligonucleotides of the present invention can be prepared by enzymatic digestion of the naturally occurring ribonucleotide reductase R2 gene by methods known in the art.

Antisense oligonucleotides can also be prepared through the use of recombinant methods in which expression vectors comprising nucleic acid sequences that encode the antisense oligonucleotides are expressed in a suitable host cell. Such expression vectors can be readily constructed using procedures known in the art. Examples of suitable vectors include, but are not limited to, plasmids, phagemids, cosmids, bacteriophages, baculoviruses and retroviruses, and DNA viruses. One skilled in the art will understand that selection of the appropriate host cell for expression of the antisense oligonucleotide will be dependent upon the vector chosen. Examples of host cells include, but are not limited to, bacterial, yeast, insect, plant and mammalian cells.

One skilled in the art will also understand that the expression vector may further include regulatory elements, such as transcriptional elements, required for efficient transcription of the antisense oligonucleotide sequences. Examples of regulatory elements that can be incorporated into the vector include, but are not limited to, promoters, enhancers, terminators, and polyadenylation signals. One skilled in the art will appreciate that selection of suitable regulatory elements is dependent on the host cell chosen for expression of the antisense oligonucleotide and that such regulatory elements may be derived from a variety of sources, including bacterial, fungal, viral, mammalian or insect genes.

In accordance with the present invention, the expression vectors can be introduced into a suitable host cell or tissue by one of a variety of methods known in the art. Such methods can be found generally described in Sambrook et al., 1992; Ausubel et al., 1989; Chang et al., 1995; Vega et al., 1995; and Vectors: A Survey of Molecular Cloning Vectors and Their Uses (1988) and include, for example, stable or transient transfection, lipofection, electroporation, and infection with recombinant viral vectors.

Chemotherapeutic Agents

When the antisense oligonucleotides of the present invention are used in combination with one or more chemotherapeutic agents, the chemotherapeutic agent can be selected from a wide range of cancer chemotherapeutic agents known in the art. Known chemotherapeutic agents include those that are specific for the treatment of a particular type of cancer as well as those that are applicable to a range of cancers, such as doxorubicin, capecitabine, mitoxantrone, irinotecan (CPT-11) and gemcitabine. Etoposide is generally applicable in the treatment of leukaemias (including acute lymphocytic leukaemia and acute myeloid leukaemia), germ cell tumours, Hodgkin's disease and various sarcomas. Cytarabine (Ara-C) is also applicable in the treatment of various leukaemias, including acute myeloid leukaemia, meningeal leukaemia, acute lymphocytic leukaemia, chronic myeloid leukaemia, erythroleukaemia, as well as non-Hodgkin's lymphoma.

The present invention contemplates the use of both types of chemotherapeutic agent in conjunction with the antisense oligonucleotides. Exemplary chemotherapeutics that can be used alone or in various combinations for the treatment specific cancers are provided in Table 1. One skilled in the art will appreciate that many other chemotherapeutics are available and that the following list is representative only.

TABLE 1

Exemplary Chemotherapeutics used in the Treatment of Some Common Cancers

| CANCER | CHEMOTHERAPEUTIC | |
| --- | --- | --- |
| Acute lymphocytic leukaemia (ALL) | Pegaspargase (e.g. Oncaspar ®) | L-asparaginase |
| | Interleukin-2 (e.g. Proleukin ®) | Cytarabine |
| Acute myeloid leukaemia (AML) | Cytarabine | Idarubicin |
| Brain cancer | Procarbazine (e.g. Matulane ®) | |
| Breast cancer | Capecitabine (e.g. Xeloda ®) | Cyclophosphamide |
| | 5-fluorouracil (5-FU) | Carboplatin |
| | Paclitaxel (e.g. Taxol ®) | Cisplatin |
| | Docetaxel (e.g. Taxotere ®) | Ifosfamide |
| | Epi-doxorubicin (epirubicin) | Doxorubicin (e.g. Adriamycin ®) |
| | Trastuzumab (Herceptin ®) | Tamoxifen |
| Chronic myeloid leukaemia (CML) | Low-dose Interferon (IFN)-alpha | |
| | Cytarabine | |
| Colon cancer | Edatrexate (10-ethyl-10-deaza-aminopterin) | |
| | Methyl-chloroethyl-cyclohexyl-nitrosourea | |
| | 5-fluorouracil (5-FU) | Levamisole |
| | Fluorodeoxyuridine (FUdR) | Vincristine |
| | Capecitabine (e.g. Xeloda ®) | Oxaliplatin |
| Colorectal cancer | Irinotecan (CPT-11, e.g. Camptosar ®) | |
| | Loperamide (e.g. Imodium ®) | |
| | Topotecan (e.g. Hycamtin ®) | |
| | Capecitabine (e.g. Xeloda ®) | |
| | 5-fluorouracil (5-FU) | |
| Gall bladder | 5-fluorouracil (5-FU) | |
| Genitourinary cancer | Docetaxel (e.g. Taxotere ®) | |
| Head and neck cancer | Docetaxel (e.g. Taxotere ®) | Cisplatin |
| Non-Hodgkin's Lymphoma | Procarbazine (e.g. Matulane ®) | Cytarabine |
| | Rituximab (e.g. Rituxan ®) | Etoposide |
| Non-small-cell lung (NSCL) cancer | Vinorelbine Tartrate (e.g. Navelbine ®) | |
| | Irinotecan (CPT-11, e.g. Camptosar ®) | |
| | Docetaxel (e.g. Taxotere ®) | Paclitaxel (e.g. Taxol ®) |
| | Gemcitabine (e.g. Gemzar ®) | Topotecan |
| Oesophageal cancer | Porfimer Sodium (e.g. Photofrin ®) | |
| | Cisplatin | |
| Ovarian cancer | Irinotecan (CPT-11, e.g. Camptosar ®) | |
| | Topotecan (e.g. Hycamtin ®) | |
| | Docetaxel (e.g. Taxotere ®) | Paclitaxel (e.g. Taxol ®) |
| | Gemcitabine (e.g. Gemzar ®) | Amifostine (e.g. Ethyol ®) |
| Pancreatic cancer | Irinotecan (CPT-11, e.g. Camptosar ®) | |
| | Gemcitabine (e.g. Gemzar ®) | 5-fluorouracil (5-FU) |
| Promyelocytic leukaemia | Tretinoin (e.g. Vesanoid ®) | |
| Prostate cancer | Goserelin Acetate (e.g. Zoladex ®) | |
| | Mitoxantrone (e.g. Novantrone ®) | |
| | Prednisone (e.g. Deltasone ®) | Liarozole |
| | Nilutamide (e.g. Nilandron ®) | Flutamide (e.g. Eulexin ®) |
| | Finasteride (e.g. Proscar ®) | Terazosin (e.g. Hytrin ®) |
| | Doxazosin (e.g. Cardura ®) | Cyclophosphamide |
| | Docetaxel (e.g. Taxotere ®) | Estramustine |

TABLE 1-continued

Exemplary Chemotherapeutics used in the Treatment of Some Common Cancers

| CANCER | CHEMOTHERAPEUTIC | |
| --- | --- | --- |
| Renal cancer | Capecitabine (e.g. Xeloda ®) | |
| | Gemcitabine (e.g. Gemzar ®) | |
| | Interleukin-2 (e.g. Proleukin ®) | |
| Small cell lung cancer | Cyclophosphamide | Vincristine |
| | Doxorubicin | Etoposide |
| Solid tumours | Gemicitabine (e.g. Gemzar ®) | Cyclophosphamide |
| | Capecitabine (e.g. Xeloda ®) | Ifosfamide |
| | Paclitaxel (e.g. Taxol ®) | Cisplatin |
| | Docetaxel (e.g. Taxotere ®) | Carboplatin |
| | Epi-doxorubicin (epirubicin) | Doxorubicin (e.g. Adriamycin ®) |
| | 5-fluorouracil (5-FU) | |

As indicated above, combinations of chemotherapeutics may be employed. Combination therapies using standard cancer chemotherapeutics are well known in the art and such combinations also can be used in conjunction with the antisense oligonucleotides of the invention.

Exemplary combination therapies include for the treatment of breast cancers the combination of epirubicin with paclitaxel or docetaxel, or the combination of doxorubicin or epirubicin with cyclophosphamide. Polychemotherapeutic regimens are also useful and may consist, for example, of doxorubicin/cyclophosphamide/5-fluorouracil or cyclophosphamide/epirubicin/5-fluorouracil. Many of the above combinations are useful in the treatment of a variety of other solid tumours.

Combinations of etoposide with either cisplatin or carboplatin are used in the treatment of small cell lung cancer. In the treatment of stomach or oesophageal cancer, combinations of doxorubicin or epirubicin with cisplatin and 5-fluorouracil are useful. For colorectal cancer, CPT-11 in combination with 5-fluorouracil-based drugs, or oxaliplatin in combination with 5-fluorouracil-based drugs can be used. Oxaliplatin may also be used in combination with capecitabine.

Other examples include the combination of cyclophosphamide, doxorubicin, vincristine and prednisone in the treatment of non-Hodgkin's lymphoma; the combination of doxorubicin, bleomycin, vinblastine and dacarbazine (DTIC) in the treatment of Hodgkin's disease and the combination of cisplatin or carboplatin with any one, or a combination, of gemcitabine, paclitaxel, docetaxel, vinorelbine or etoposide in the treatment of non-small cell lung cancer.

Various sarcomas are treated by combination therapy, for example, for osteosarcoma combinations of doxorubicin and cisplatin or methotrexate with leucovorin are used; for advanced sarcomas etoposide can be used in combination with ifosfamide; for soft tissue sarcoma doxorubicin or dacarbazine can be used alone or, for advanced sarcomas doxorubicin can be used in combination with ifosfamide or dacarbazine, or etoposide in combination with ifosfamide.

Ewing's sarcoma/peripheral neuroectodermal tumour (PNET) or rhabdomyosarcoma can be treated using etoposide and ifosfamide, or a combination of vincristine, doxorubicin and cyclophosphamide.

The alkylating agents cyclophosphamide, cisplatin and melphalan are also often used in combination therapies with other chemotherapeutics in the treatment of various cancers.

Examples of suitable combinations of the antisense oligonucleotide and one or more chemotherapeutic agent include, but are not limited to, a combination of the antisense oligonucleotide with capecitabine, alone or in combination with other chemotherapeutics, for the treatment of solid tumours including, but not limited to, breast cancer, renal cancer, colon cancer, colorectal cancer and pancreatic cancer, for example, a combination of capecitabine and oxaliplatin for the treatment of colorectal cancer, colon cancer and pancreatic cancer or a combination of capecitabine and gemcitabine for the treatment of colon cancer;

with a combination of carboplatin and paclitaxel for the treatment of metastatic cancers;

with cisplatin, alone or in combination with other chemotherapeutics, for the treatment of head and neck cancer, oesophageal cancer, lung cancer, ovarian cancer and cervical cancer, for example a combination of cisplatin and irinotecan for the treatment of small-cell lung carcinoma (SCLC);

with cytarabine, alone or in combination with other chemotherapeutics, for the treatment of acute myeloid leukaemia (AML) and chronic myeloid leukaemia (CML), for example, a combination of cytarabine, fludarabine and filgrastim for the treatment of CML, or a combination of cytarabine, mitoxantrone and etoposide for the treatment of AML;

with dacarbazine for the treatment of melanoma;

with docetaxel, alone or in combination with other chemotherapeutics, for the treatment of solid tumours, including, but not limited to, non-small cell lung carcinoma (NSCLC), breast cancer, prostate cancer and cancer of the genitourinary tract;

with 5-FU, alone or in combination with other chemotherapeutics, for the treatment of renal cancer, pancreatic cancer, and cancers of the gall bladder or biliary ducts;

with gemcitabine, alone or in combination with other chemotherapeutics, for the treatment of solid tumours, including, but not limited to, NSCLC, breast cancer and renal cancer, for example, a combination of gemcitabine and oxaliplatin for the treatment of breast cancer;

with hydroxyurea, alone or in combination with other chemotherapeutics, for the treatment of cervical cancer;

with idarubicin, alone or in combination with other chemotherapeutics, for the treatment of AML;

with irinotecan, alone or in combination with other chemotherapeutics, for the treatment of pancreatic cancer and colon cancer;

with mitoxantrone, alone or in combination with other chemotherapeutics, for the treatment of prostate cancer and colon cancer, for example, a combination of mitoxantrone and prednisone for the treatment of prostate cancer;

with taxol, alone or in combination with other chemotherapeutics, for the treatment of ovarian cancer and breast cancer, and with vinblastine, alone or in combination with other chemotherapeutics, for the treatment of renal cancer.

Efficacy of the Antisense Oligonucleotides and Combinations

The antisense oligonucleotides of the present invention can be initially tested, alone or in combination with other chemotherapeutic(s), for their ability to attenuate the growth and/or metastasis of cancer cells in vitro and/or in vivo. Methods of testing potential anti-cancer compounds are known in the art. Exemplary, non-limiting tests are provided below and in the Examples included herein.

1. In Vitro Testing

Initial determinations of the efficacy of the antisense oligonucleotides alone, or in combination with one or more chemotherapeutic agents ("combinations"), may be made using in vitro techniques if required.

For example, the antisense oligonucleotides or combinations of the antisense oligonucleotides with one or more chemotherapeutic agents can be tested in vitro by determining their ability to inhibit anchorage-independent growth of tumour cells. Anchorage-independent growth is known in the art to be a good indicator of tumourigenicity. In general, anchorage-independent growth is assessed by plating cells from an appropriate cancer cell-line onto soft agar and determining the number of colonies formed after an appropriate incubation period. Growth of cells treated with the antisense oligonucleotides alone or combinations can then be compared with that of cells treated with an appropriate control (such as cells treated with a scrambled control oligonucleotide or a known chemotherapeutic, or untreated cells) and with that of untreated cells.

Typically in vitro testing of the antisense oligonucleotides and combinations is conducted in a human cancer cell-line. Examples of suitable cancer cell-lines for in vitro testing of the antisense oligonucleotides or combinations of the present invention are known in the art and include those described in the Examples provided herein.

If necessary, the toxicity of the antisense oligonucleotides and combinations can also be initially assessed in vitro using standard techniques. For example, human primary fibroblasts can be treated in vitro with the oligonucleotide in the presence of a commercial lipid carrier such as lipofectamine. Cells are then tested at different time points following treatment for their viability using a standard viability assay, such as the trypan-blue exclusion assay. Cells are also assayed for their ability to synthesize DNA, for example, using a thymidine incorporation assay, and for changes in cell cycle dynamics, for example, using a standard cell sorting assay in conjunction with a fluorocytometer cell sorter (FACS).

2. In Vivo Testing

The ability of the antisense oligonucleotides and combinations to inhibit tumour growth or proliferation in vivo can be determined in an appropriate animal model using standard techniques known in the art (see, for example, Enna, et al., *Current Protocols in Pharmacology*, J. Wiley & Sons, Inc., New York, N.Y.).

In general, current animal models for screening anti-tumour compounds are xenograft models, in which a human tumour has been implanted into an animal. Examples of xenograft models of human cancer include, but are not limited to, human solid tumour xenografts in mice, implanted by sub-cutaneous injection and used in tumour growth assays; human solid tumour isografts in mice, implanted by fat pad injection and used in tumour growth assays; experimental models of lymphoma and leukaemia in mice, used in survival assays, and experimental models of lung metastasis in mice. Representative, non-limiting examples are provided in Table 2 and in the Examples provided herein.

For example, the antisense oligonucleotides and combinations can be tested in vivo on solid tumours using mice that are subcutaneously grafted bilaterally with a pre-determined amount of a tumour fragment on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random into groups that will undergo the treatments or act as controls. Suitable groupings would be, for example, those receiving the combination of the invention, those receiving the antisense alone, those receiving the chemotherapeutic agent(s) alone and those receiving no treatment. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. The antisense oligonucleotides or combinations of the present invention can be administered to the animals, for example, by bolus infusion. The different animal groups are weighed about 3 or 4 times a week until the maximum weight loss is attained, after which the groups are weighed at least once a week until the end of the trial.

The tumours are measured about 2 or 3 times a week until the tumour reaches a pre-determined size and/or weight, or until the animal dies if this occurs before the tumour reaches the pre-determined size/weight. The animals are then sacrificed and the tissue histology, size and/or proliferation of the tumour assessed.

For the study of the effect of the antisense oligonucleotides and combinations on leukaemias, the animals are grafted with a particular number of cells, and the anti-tumour activity is determined by the increase in the survival time of the treated mice relative to the controls.

To study the effect of the antisense oligonucleotides and combinations of the present invention on tumour metastasis, tumour cells are typically treated with the composition ex vivo and then injected into a suitable test animal. The spread of the tumour cells from the site of injection is then monitored over a suitable period of time by standard techniques.

In vivo toxic effects of the oligonucleotides can be evaluated by measuring their effect on animal body weight during treatment and by performing haematological profiles and liver enzyme analysis after the animal has been sacrificed.

TABLE 2

Examples of xenograft models of human cancer

| Cancer Model | Cell Type |
|---|---|
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance) Liver (HepG2) Brain (U87-MG) |

TABLE 2-continued

Examples of xenograft models of human cancer

| Cancer Model | Cell Type |
| --- | --- |
| | Renal (Caki-1, A498) |
| | Ovary (SK-OV-3) |
| Tumour Growth Assay | Breast: drug resistant (MDA-CDDP-S4, |
| Human solid tumour isografts in mice (fat pad injection) | MDA-MB435-To.1) |
| Survival Assay | Human: Burkitts lymphoma (Non- |
| Experimental model of lymphoma and leukaemia in mice | Hodgkin's) (raji) |
| | Murine: erythroleukaemia (CB7 Friend retrovirus-induced) |
| Experimental model of lung metastasis in mice | Human: melanoma (C8161) |
| | Murine: fibrosarcoma (R3) |

Pharmaceutical Compositions

For the treatment of cancer in a mammal, the antisense oligonucleotide may be administered as a pharmaceutical composition comprising the antisense oligonucleotide in admixture with an appropriate pharmaceutically physiologically acceptable carrier, diluent, excipient or vehicle. The pharmaceutical compositions may also be formulated to contain the antisense oligonucleotide and one or more other chemotherapeutic agents for concurrent administration to a patient, where appropriate.

The pharmaceutical compositions of the present invention may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous, intravenous, intramuscular, intrasternal, intrathecal injection or infusion techniques.

The pharmaceutical compositions may be in a form suitable for oral use, for example, as tablets, troches, lozenges, aqueous or oily suspensions, dispersible powders or granules, emulsion hard or soft capsules, or syrups or elixirs. Compositions intended for oral use may be prepared according to methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Aqueous suspensions contain the active compound in admixture with suitable excipients including, for example, suspending agents, such as sodium carboxymethylcellulose, methyl cellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-deca-ethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose or saccharin.

Oily suspensions may be formulated by suspending the active ingredients in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example, olive oil or arachis oil, or a mineral oil, for example, liquid paraffin, or it may be a mixtures of these oils. Suitable emulsifying agents may be naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative, and/or flavouring and colouring agents.

The pharmaceutical compositions may be in the form of a sterile injectable aqueous or oleaginous suspension. This suspension may be formulated according to known art using suitable dispersing or wetting agents and suspending agents such as those mentioned above. The sterile injectable preparation may also be sterile injectable solution or suspension in a non-toxic parentally acceptable diluent or solvent, for example, as a solution in 1,3-butanediol, water, Ringer's solution, lactated Ringer's solution or isotonic sodium chloride solution. Other examples of acceptable vehicles and solvents that may be employed include, but are not limited to, sterile, fixed oils which are conventionally employed as a solvent or suspending medium, and a variety of bland fixed oils including, for example, synthetic mono- or diglycerides. In addition, fatty acids such as oleic acid find use in the preparation of injectables. Injectable compositions are also suitable for administration by continuous infusion.

In one embodiment of the present invention, the antisense oligonucleotide is formulated as an injectable composition.

Other pharmaceutical compositions and methods of preparing pharmaceutical compositions are known in the art and are described, for example, in "*Remington: The Science and Practice of Pharmacy*," Gennaro, A., Lippincott, Williams & Wilkins, Philadelphia, Pa. (2000) (formerly "*Remingtons Pharmaceutical Sciences*").

Use of the Antisense Oligonucleotides and Combinations

The antisense oligonucleotides of the present invention and combinations comprising an antisense oligonucleotide and one or more chemotherapeutic agents can be used in the treatment of a variety of cancers. In one embodiment of the present invention, the combination is more effective in reducing the growth and/or metastasis of cancer cells than the chemotherapeutic agent(s) alone. The antisense oligonucleotides and combinations can also be used to effectively treat drug resistant tumours.

Examples of cancers which may be may be treated, stabilised, or prevented in accordance with the present invention include, but are not limited to leukaemia, carcinomas, adenocarcinomas, sarcomas, lymphomas and melanomas. Carcinomas, adenocarcinomas and sarcomas are also frequently referred to as "solid tumours," examples of commonly occurring solid tumours include, but are not limited to, cancer of the brain, breast, cervix, colon, head and neck, kidney, lung, ovary, pancreas, prostate, lung, stomach and uterus, and colorectal cancer. Lymphomas are also considered to be solid tumours.

The term "leukaemia" refers broadly to progressive, malignant diseases of the blood-forming organs. Leukaemia is typically characterised by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, acute myeloid leukaemia (AML), chronic myeloid leukaemia (CML), adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colorectal carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, non-small cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Commonly occurring carcinomas that may be treated with the antisense oligonucleotides of the present invention, include, for example, pancreatic, ovarian, lung, liver, renal and cervical carcinomas.

The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia. Examples include, but are not limited to, adenocarcinomas of the breast, lung, pancreas, colon and prostate.

The term "sarcoma" generally refers to a tumour which originates in connective tissue, such as muscle, bone, cartilage or fat, and is made up of a substance like embryonic connective tissue and is generally composed of closely packed cells embedded in a fibrillar or homogeneous substance. Sarcomas include soft tissue sarcomas, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The antisense oligonucleotides of the present invention can also be used in the treatment of lymphomas including Hodgkin's and non-Hodgkin's lymphomas and brain cancers including primary brain tumours, gliomas, glioblastoma multiforme; malignant astrocytomas; oligdendroglioma; ependymoma; low-grade astrocytomas; meningioma; mesenchymal tumours; pituitary tumours; nerve sheath tumours such as schwannomas; central nervous system lymphoma; medulloblastoma; primitive neuroectodermal tumours; neuron and neuron/glial tumours; craniopharyngioma; germ cell tumours and choroid plexus tumours. Additional cancers include multiple myeloma, neuroblastoma, rhabdomyosarcoma, primary thrombocytosis, primary macroglobulinemia, small-cell lung tumours, malignant pancreatic insulanoma, malignant carcinoid, urinary bladder cancer, premalignant skin lesions, testicular cancer, thyroid cancer, oesophageal cancer, genitourinary tract cancer, malignant hypercalcemia, endometrial cancer, adrenal cortical cancer and mesothelioma.

The cancer may be indolent or it may be aggressive. The antisense oligonucleotides are useful in the treatment of refractory cancers, advanced cancers, recurrent cancers, relapsed and metastatic cancers. One skilled in the art will appreciate that many of these categories may overlap, for example, aggressive cancers are typically also advanced and/or metastatic.

"Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC) nearly all cases present rapidly growing cancers which are considered to be aggressive. The term can thus cover a subsection of a certain cancer type or it may encompass all of other cancer types. A "refractory" cancer or tumour refers to a cancer or tumour that has not responded to treatment. "Advanced cancer," refers to overt disease in a patient, wherein such overt disease is not amenable to cure by local modalities of treatment, such as surgery or radiotherapy. Advanced disease may refer to a locally advanced cancer or it may refer to metastatic cancer. The term "metastatic cancer" refers to cancer that has spread from one part of the body to another. Advanced cancers may also be unresectable, that is, they have spread to surrounding tissue and cannot be surgically removed.

The antisense oligonucleotides may also be used to treat drug resistant cancers, including multidrug resistant tumours. As is known in the art, the resistance of cancer cells to chemotherapy is one of the central problems in the management of cancer.

Certain cancers, such as prostate and breast cancer, can be treated by hormone therapy, i.e. with hormones or anti-hormone drugs that slow or stop the growth of certain cancers by blocking the body's natural hormones. Such cancers may develop resistance, or be intrinsically resistant, to hormone therapy. The present invention further contemplates the use of the antisense oligonucleotide in the treatment of these "hormone-resistant" or "hormone-refractory" cancers.

In one embodiment of the present invention, the antisense oligonucleotide alone, or in combination with one or more chemotherapeutic, is used in the treatment of solid tumours including metastatic, advanced, drug- or hormone-resistant versions of solid tumours. In another embodiment, the solid tumour is a renal tumour, breast tumour, lung tumour, prostate tumour, colon tumour, melanoma, ovarian tumour, cervical tumour, brain tumour, liver tumour, colorectal tumour, pancreatic tumour, genitourinary tumour, gall bladder tumour, head and neck tumour, oesophageal tumour biliary duct tumour, a lymphoma, or a sarcoma, including a metastatic, advanced, drug- or hormone-resistant version thereof. In a further embodiment, the solid tumour is an ovarian tumour, a renal tumour, a brain tumour, or a sarcoma, including a metastatic, advanced, or drug-resistant version thereof.

In an alternate embodiment, the antisense oligonucleotide alone, or in combination with one or more chemotherapeutic, is used in the treatment of a leukaemia, including a metastatic, advanced or drug-resistant version thereof.

Administration of the Antisense Oligonucleotides

The dose of the antisense oligonucleotide of the present invention to be administered to a patient should be a sufficient amount to effect a beneficial therapeutic response in the patient over time, i.e. an "effective amount." Such a beneficial therapeutic response may be, for example, stabilisation of the disease, tumour shrinkage, decreased time to progression or prolonged survival. The dose will be determined by the efficacy of the particular oligonucleotide employed, the type of cancer to be treated and the condition of the patient to be treated, as well as the body weight or surface area of the patient. Appropriate doses can be readily determined by a skilled practitioner.

Typically, antisense oligonucleotides are administered systemically to patients. Administration can be accomplished by bolus injection as a single dose or as divided doses, or by continuous infusion over an appropriate period of time.

In one embodiment of the present invention, the antisense oligonucleotides are administered by continuous infusion. In another embodiment, the antisense oligonucleotides are administered by continuous intravenous infusion.

As indicated above, the dosage of the antisense oligonucleotide to be administered will be dependent upon the type of cancer to be treated and the size of the patient and can be readily determined by a skilled practitioner. By way of example only, for the antisense oligonucleotide represented by SEQ ID NO:1, appropriate doses determined by Phase I clinical trials are between about 18.5 mg/m$^2$/day and about 222 mg/m$^2$/day. In one embodiment, the dose of antisense oligonucleotide is between about 37 mg/m$^2$/day and about 222 mg/m$^2$/day. In another embodiment, the dose of antisense oligonucleotide is between about 74 mg/m$^2$/day and about 185 mg/m$^2$/day. In further embodiments, the dose of antisense oligonucleotide is between about 100 mg/m$^2$/day and about 185 mg/m$^2$/day and between about 148 mg/m$^2$/day and about 185 mg/m$^2$/day. Other exemplary doses for SEQ ID NO:1 include doses between about 2 mg/kg/day and about 10 mg/kg/day, between about 3 mg/kg/day and about 8 mg/kg/day and between about 3 mg/kg/day and about 5 mg/kg/day.

Treatment regimens can be designed such that the antisense oligonucleotide is administered to the patient in cycles. Treatment with antisense oligonucleotide in accordance with the present invention, therefore, may be part of a treatment regimen that involves one cycle of administration or more than one cycle. Typically, a cycle is between about 1 and about 4 weeks. Exemplary dosing schedules comprise one or more cycle of 21 days continuous infusion followed by 7 days of rest or one or more cycles of 14 days continuous infusion followed by 7 days of rest. Further examples are provided in the Examples section herein. Other treatment regimens can be readily determined by the skilled practitioner. Between one and sixteen cycles of treatment are contemplated, however, additional cycles may be incorporated into the treatment regimen as necessary.

The present invention contemplates the use of the antisense oligonucleotides, alone or in combination with one or more other chemotherapeutic agents, to treat patients who have undergone prior chemotherapy. Thus, in one embodiment of the invention, the antisense oligonucleotides are used as a second or subsequent (for example, third or fourth) line of therapy. In an alternate embodiment, the antisense oligonucleotides are used to treat patients who have already undergone more than one course of prior chemotherapy. The antisense oligonucleotides, alone or in combination with one or more other chemotherapeutic agents, may also be used as a first line of therapy in the treatment of patients for whom standard chemotherapy is not suitable.

As indicated above, the antisense oligonucleotide can be administered to the patient in conjunction with one or more chemotherapeutic agents. In such combination therapy, the antisense oligonucleotide can be administered prior to, or after, administration of the one or more other chemotherapeutic agents, or it can be administered concurrently. The one or more chemotherapeutic may be administered systemically, for example, by bolus injection or continuous infusion, or it may be administered orally.

The one or more other chemotherapeutic may also be administered in cycles, which may or may not overlap with the cycles of administration for the antisense oligonucleotide. When the antisense oligonucleotide is administered prior to the one or more other chemotherapeutic agents, the length of time between the initiation of administration of the antisense oligonucleotide and the other agent(s) will depend on the mode of administration, the size of the patient and the nature of the other agent(s) being administered. Similarly, if the antisense oligonucleotide and the one or more other chemotherapeutic agents are administered concurrently, administration of the compounds may be initiated at the same time, or administration of the other chemotherapeutic(s) may be initiated at a suitable time prior to or after administration of the antisense oligonucleotide is initiated. Appropriate treatment regimens can be readily determined by the skilled practitioner.

Appropriate doses and treatment regimens for standard chemotherapeutics for the treatment of a variety of cancers are well known in the art. The following are provided by way of example only and are not intended to limit the scope of the present invention in any way.

Capecitabine can be administered at a dose of between about 500 and about 2000 mg/m$^2$/day. Capecitabine is typically administered orally. Administration of the daily amount may be via a single dose or divided doses. Exemplary doses would be between about 500-1500 mg/m$^2$/day, between about 600-1000 mg/m$^2$/day, and between about 1100-2000 mg/m$^2$/day depending on the type of cancer being treated. In one embodiment, capecitabine at a dose of between 850 and 1700 mg/m$^2$/day is used in conjunction with the antisense oligonucleotide. In another embodiment, doses of 850, 1250 and 1660 mg/m$^2$/day are used.

Cytarabine can be administered at various doses between about 5 and about 3000 mg/m$^2$/day depending on the type of cancer being treated and the dosing schedule employed. Administration of the daily amount of cytarabine may be via a single dose, divided dose or continuous infusion. Exemplary doses would be between about 500-1000 mg/m$^2$/day, between about 1000-2000 mg/m$^2$/day and between about 4000-6000 mg/m$^2$/day. In one embodiment, cytarabine at a dose of between about between about 4000-6000 mg/m$^2$/day is used in conjunction with the antisense oligonucleotide.

For some indications, cytarabine can be administered intrathecally at a dose of between about 5-75 mg/m$^2$/day and between about 100-200 mg/m$^2$/day, depending on the type of cancer being treated and the dosing schedule employed. Thus, for certain cancers, cytarabine is used at a dose of between about 5-75 mg/m$^2$/day in conjunction with the antisense oligonucleotide.

Docetaxel can be administered at a dose of between about 20 and about 100 mg/m$^2$ per one dose. Exemplary doses would be between about 30-35 mg/m$^2$, between about 30-36 mg/m$^2$, between about 60-75 mg/m$^2$, between about 40-80 mg/m$^2$ and between about 60-100 mg/m$^2$ depending on the type of cancer being treated and the dosing schedule employed. In one embodiment, docetaxel at a dose of between about 60 mg/m$^2$ and about 75 mg/m$^2$ is used in conjunction with the antisense oligonucleotide.

Single dose units of gemcitabine are typically between about 100 and about 2500 mg/m$^2$. Exemplary dose units suitable for use with the antisense oligonucleotides would be between about 400-1000 mg/m$^2$, between about 600-1000 mg/m$^2$, between about 800-1000 mg/m$^2$, between about 500-1250 mg/m$^2$, between about 750-1200 mg/m$^2$, between about 800-1250 mg/m$^2$, between about 1000-1200 mg/m$^2$, between about 1250-2500 mg/m$^2$, depending on the type of cancer being treated and the dosing schedule employed. The dose maybe administered, for example, weekly or biweekly. In one embodiment, a weekly unit dose of between about 400-1000 mg/m$^2$ gemcitabine is used in conjunction with the antisense oligonucleotide.

For some indications, gemcitabine can also be administered at lower doses, for example, between about 100 to about 400 mg/m$^2$/day depending on the type of cancer being treated.

Oxaliplatin can be administered at a dose of between about 30 and about 135 mg/m$^2$/day. Administration of the daily amount of oxaliplatin may be via a single dose or divided doses, or by continuous infusion. Exemplary doses would be between about 80-100 mg/m$^2$/day and between about 85-135 mg/m$^2$/day depending on the type of cancer being treated and the dosing schedule employed. In one embodiment, oxaliplatin at a dose of about 130 mg/m$^2$/day is used in conjunction with the antisense oligonucleotide.

It is to be understood, however, that the above exemplary dosages and frequencies of administration may be adapted to the circumstances in accordance with known practices in the art for the treatment of different cancers.

Clinical Trials in Cancer Patients

One skilled in the art will appreciate that, following the demonstrated effectiveness of the antisense oligonucleotides alone or combinations of the present invention in vitro and in animal models, they should be tested in Clinical Trials in order to further evaluate their efficacy in the treatment of cancer and to obtain regulatory approval for therapeutic use.

As is known in the art, clinical trials progress through phases of testing, which are identified as Phases I, II, III, and IV.

Initially the antisense oligonucleotides alone or combinations will be evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of a compound in the body of the patient. For a Phase I trial, a small group of cancer patients are treated with a specific dose of the antisense oligonucleotide and the one or more chemotherapeutic agent(s). During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to evaluate further the effectiveness and safety of the antisense oligonucleotides alone or combinations. In Phase II trials, the antisense oligonucleotides alone or the combination is administered to groups of patients with either one specific type of cancer or with related cancers, using the dosage found to be effective in Phase I trials.

Phase III trials focus on determining how a compound compares to the standard, or most widely accepted, treatment. In Phase III trials, patients are randomly assigned to one of two or more "arms". In a trial with two arms, for example, one arm will receive the standard treatment (control group) and the other arm will receive treatment with the antisense oligonucleotide or combination of the present invention (investigational group).

Phase IV trials are used to further evaluate the long-term safety and effectiveness of a compound. Phase IV trials are less common than Phase I, II and III trials and will take place after the antisense oligonucleotide or combination has been approved for standard use.

Eligibility of Patients for Clinical Trials

Participant eligibility criteria can range from general (for example, age, sex, type of cancer) to specific (for example, type and number of prior treatments, tumour characteristics, blood cell counts, organ function). Eligibility criteria may also vary with trial phase. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I cancer trials usually comprise 15 to 30 participants for whom other treatment options have not been effective. Phase II trials typically comprise up to 100 participants who have already received chemotherapy, surgery, or radiation treatment, but for whom the treatment has not been effective. Participation in Phase II trials is often restricted based on the previous treatment received. Phase III trials usually comprise hundreds to thousands of participants. This large number of participants is necessary in order to determine whether there are true differences between the effectiveness of the antisense oligonucleotides or combination of the present invention and the standard treatment. Phase III may comprise patients ranging from those newly diagnosed with cancer to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example, using the Eastern Cooperative Oncology Group (ECOG) Performance Status (PS) scale or the Karnofsky Performance Status (KPS) scale, both of which are widely accepted standards for the assessment of the progression of a patient's disease as measured by functional impairment in the patient.

Patients' overall quality of life can be assessed, for example, using the McGill Quality of Life Questionnaire (MQOL) (Cohen et al (1995) *Palliative Medicine* 9: 207-219). The MQOL measures physical symptoms; physical, psychological and existential well-being; support; and overall quality of life. To assess symptoms such as nausea, mood, appetite, insomnia, mobility and fatigue the Symptom Distress Scale (SDS) developed by McCorkle and Young ((1978) *Cancer Nursing* 1: 373-378) can be used.

Patients can also be classified according to the type and/or stage of their disease and/or by tumour size.

Administration of the Antisense Oligonucleotides Alone or Combinations of the Present Invention in Clinical Trials The antisense oligonucleotide and the one or more chemotherapeutic agent(s) are typically administered to the trial participants parenterally. In one embodiment, the antisense oligonucleotide or combination is administered by intravenous infusion. Methods of administering drugs by intravenous infusion are known in the art. Usually intravenous infusion takes place over a certain time period, for example, over the course of 60 minutes.

Monitoring of Patient Outcome

The endpoint of a clinical trial is a measurable outcome that indicates the effectiveness of a treatment under evaluation. The endpoint is established prior to the commencement of the trial and will vary depending on the type and phase of the clinical trial. Examples of endpoints include, for example, tumour response rate—the proportion of trial participants whose tumour was reduced in size by a specific amount, usually described as a percentage; disease-free survival—the amount of time a participant survives without cancer occurring or recurring, usually measured in months; overall survival—the amount of time a participant lives, typically measured from the beginning of the clinical trial until the time of death. For advanced and/or metastatic cancers, disease stabilisation—the proportion of trial participants whose disease has stabilised, for example, whose tumour(s) has ceased to grow and/or metastasise, can be used as an endpoint. Other endpoints include toxicity and quality of life.

Tumour response rate is a typical endpoint in Phase II trials. However, even if a treatment reduces the size of a participant's tumour and lengthens the period of disease-free survival, it may not lengthen overall survival. In such a case, side effects and failure to extend overall survival might outweigh the benefit of longer disease-free survival. Alternatively, the participant's improved quality of life during the tumour-free interval might outweigh other factors. Thus, because tumour response rates are often temporary and may not translate into long-term survival benefits for the participant, response rate is a reasonable measure of a treatment's effectiveness in a Phase II trial, whereas participant survival and quality of life are typically used as endpoints in a Phase III trial.

Pharmaceutical Kits

The present invention additionally provides for therapeutic kits containing the antisense oligonucleotide and optionally one or more chemotherapeutic agents in pharmaceutical compositions for use in the treatment of cancer. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or any such medically approved delivery vehicle.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

To gain a better understanding of the invention described herein, the following examples are set forth. It should be understood that these examples are for illustrative purposes only. Therefore, they should not limit the scope of this invention in any way.

EXAMPLES

SEQ ID NO:1 as referred to throughout the Examples is a fully phosphorothioated oligonucleotide with the sequence:

```
5'-GGCTAAATCGCTCCACCAAG-3'    [SEQ ID NO: 1]
```

SEQ ID NO:1 hybridizes to the coding region of R2 mRNA.

SEQ ID NO:2 is a mismatched control analogue of SEQ ID NO:1, having four base changes in the middle of the sequence:

```
5'-GGCTAAACTCGTCCACCAAG-3'    [SEQ ID NO: 2]
```

SEQ ID NO:3 is a scrambled control analogue of SEQ ID NO:1 that is not complementary to R2, but retains the same base composition ratio as SEQ ID NO:1.

```
5'-ACGCACTCAGCTAGTGACAC-3'    [SEQ ID NO: 3]
```

The phosphorothioates were synthesized on an automated DNA synthesizer (Perkin-Elmer, USA) by Boston BioSystem Inc. (Boston, Mass.) and were purified by reversed-phase high performance liquid chromatography.

Example 1

In Vivo Testing of SEQ ID NO: 1 in Combination with Various Chemotherapeutics in Mouse Xenograft Models 1.1 HT-29 human colon cancer cells ($3 \times 10^6$ cells in 100 μl of PBS) were subcutaneously injected into the right flank of 6-7 weeks old female CD-1 nude mice. After the size of tumour reached an approximate volume of 50 mm$^3$, 4 days post tumour cell injection, mitomycin C was administered by bolus infusion into the tail vein at days 4, 11 and 18 with a dose of 3.5 mg/kg/week. Antitumour effect of mitomycin C was further compared to that of SEQ ID NO:1 in combination with mitomycin C. SEQ ID NO:1 was administered by bolus infusion into the tail vein every day at 6 mg/kg and mitomycin C was administered intravenously at days 4, 11 and 18 with a dose of 3.5 mg/kg/week, one hour after the treatments with SEQ ID NO:1. Control animals received saline alone for the same period as SEQ ID NO:1. All treatments were stopped at day 22. A day after the last treatment, tumours were excised from the animals and their weights were measured. A standard bar graph was used to demonstrate the differences in tumour weights with each bar representing mean tumour weight calculated from 5 animals. As illustrated, mitomycin C treatments resulted in significant delay of tumour growth compared to saline control. The antitumour effects elicited by the combination of SEQ ID NO:1 and mitomycin C were more potent than those obtained using mitomycin C alone (see FIG. 1).

Figure 2:
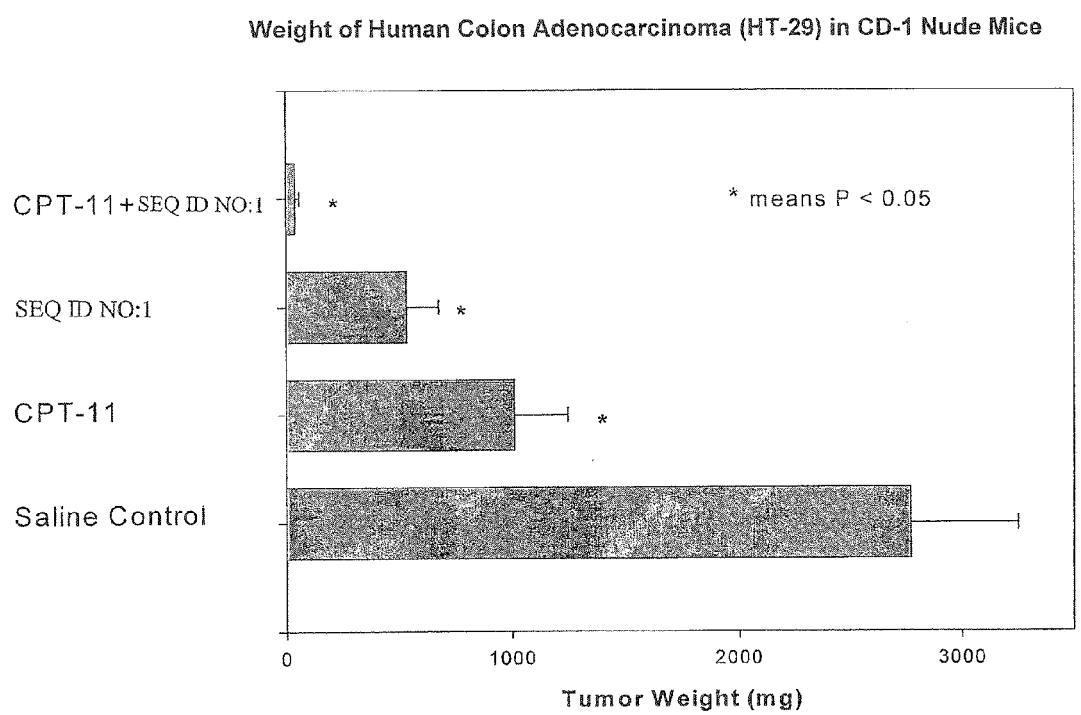
FIG. 2 depicts effects of combination therapy on HT-29 colon tumour growth in nude mice.

1.2 HT-29 human colon cancer cells ($3 \times 10^6$ cells in 100 μl of PBS) were subcutaneously injected into the right flank of 5-6 week old female CD-1 nude mice. After the size of tumour reached an approximate volume of 100 mm$^3$, 7 days post tumour cell injection, SEQ ID NO:1 was administered by bolus infusion into the tail vein every other day at 10 mg/kg. Control animals received saline alone for the same period. Antitumour effect of SEQ ID NO:1 was further compared to that of CPT-11 alone or that of SEQ ID NO:1 in combination with CPT-11. CPT-11 was administered intraperitoneally for 5 days in a row from day 7-12 with a dose of 20 mg/kg in 100 μl saline. All treatments were stopped at day 32. A day after the last treatment, tumours were excised from the animals and their weights were measured. A standard bar graph was used to demonstrate the differences in tumour weights with each bar representing mean tumour weight calculated from 9 animals. As illustrated, SEQ ID NO:1 treatments resulted in significant delay of tumour growth compared to saline control. The delay in tumour growth achieved with SEQ ID NO:1 was superior to the inhibitory effects observed with CPT-11 alone. The combination treatments of SEQ ID NO:1 and CPT-11 showed excellent cooperative effects that were more potent than either agent alone (see FIG. 2).

1.3 Caki-1 human renal cancer cells ($1 \times 10^7$ cells in 100 μl of PBS) were subcutaneously injected into the right flank of 6-7 weeks old female SCID mice. After the size of tumour reached an approximate volume of 200 mm$^3$, 7 days post tumour cell injection, SEQ ID NO:1 was administered by bolus infusion into the tail vein every other day at 10 mg/kg. Control animals received saline alone for the same period. The antitumour effect of SEQ ID NO:1 was further compared to that of two chemotherapeutic agents: 5-FU and vinblastin. 5-FU was administered intraperitoneally at days 7-13, 21-27 and 35-36 with a dose of 13 mg/kg/day, while vinblastin was administered intraperitoneally at days 7, 14, 21, 28 and 35 at a dose of 0.6 mg/kg/week. Antitumour effects of each of these compounds were further compared to those of SEQ ID NO:1 in combination with 5-FU or with vinblastin. The two chemotherapeutic agents were applied as described above, one hour after the treatments with SEQ ID NO:1 when combination treatments occurred on the same day. All treatments were stopped at day 36. A day after the last treatment, tumours were excised from the animals and their weights were measured. A standard bar graph was used to demonstrate the differences in tumour weights with each bar representing mean tumour weight calculated from 5 animals. As illustrated, SEQ ID NO:1 treatments resulted in significant delay of tumour growth compared to saline control. The delay in tumour growth achieved with SEQ ID NO:1 was superior to the inhibitory effects observed with each of two chemotherapeutic compounds. The combination of SEQ ID NO:1 with 5-FU or vinblastine was more effective than either agent alone (see FIG. 3A).

In a separate experiment, the effect of SEQ ID NO:1 in combination with IL-2 was assessed. Caki-1 human kidney cancer cells ($1\times10^7$ cells in 100 µl of PBS) were subcutaneously injected into the right flank of 6-7 weeks old female SCID mice. After the size of tumour reached an approximate volume of 100 mm$^3$, 7 days post tumour cell injection, SEQ ID NO:1 and IL2 were administered as outlined below. Control animals received saline alone for the same period.

Treatment:
1. Saline treated group: saline 0.1 ml/mouse/48 hours, i. v. n=10
2. SEQ ID NO:1 treated group: 10 mg/kg/48 hours in 0.1 ml saline, i. v., n=10 (17 treatments total)
3. IL2 treatment cycle: 8 days (treated for 4 days, untreated for 2 days then treated for another 4 days)
   I-High Dose (20000 unit)/2 times for one day treatment i.p. n=10
   II-Low Dose (5000 unit)/2 times for one day treatment i.p. n=10
4. SEQ ID NO:1+IL-2 treated group-I (2+3) n=10
5. SEQ ID NO:1+IL-2 treated group-II (2+4) n=10

Figure 3:
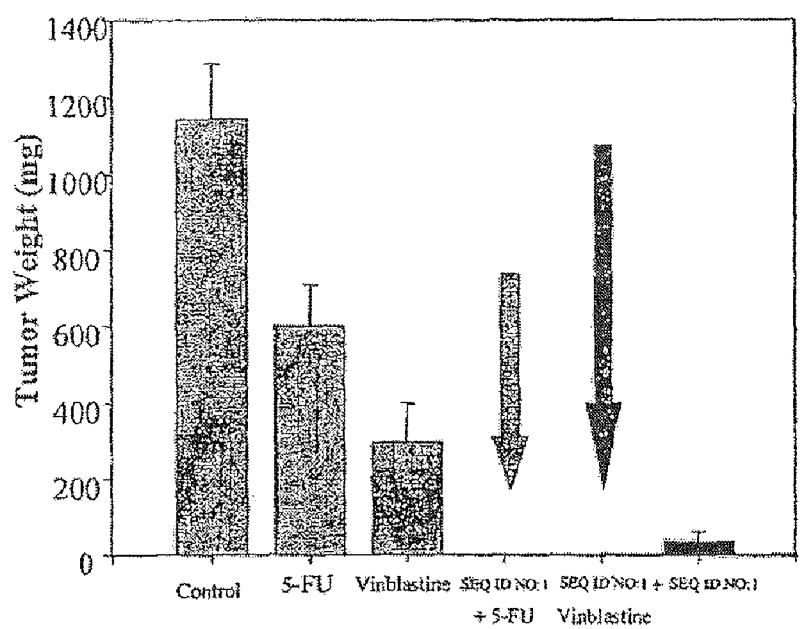
FIG. 3 depicts effects of combination therapy on Caki-1 renal tumour growth in SCID mice.
Figure 3:
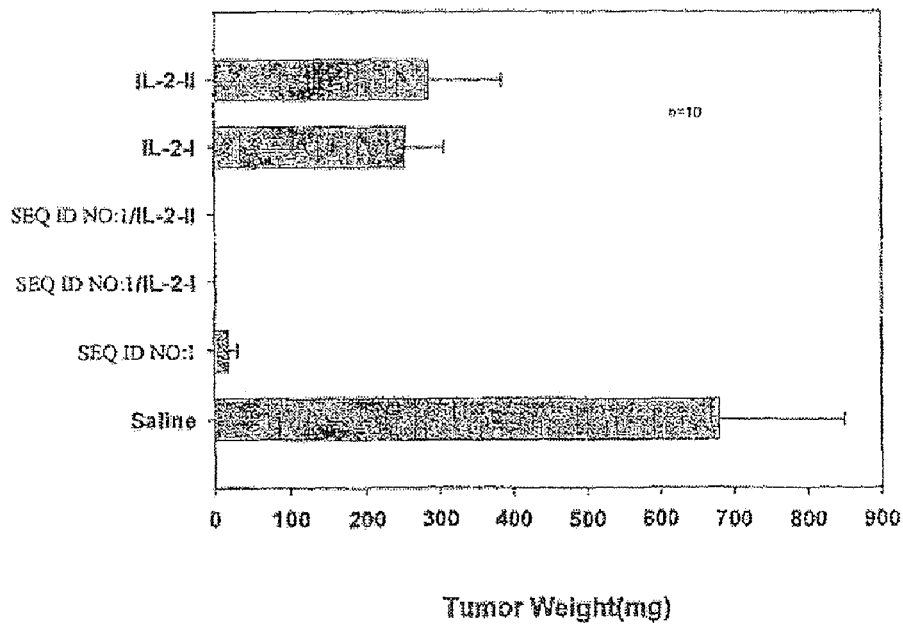

After 52 days the mice were sacrificed and the tumours weighed. The results are shown in FIG. 3B. Each bar represents the mean tumour weight and standard error calculated for each treatment group.

Figure 4:
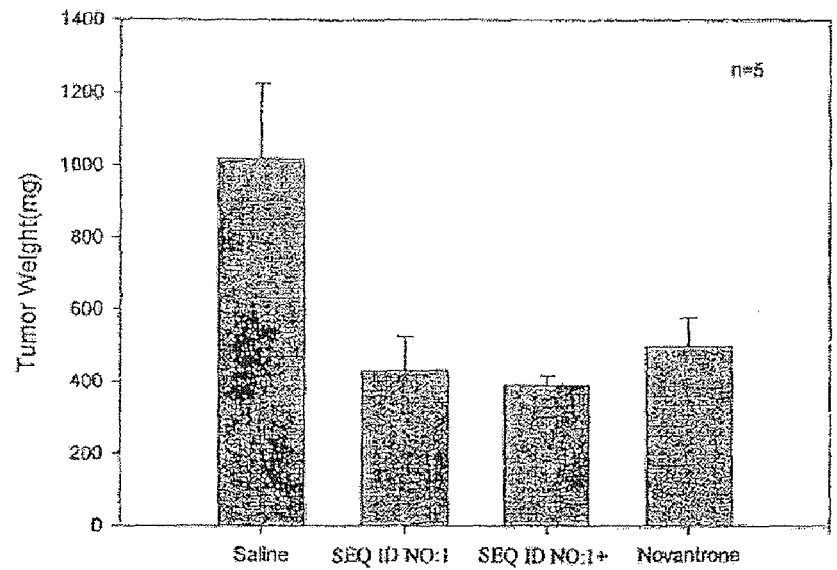
FIG. 4 depicts effects of combination therapy on prostatic tumour growth in SCID mice.
Figure 4:
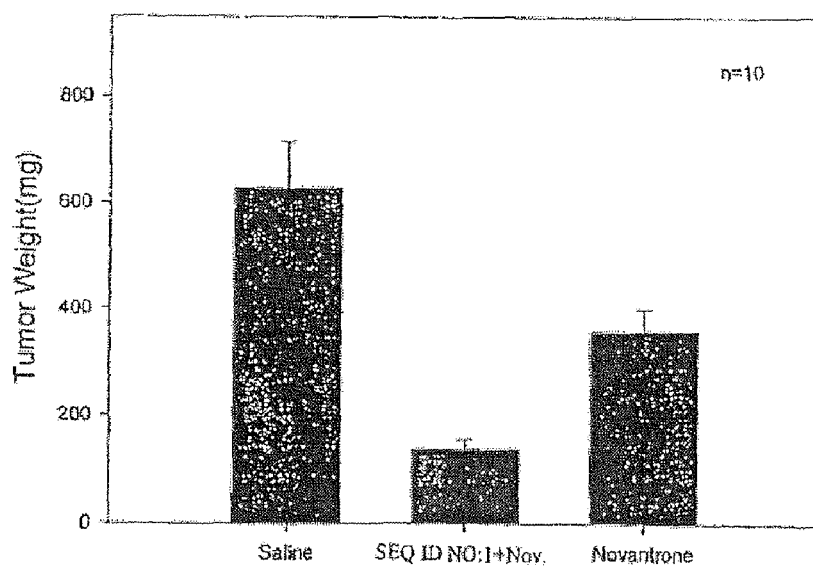

1.4 FIG. 4 shows results from two independent experiments. In both experiments, PC-3 human prostatic cancer cells ($1\times10^7$ cells in 100 µl of PBS) were subcutaneously injected into the right flank of 6-7 weeks old male SCID mice. After the size of tumour reached an approximate volume of 50 mm$^3$, 14 days post tumour cell injection, SEQ ID NO: 1 was administered by bolus infusion into the tail vein every other day at 10 mg/kg 18 times (FIG. 4A) or 17 times (FIG. 4B), respectively. Control animals received saline alone for the same period. Antitumour effect of SEQ ID NO:1 was further compared to that of mitoxantrone (novantrone) alone or in combination. Mitoxantrone was administered intravenously once at the beginning of the treatments at a dose of 2 mg/kg (FIG. 4A) or once a week for four weeks at a reduced dose of 0.8 mg/kg (FIG. 4B). All treatments were stopped at day 50 (FIG. 4A) or 48 (FIG. 4B), respectively. A day after the last treatment, tumours were excised from the animals and their weights were measured. A standard bar graph was used to demonstrate the differences in tumour weights with each bar representing mean tumour weight calculated from 5 (FIG. 4A) or 10 (FIG. 4B) animals. As illustrated in FIG. 4A, SEQ ID NO:1 treatments resulted in significant delay of tumour growth compared to saline control. The delay in tumour growth achieved with SEQ ID NO:1 was similar to the inhibitory effects observed with mitoxantrone alone. The combination of SEQ ID NO:1 with mitoxantrone (SEQ ID NO: 1+) showed some additive antitumour effects. FIG. 4B shows mitoxantrone alone resulted in significant delay of tumour growth and the combination therapy was more potent than mitoxantrone monotherapy.

Figure 5:
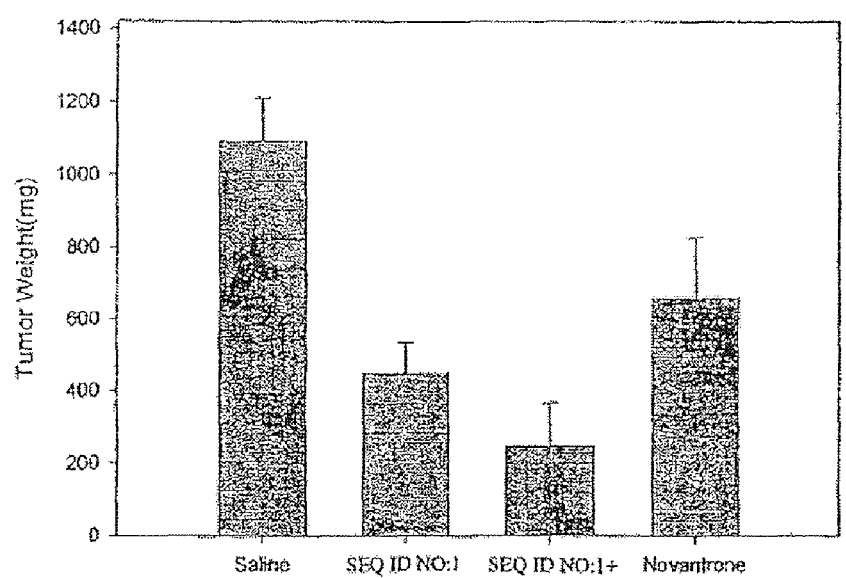
FIG. 5 depicts effects of combination therapy on prostatic tumour growth in SCID mice.
Figure 5:
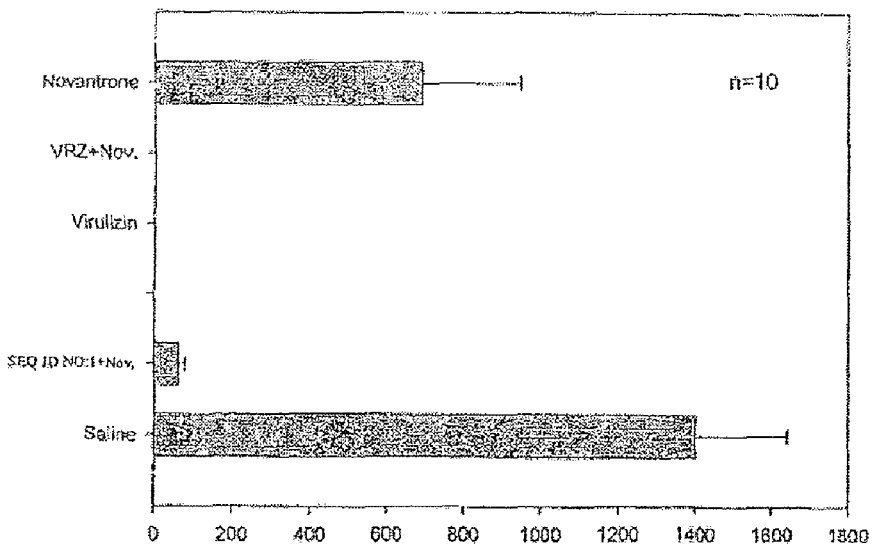

1.5 FIG. 5 shows results from two independent experiments. In both experiments, DU145 human prostatic cancer cells ($1\times10^7$ cells in 100 µl of PBS) were subcutaneously injected into the right flank of 6-7 weeks old male SCID mice. After the size of tumour reached an approximate volume of 50 mm$^3$, 13 (FIG. 5A) or 11 (FIG. 5B) days post tumour cell injection, SEQ ID NO:1 was administered by bolus infusion into the tail vein every other day at 10 mg/kg 15 times (FIG. 5A) or 14 times (FIG. 5B), respectively. Control animals received saline alone for the same period. Antitumour effect of SEQ ID NO:1 was further compared to that of mitoxantrone (novantrone) alone or in combination. Mitoxantrone was administered intravenously once at the beginning of the treatments at a dose of 2 mg/kg (FIG. 5A) or once a week for four weeks at a reduced dose of 0.8 mg/kg (FIG. 5B). All treatments were stopped at day 42 (FIG. 5A) or 38 (FIG. 5B), respectively. A day after the last treatment, tumours were excised from the animals and their weights were measured. A standard bar graph was used to demonstrate the differences in tumour weights with each bar representing mean tumour weight calculated from 5 (FIG. 5A) or 10 (FIG. 5B) animals. As illustrated in FIG. 5A, SEQ ID NO:1 treatments resulted in significant delay of tumour growth compared to saline control. The delay in tumour growth achieved with SEQ ID NO:1 was similar to the inhibitory effects observed with mitoxantrone alone. The combination of SEQ ID NO:1 with mitoxantrone (SEQ ID NO: 1+) showed some additive antitumour effects. In FIG. 5B, mitoxantrone alone resulted in significant delay of tumour growth and the combination therapy was more potent than mitoxantrone monotherapy.

Figure 6:
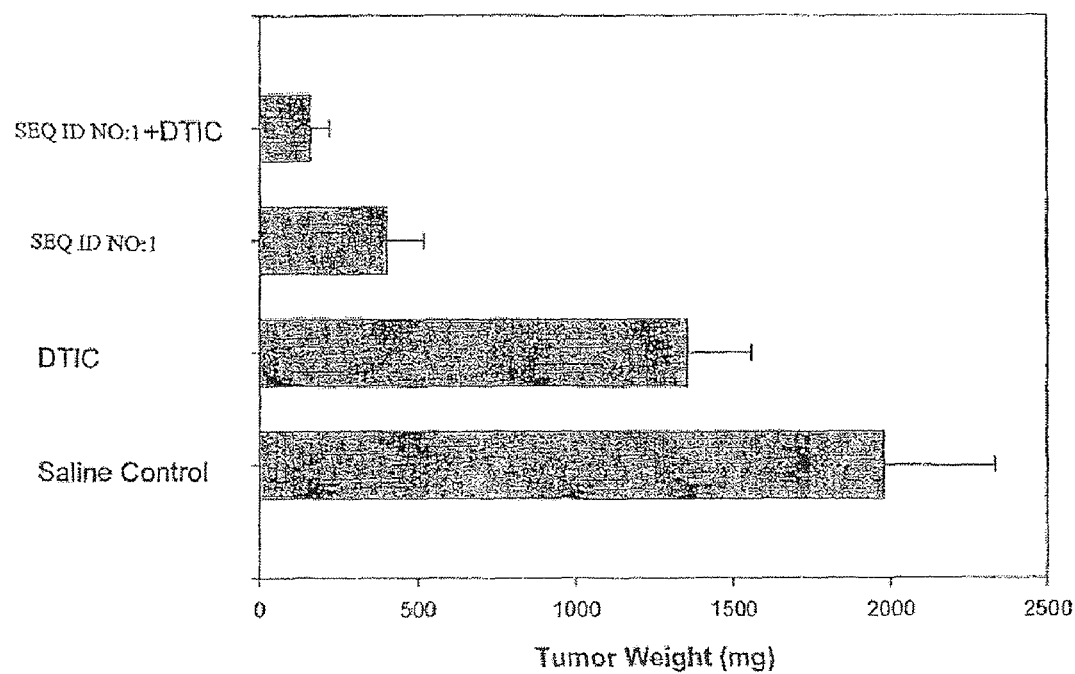
FIG. 6 depicts effects of combination therapy on A2058 melanoma growth in nude mice.

1.6 A2058 human melanoma cells ($1\times10^7$ cells in 100 µl of PBS) were subcutaneously injected into the right flank of 6-7 week old female CD-1 nude mice. A2058 is a metastatic melanoma cell line. After the size of tumour reached an approximate volume of 100 mm$^3$, 6 days post tumour cell injection, SEQ ID NO:1 was administered by bolus infusion into the tail vein every other day at 10 mg/kg. Control animals received saline alone for the same period. Antitumour effect of SEQ ID NO:1 was further compared to that of dacarbazine (DTIC) alone or that of SEQ ID NO:1 in combination with DTIC. DTIC was administered intravenously for 5 days in a row from day 6-10 at a dose of 80 mg/kg in 100 µl saline. All treatments were stopped at day 24. A day after the last treatment, tumours were excised from the animals and their weights were measured. A standard bar graph was used to demonstrate the differences in tumour weights with each bar representing mean tumour weight calculated from 10 animals. As illustrated, SEQ ID NO:1 treatments resulted in significant delay of tumour growth compared to saline control. The delay in tumour growth achieved with SEQ ID NO:1 was superior to the inhibitory effects observed with DTIC alone. The combination of SEQ ID NO:1 and DTIC was more potent than either agent alone (FIG. 6).

Figure 7:
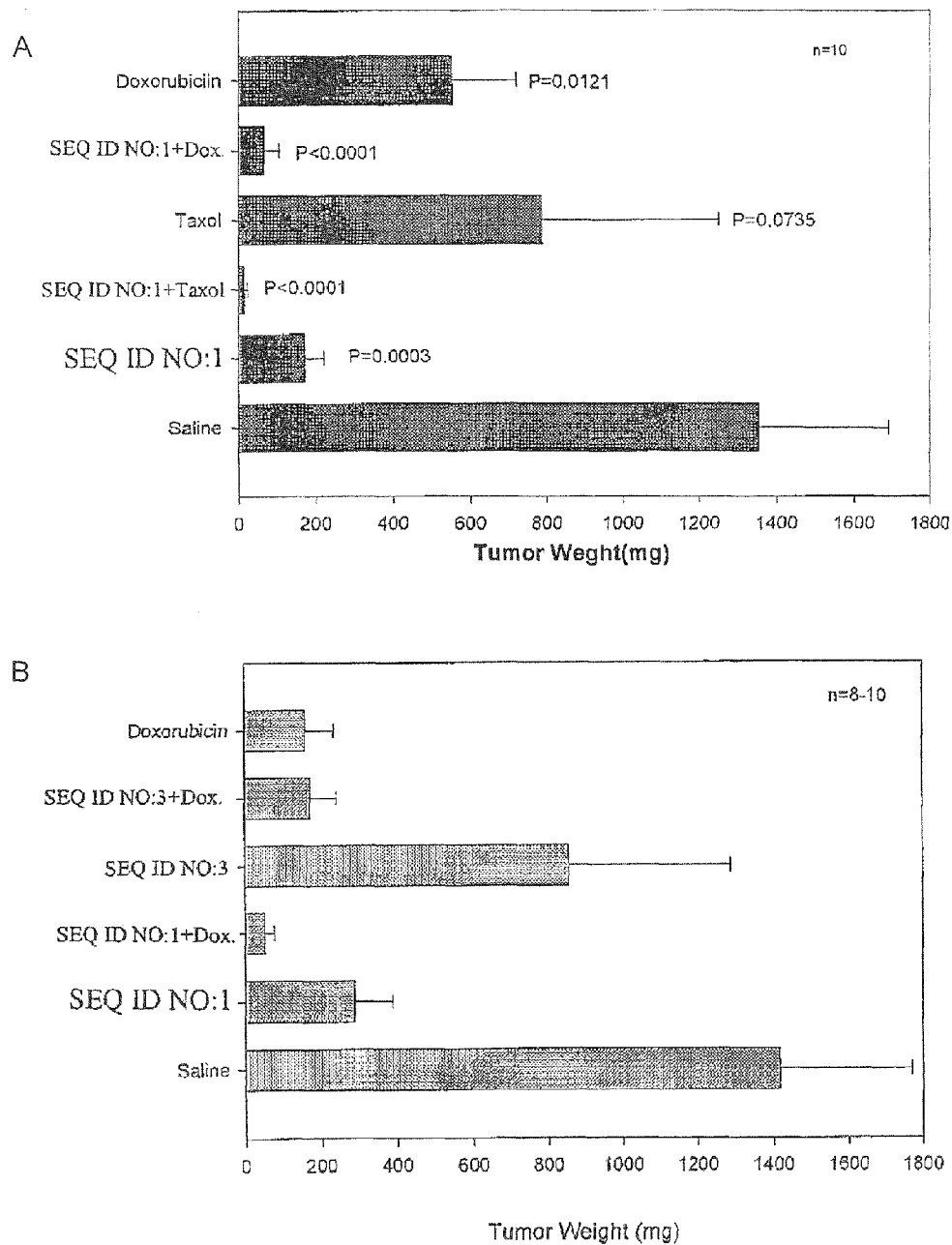
FIG. 7 depicts effects of combination therapy on breast tumour growth in CD-1 nude mice.
Figure 7:
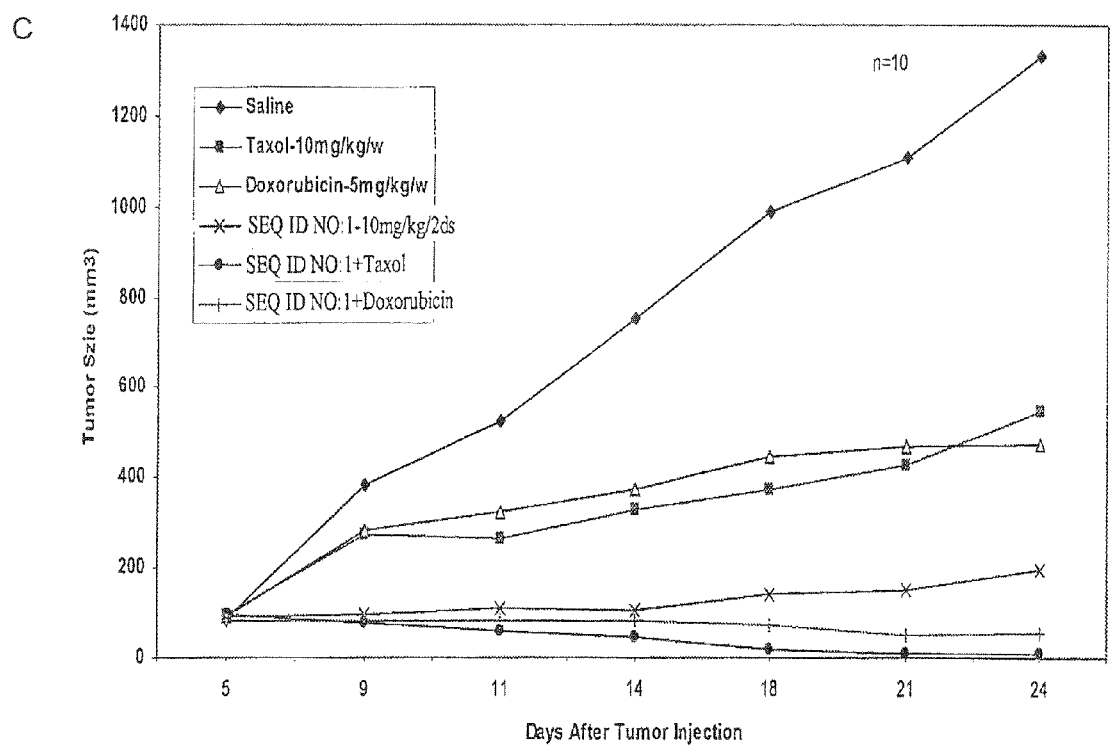

1.7 FIG. 7 shows results from three independent experiments. MDA-MB-231 human breast cancer cells ($1\times10^7$ cells in 100 µl of PBS) were subcutaneously injected into the right flank of 6-7 weeks old female CD-1 nude mice. After the size of tumour reached an approximate volume of 100 mm³, 5 days post tumour cell injection, SEQ ID NO:1, or the scrambled control oligonucleotide (SEQ ID NO:3) were administered by bolus infusion into the tail vein every other day at 10 mg/kg. Control animals received saline alone for the same period. Antitumour effect of SEQ ID NO:1 was further compared to that of taxol or doxorubicin alone or in combination. Taxol was administered intravenously once a week at a dose of 10 mg/kg for three (FIG. 7A) or four weeks (FIG. 7C). Doxorubicin was administered intravenously once a week at a dose of 5 mg/kg for first three weeks (FIG. 7A) or for two weeks (FIG. 7C). All treatments were stopped at day 33 (FIG. 7A) or at day 26 (FIG. 7C), respectively. A day after the last treatment, tumours were excised from the animals and their weights were measured. A standard bar graph was used to demonstrate the differences in tumour weights with each bar representing mean tumour weight calculated from 10 animals (FIGS. 7A &7B). In FIG. 7C, antitumour activities were estimated by the inhibition of tumour volume, which was measured with calipers. Each point represents mean tumour volume calculated from 10 animals per experimental group. As illustrated, SEQ ID NO:1 treatments resulted in a delay of tumour growth compared to saline control in all three experiments. The delay in tumour growth achieved with SEQ ID NO:1 was superior to the inhibitory effects observed with taxol or doxorubicin alone. The combination therapy of SEQ ID NO:1 with taxol or doxorubicin was more potent than either monotherapy. FIG. 7B demonstrates that a control oligonucleotide that has the same base composition as SEQ ID NO:1, but is not complementary to R2 mRNA has no significant anti-tumour activity as a monotherapy and does not cooperate with doxorubicin, suggesting that the effects of SEQ ID NO:1 are sequence specific.

Figure 8:
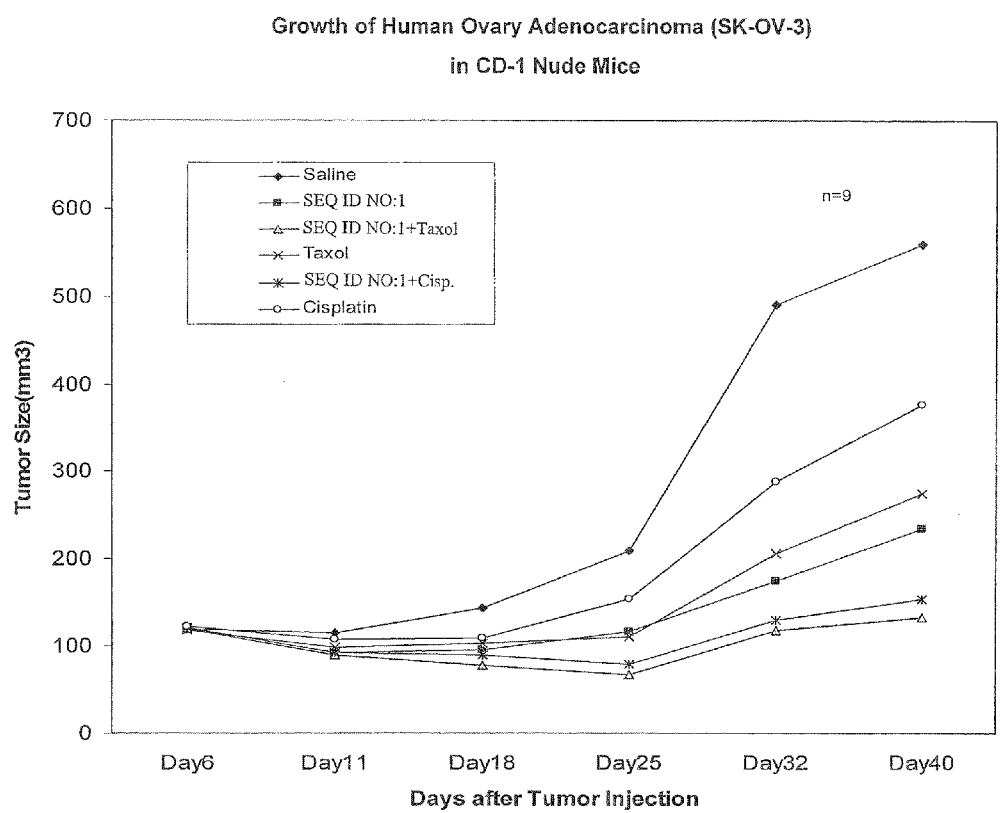
FIG. 8 depicts effects of combination therapy on ovary tumour growth in CD-1 nude mice.

1.8 SK-OV-3 human ovary adenocarcinoma cells (1×10⁷ cells in 100 µl of PBS) were subcutaneously injected into the right flank of 6-7 weeks old female CD-1 nude mice. After the size of tumour reached an approximate volume of 100 mm³, 6 days post tumour cell injection, SEQ ID NO: 1 was administered by bolus infusion into the tail vein every other day at 10 mg/kg 17 times. Control animals received saline alone for the same period. Antitumour effect of SEQ ID NO: 1 was further compared to that of taxol or cisplatin alone or in combination. Taxol was administered intravenously once a week for first three weeks and intraperitoneally once a week for next two weeks at a dose of 10 mg/kg. Cisplatin was administered intravenously once a week for first three weeks and intraperitoneally once a week for next two weeks at a dose of 4 mg/kg. All treatments were stopped at day 40. Antitumour activities were estimated by the inhibition of tumour volume, which was measured with caliper. Each point represents mean tumour volume calculated from 9 animals per experimental group. As illustrated, SEQ ID NO:1 treatments resulted in significant delay of tumour growth compared to saline control. The delay in tumour growth achieved with SEQ ID NO:1 was similar or superior to the inhibitory effects observed with taxol or cisplatin alone, respectively. The combination therapy of SEQ ID NO:1 with taxol or cisplatin was more potent than either monotherapy (FIG. 8).

Results of SEQ ID NO:1 treatment in combination with various chemotherapeutics are summarised in Table 3.

TABLE 3

Summary of SEQ ID NO: 1 Treatment in Combination with Standard Chemotherapy Drugs

| Tumour | Mouse | Treatment | Tumour weight as % of saline control | |
|---|---|---|---|---|
| Caki (renal) | CD-1 | SEQ ID NO: 1 | 3.3 | |
| | | 5-FU | 52 | |
| | | Vinblastine | 26 | |
| | | SEQ ID NO: 1 + 5-FU | 0 | |
| | | SEQ ID NO: 1 + Vinblastine | 0 | |
| HT-29 (colon) | SCID | Mitomycin C | 15 | |
| | | SEQ ID NO: 1 + Mitomycin C | 0.8 | |
| HT-29 (colon) | CD-1 | SEQ ID NO: 1 | 19 | |
| | | CPT-11 | 36 | |
| | | SEQ ID NO: 1 + CPT-11 | 1.4 | |
| MDA-MB-231 (breast) | CD-1 | SEQ ID NO: 1 | 12.6 | |
| | | Taxol | 58 | |
| | | Doxorubicin | 41 | |
| | | SEQ ID NO: 1 + Taxol | 1 | |
| | | SEQ ID NO: 1 + Doxorubicin | 4.8 | |
| A2058 (melanoma) | CD-1 | SEQ ID NO: 1 | 20 | |
| | | DTIC | 68 | |
| | | SEQ ID NO: 1 + DTIC | 8 | |
| PC-3 (prostatic) | SCID | Novantrone | 57 | |
| | | SEQ ID NO: 1 + Novantrone | 21 | |
| DU145 (prostatic) | SCID | SEQ ID NO: 1 | n.a. | 41 |
| | | Novantrone | 40 | 60 |
| | | SEQ ID NO: 1 + Novantrone | 4.6 | 23 |
| **SK-OV-3 (ovary) | CD-1 | SEQ ID NO: 1 | 42 | |
| | | Taxol | 49 | |
| | | Cisplatin | 67 | |
| | | SEQ ID NO: 1 + Taxol | 24 | |
| | | SEQ ID NO: 1 + Cisplatin | 27 | |

Results shown are mean tumour weights presented as a percentage of saline treated controls.
**is tumour volume data as percentage of saline control.

Example 2

Figure 9:
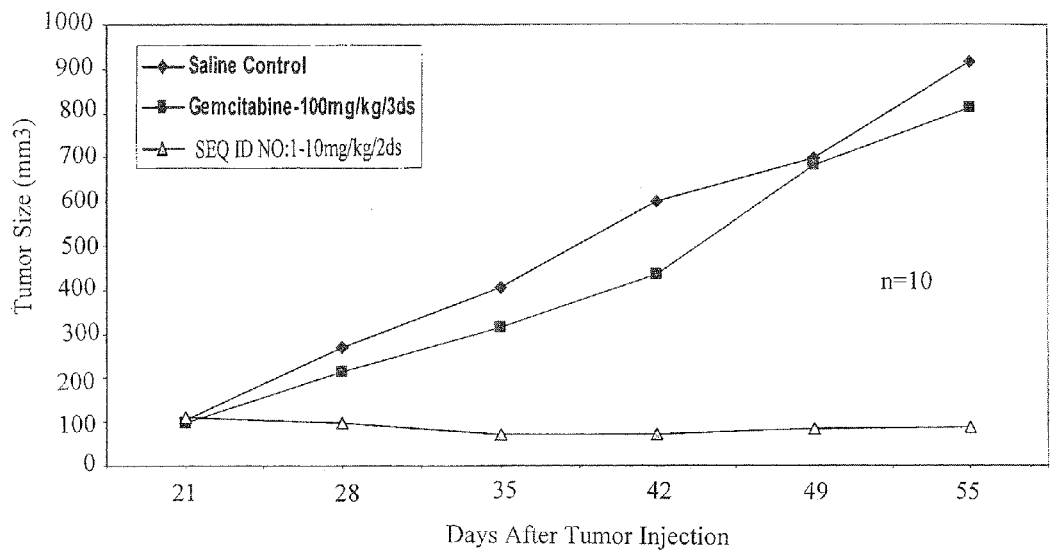
FIG. 9 depicts effects of SEQ ID NO: 1 in the treatment of human pancreatic carcinoma in CD-1 nude mice.
Figure 9:
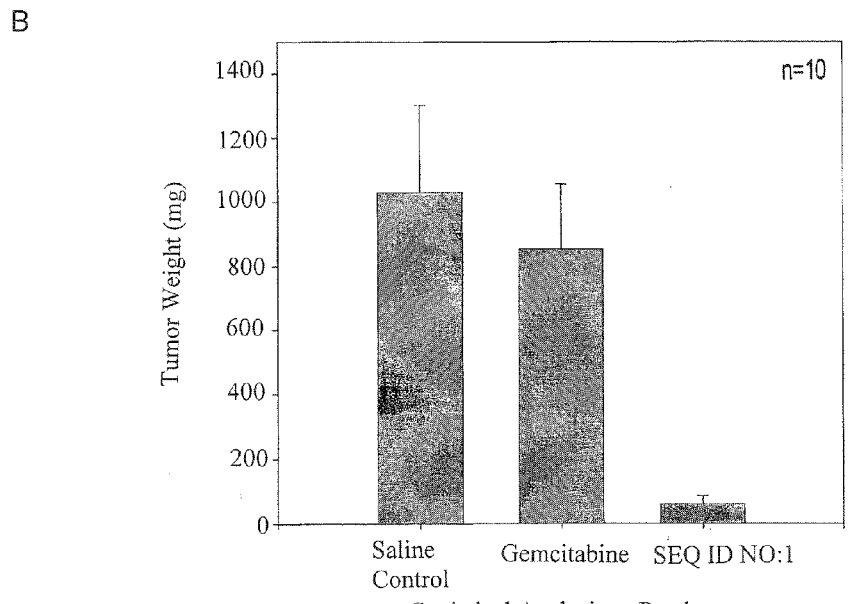

In vivo Testing of SEQ ID NO:1 Alone or in Combination with Various Chemotherapeutics in Drug-Resistant Tumours 2.1 BxPC-3 human pancreatic carcinoma cells (3×10⁶ cells in 100 µl of PBS) were subcutaneously injected into the right flank of 6-7 weeks old female CD-1 nude mice. BxPC-3 is a gemcitabine resistant call line. After the size of tumour reached an approximate volume of 100 mm³, 21 days post tumour cell injection, SEQ ID NO: 1 was administered by bolus infusion into the tail vein every other day at 10 mg/kg 17 times. Control animals received saline alone for the same period. Antitumour effect of SEQ ID NO: 1 was further compared to that of Gemcitabine. Gemcitabine was administered intravenously every three days at a dose of 100 mg/kg. Antitumour activities were estimated by the inhibition of tumour volume, which was measured with caliper. Each point represents mean tumour volume calculated from 10 animals per experimental group. As illustrated, SEQ ID NO: 1 treatments resulted in significant delay of tumour growth compared to saline control. As expected, treatment with Gemcitabine during the same period was ineffective against Gemcitabine-resistant tumour (FIGS. 9A & B).

Figure 10:
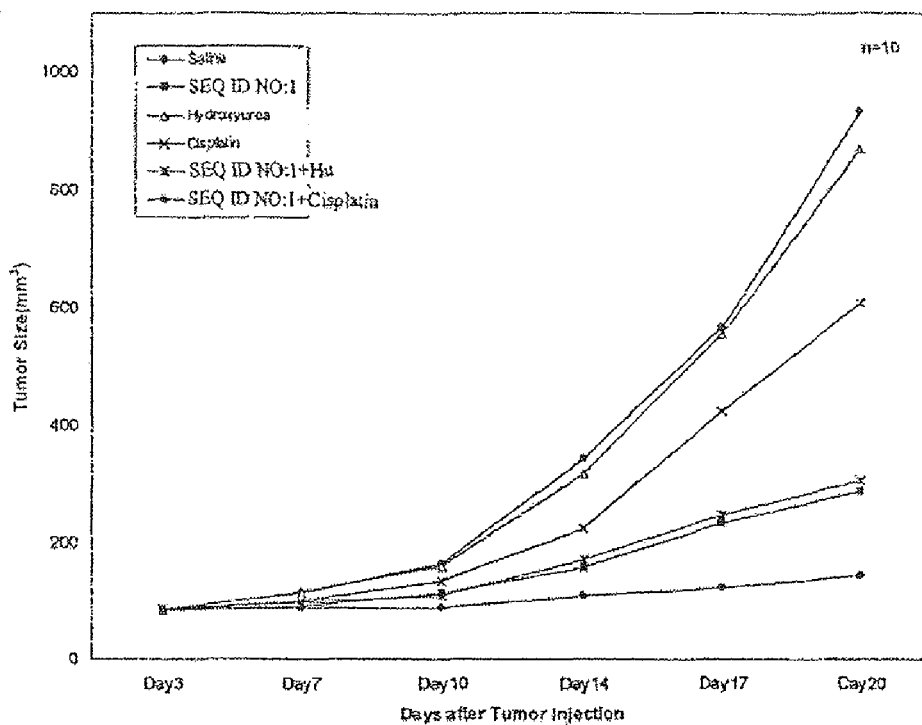
FIG. 10 depicts effects of SEQ ID NO: 1 in the treatment of human cervix epitheloid carcinoma resistant to hydroxyurea (HU) in SCID mice.
Figure 10:
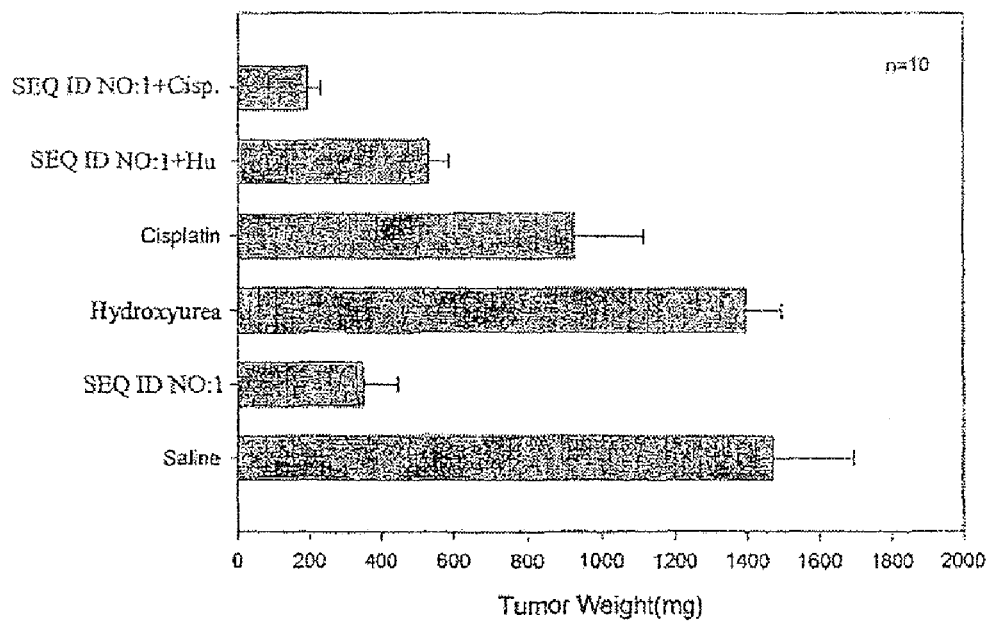

2.1 Hela S3 human cervix epitheloid carcinoma cells (5×10⁵ cells in 100 µl of PBS) were subcutaneously injected into the right flank of 6-7 weeks old female SCID mice. Hela S3 is a hydroxyurea resistant cell line. After the size of tumour reached an approximate volume of 100 mm$^3$, 3 days post tumour cell injection, SEQ ID NO:1 was administered by bolus infusion into the tail vein every other day at 10 mg/kg 6 times. Control animals received saline alone for the same period. Antitumour effect of SEQ ID NO:1 was further compared to that of Hydroxyurea or Cisplatin alone or in combination. Hydroxyurea was administered intraperitoneally every day at a dose of 250 mg/kg for 10 days. Cisplatin was administered intravenously once a week for three weeks at a dose of 4 mg/kg. Antitumour activities were estimated by the inhibition of tumour volume, which was measured with caliper. Each point represents mean tumour volume calculated from 10 animals per experimental group. As illustrated, SEQ ID NO:1 treatments resulted in significant delay of tumour growth compared to saline control. As expected, treatment with Hydroxyurea during the same period was ineffective against Hydroxyurea-resistant tumour. The delay in tumour growth achieved with SEQ ID NO:1 was superior to the inhibitory effects observed with Cisplatin alone, which was used as a positive control. The combination therapy of SEQ ID NO:1 with Hydroxyurea was only as effective as SEQ ID NO:1 monotherapy, as expected. The combination therapy of SEQ ID NO:1 with Cisplatin, however, was more potent than either monotherapy (FIGS. 10A & B).

Figure 11:
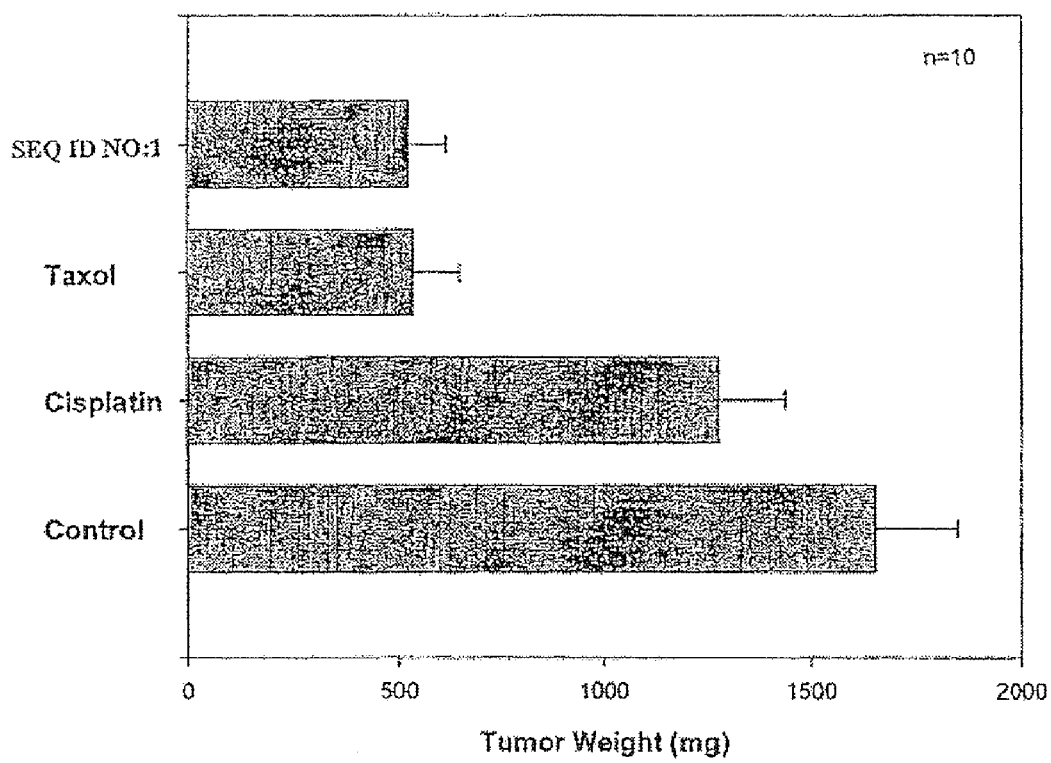
FIG. 11 depicts effects of SEQ ID NO: 1 in the treatment of human breast adenocarcinoma resistant to cisplatin in SCID mice.

2.3 MDA-CDDP-S4 human in vivo-selected Cisplatin-resistant breast adenocarcinoma cells (4×10$^6$ cells in 100 μl of PBS) were injected into the fat pad (inside of right leg) of 6-7 weeks old female SCID mice. After the size of tumour reached an approximate volume of 100 mm$^3$, 7 days post tumour cell injection, SEQ ID NO: 1 was administered by bolus infusion into the tail vein every other day at 10 mg/kg 9 times. Control animals received saline alone for the same period. Antitumour effect of SEQ ID NO: 1 was further compared to that of Cisplatin or Taxol alone. Cisplatin was administered intravenously once a week for three weeks at a dose of 4 mg/kg. Taxol was administered intravenously once a week for three weeks at a dose of 10 mg/kg. Antitumour activities were estimated by the inhibition of tumour volume, which was measured with caliper. Each point represents mean tumour volume calculated from 10 animals per experimental group. As illustrated, SEQ ID NO: 1 treatments caused significant reduction of tumour weight compared to saline control. As expected, treatment with Cisplatin during the same period was ineffective against Cisplatin-resistant tumour. The delay in tumour growth achieved with SEQ ID NO: 1 was similar to the inhibitory effects observed with Taxol, which was used as a positive control (FIG. 11).

Figure 12:
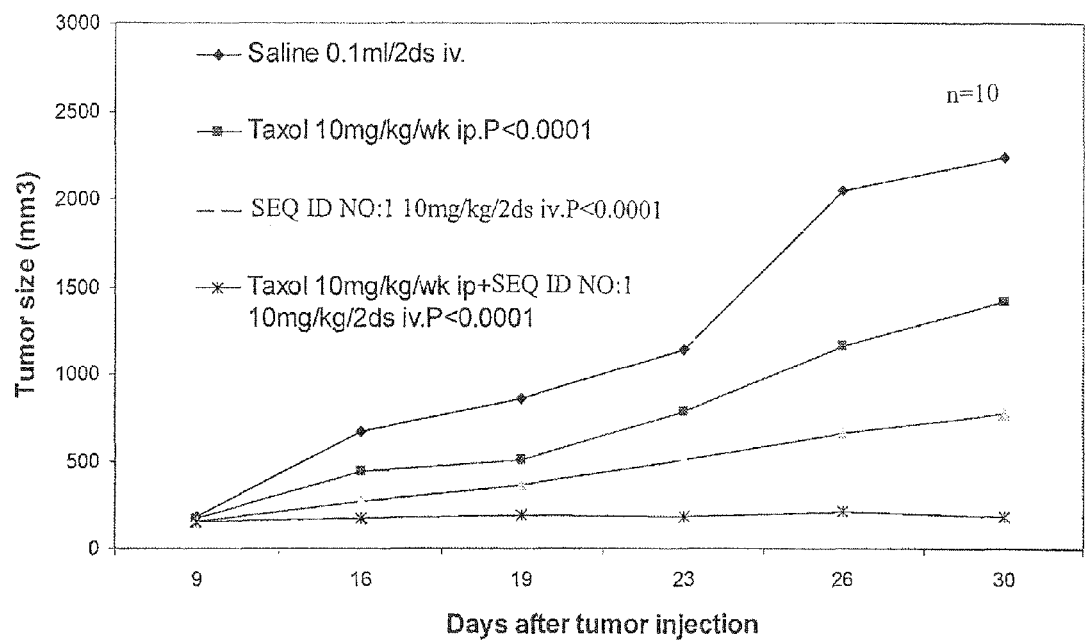
FIG. 12 depicts effects of SEQ ID NO: 1 in the treatment of human breast adenocarcinoma resistant to cisplatin in SCID mice.
Figure 12:
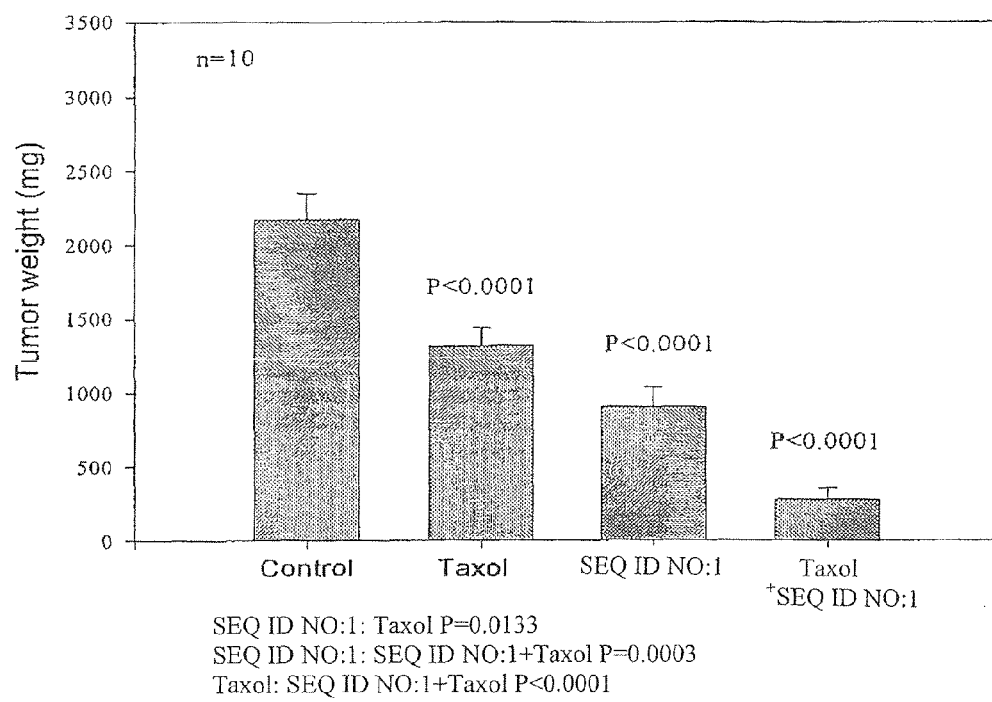
Figure 12:
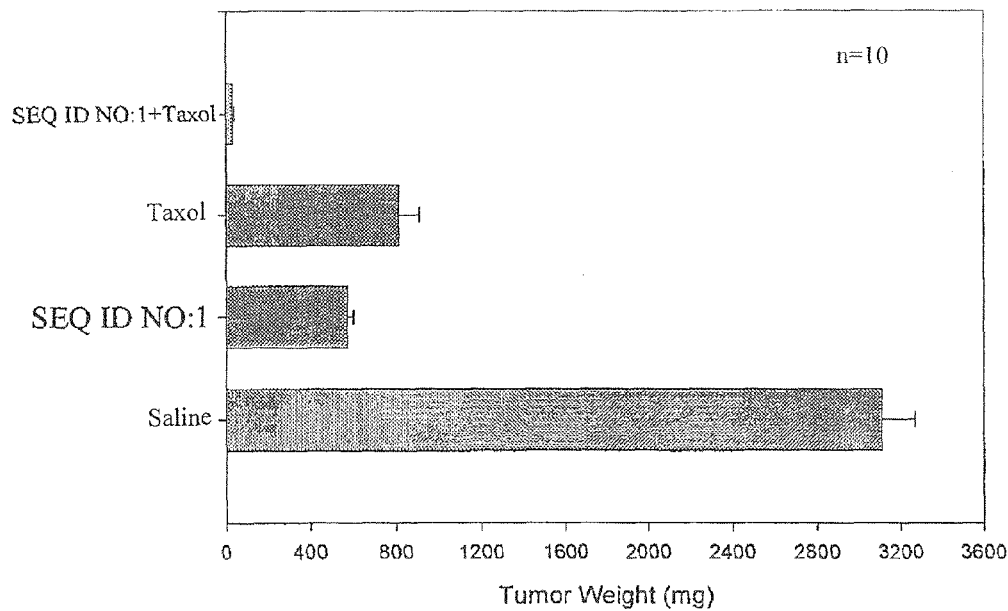

2.4 MDA-CDDP-S4 human in vivo-selected Cisplatin-resistant breast adenocarcinoma cells (4×10$^6$ cells in 100 μl of PBS) were injected into the fat pad (inside of right leg) of 6-7 weeks old female CB-17 SCID mice. After the size of tumour reached an approximate volume of 100 mm$^3$, 9 days post tumour cell injection, SEQ ID NO:1 was administered by bolus infusion into the tail vein every other day at 10 mg/kg. Control animals received saline alone for the same period. Antitumour effect of SEQ ID NO: 1 was further compared to that of Taxol alone and in combination. Taxol was administered i.p. once a week at a dose of 10 mg/kg. Antitumour activities were estimated by the inhibition of tumour volume (FIG. 12A), which was measured with calipers. Each point represents mean tumour volume calculated from 10 animals per experimental group. Animals were sacrificed and tumour weights taken at the end of the study (FIG. 12C). SEQ ID NO:1 treatments caused significant reduction of tumour weight compared to saline control. The delay in tumour growth achieved with SEQ ID NO:1 was superior to the inhibitory effects observed with Taxol, which was used as a positive control. The effects of combined treatment were greater than either treatment alone. This study was repeated with similar results (FIG. 12B).

Figure 13:
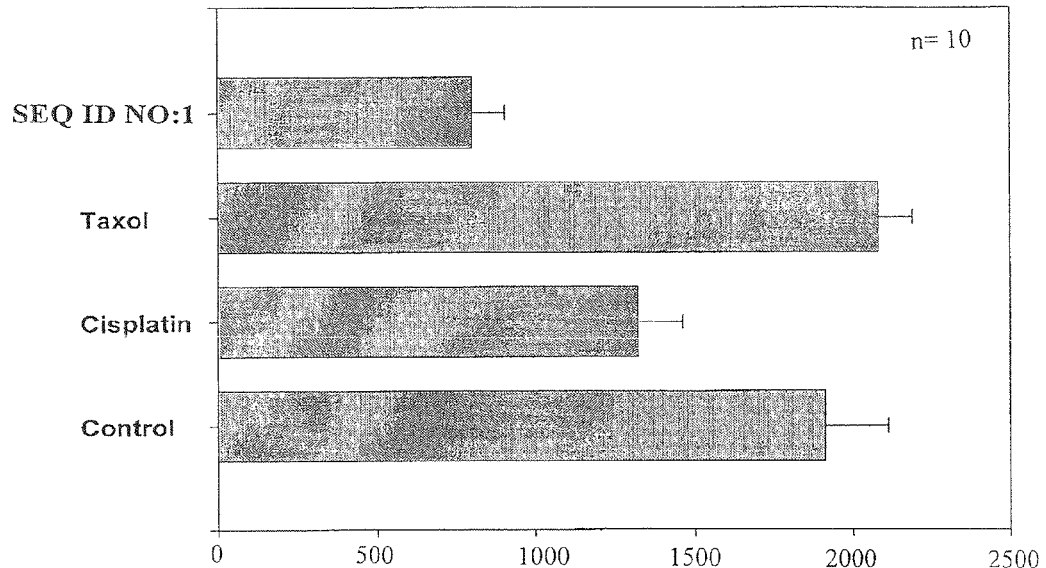
FIG. 13 depicts effects of SEQ ID NO: 1 in the treatment of human breast adenocarcinoma resistant to taxol in SCID mice.
Figure 13:
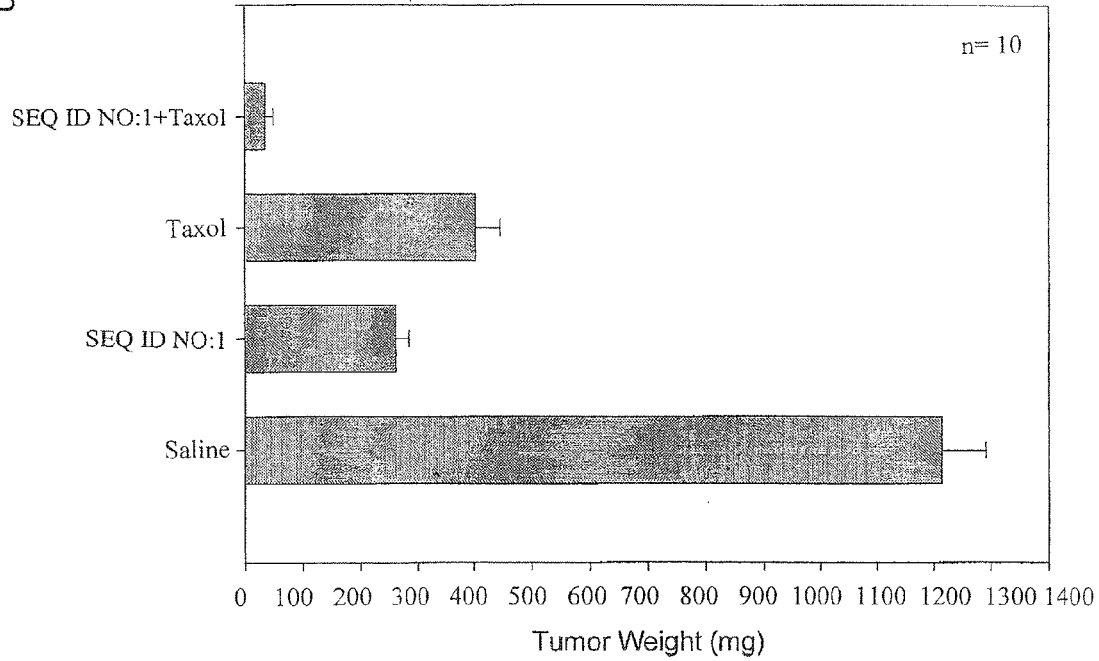

2.5 MDA-MB435-To.1 human Taxol-resistant breast adenocarcinoma cells (4×10$^6$ cells in 100 μl of PBS) were injected into the fat pad (inside of right leg) of 6-7 weeks old female SCID mice. After the size of tumour reached an approximate volume of 100 mm$^3$, 20 days post tumour cell injection, SEQ ID NO: 1 was administered by bolus infusion into the tail vein every other day at 10 mg/kg 15 times. Control animals received saline alone for the same period. Antitumour effect of SEQ ID NO: 1 was further compared to that of Cisplatin or Taxol alone. Cisplatin was administered intravenously once a week for four weeks at a dose of 4 mg/kg. Taxol was administered intravenously once a week for four weeks at a dose of 20 mg/kg. Antitumour activities were estimated by the inhibition of tumour volume, which was measured with caliper. Each point represents mean tumour volume calculated from 9-10 animals per experimental group. As illustrated, SEQ ID NO:1 treatments caused significant reduction of tumour weight compared to saline control. As expected, treatment with Taxol during the same period was ineffective against Taxol-resistant tumour. The delay in tumour growth achieved with SEQ ID NO:1 was superior to the inhibitory effects observed with Cisplatin, which was used as a positive control (see FIGS. 13A & B).

Figure 14:
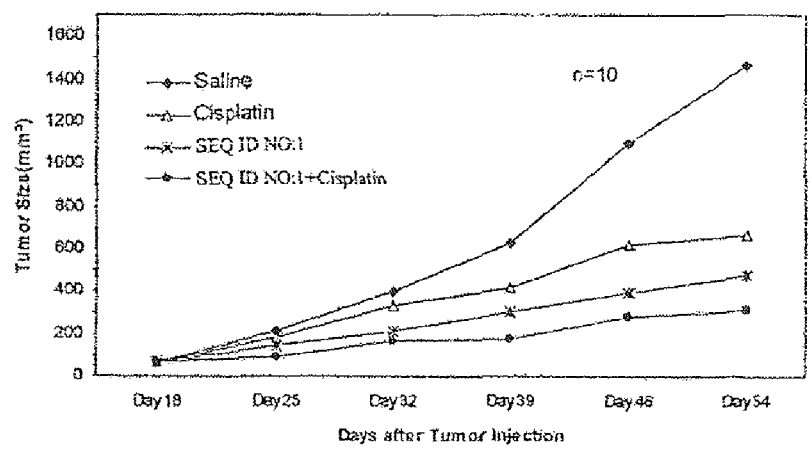
FIG. 14 depicts effects of SEQ ID NO: 1 in the treatment of human breast adenocarcinoma resistant to taxol in SCID mice.
Figure 14:
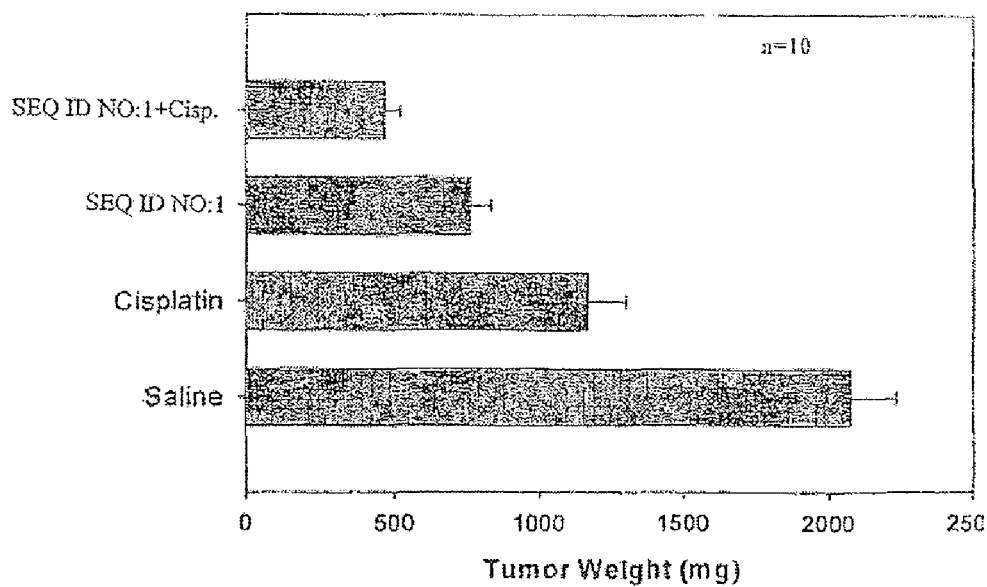

2.6 MDA-MB435-To.1 human Taxol-resistant breast adenocarcinoma cells (4×10$^6$ cells in 100 μl of PBS) were injected into the fat pad (inside of right leg) of 6-7 weeks old female CB-17 SCID mice. After the size of tumour reached an approximate volume of 100 mm$^3$, 17 days post tumour cell injection, SEQ ID NO:1 was administered by bolus infusion into the tail vein every other day at 10 mg/kg. Control animals received saline alone for the same period. Antitumour effect of SEQ ID NO: 1 was compared to that of Cisplatin alone and in combination. Cisplatin was administered intravenously once a week for four weeks at a dose of 4 mg/kg. Antitumour activities were estimated by the inhibition of tumour volume, which was measured with caliper. Each point represents mean tumour volume calculated from 10 animals per experimental group. At the end of the study the animals were sacrificed and tumours weighed. As illustrated, SEQ ID NO:1 treatment caused significant reduction of tumour weight compared to saline control. The delay in tumour growth achieved with SEQ ID NO:1 was superior to the inhibitory effects observed with Cisplatin, which was used as a positive control. The combination of the two compounds produced anti-tumour efficacy that was superior to either one alone (see FIGS. 14A & B).

Figure 15:
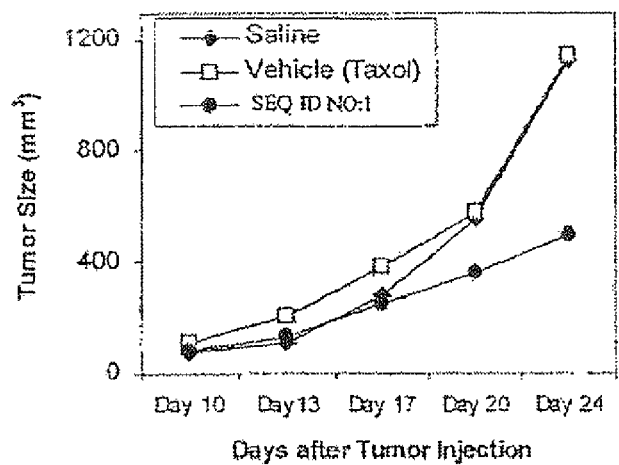
FIG. 15 depicts effects of SEQ ID NO: 1 in the treatment of human promyelocytic leukemia resistant to taxol in SCID mice.
Figure 15:
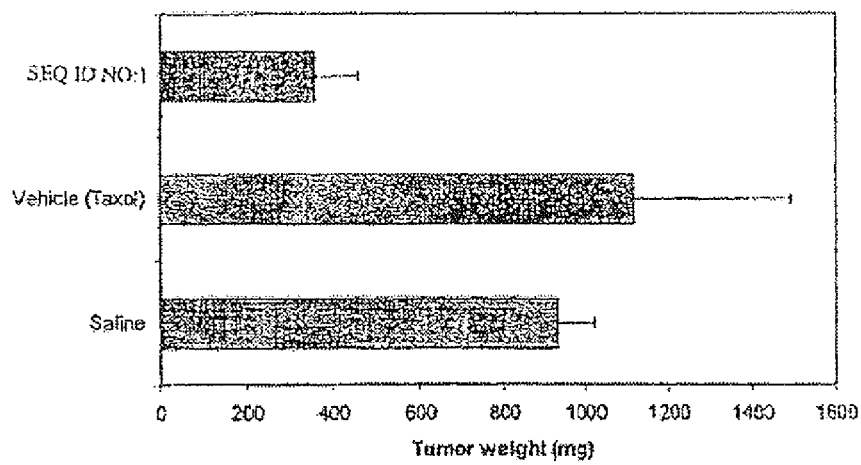

2.7 Human taxol-resistant promyelocytic leukaemia cells (HL-60) (7×10$^6$ cells in 100 μl of PBS) were injected into the right flank of 6-7 weeks old female SCID mice. After the size of tumour reached an approximate volume of 100 mm$^3$, 10 days post tumour cell injection, SEQ ID NO:1 was administered by bolus infusion into the tail vein every other day at 10 mg/kg. Control animals received saline alone for the same period. The anti-tumour effect of SEQ ID NO:1 was further compared to that of taxol. Taxol was administered i.p. once a week at a dose of 10 mg/kg. Anti-tumour activity was estimated by the inhibition of tumour volume, which was measured with caliper. Each point represents mean tumour volume calculated from 10 animals per experimental group. In addition animals were sacrificed and tumour weights taken at the end of the study. SEQ ID NO:1 treatments caused significant reduction of tumour weight compared to saline control. As expected, treatment with taxol had no effect on tumour growth or weight (see FIGS. 15A & B).

Figure 16:
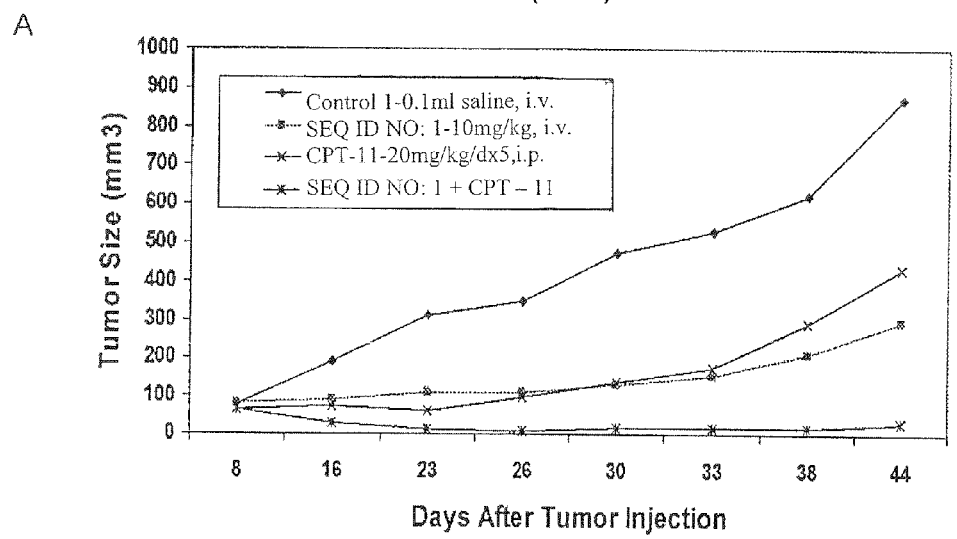
FIG. 16 depicts effects of SEQ ID NO: 1 in the treatment of LS513, human multi-drug resistant colon adenocarcinoma in SCID micev
Figure 16:
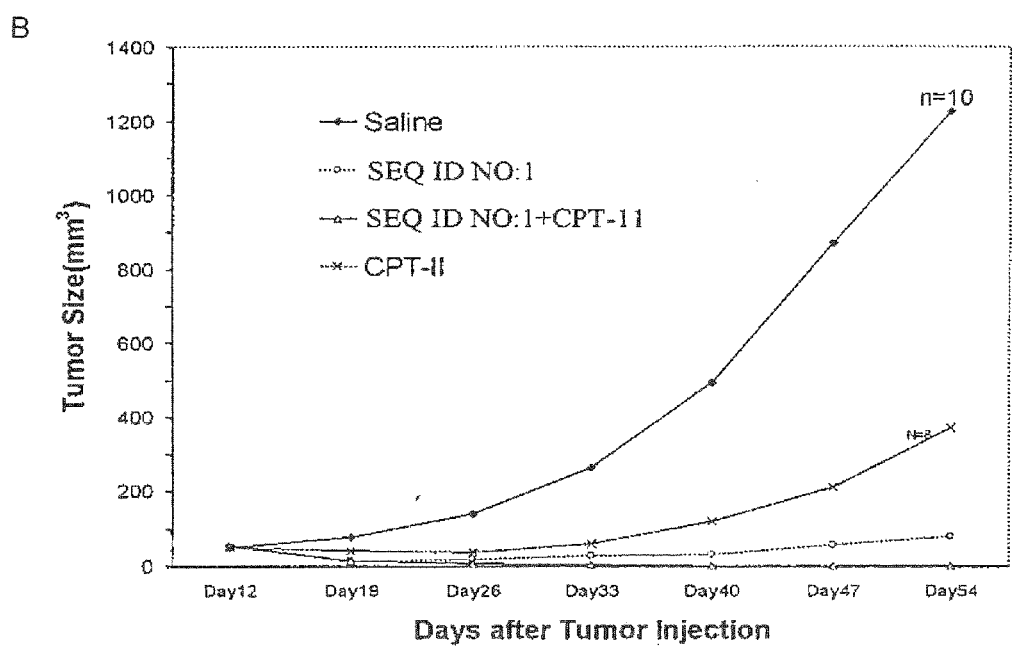
Figure 16:
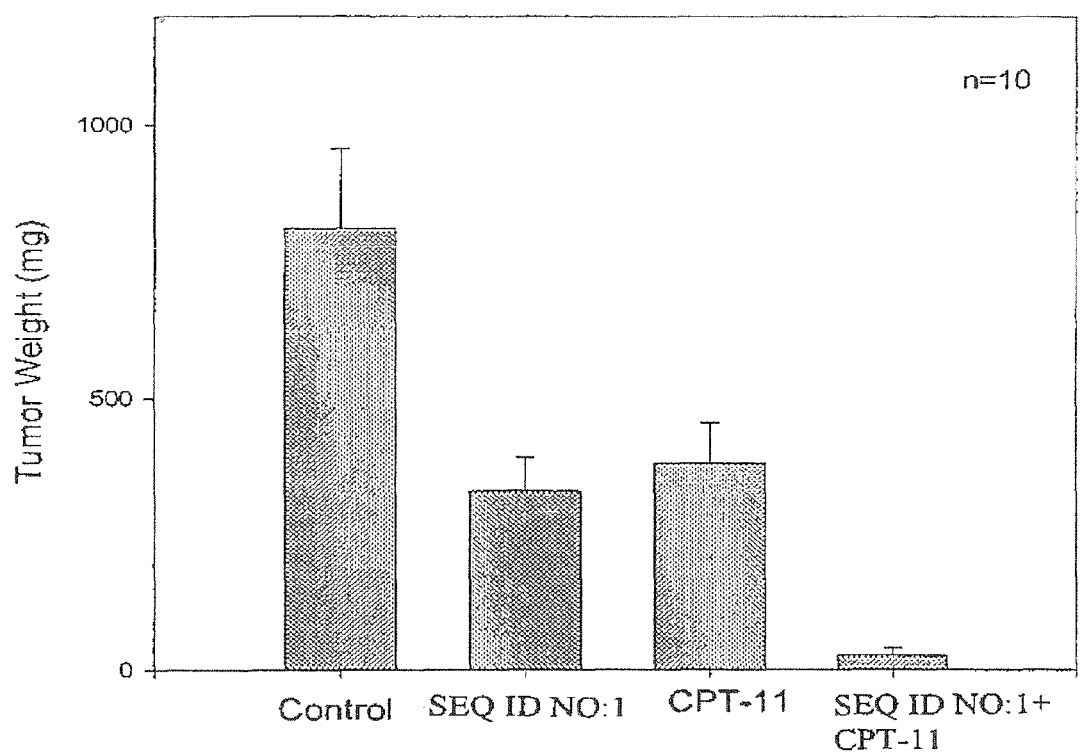

2.8 LS513 multi-drug resistant colon carcinoma cells ($1 \times 10^7$ cells in 100 µl of PBS) were subcutaneously injected into the right flank of 6-7 weeks old female SCID mice. After the size of tumour reached an approximate volume of 100 mm$^3$, 8 days post tumour cell injection, SEQ ID NO:1 was administered by bolus infusion into the tail vein every other day at 10 mg/kg. Control animals received saline alone for the same period. Antitumour effect of SEQ ID NO:1 was further compared to that of CPT-11 alone or in combination. CPT-11 was administered i.p. for 5 days at a dose of 20 mg/kg/day. Antitumour activities were estimated by the inhibition of tumour volume, which was measured with caliper. Each point represents mean tumour volume calculated from 10 animals per experimental group. Tumour weights were measured after animals were sacrificed at the end of the treatment. These cells are not resistant to CPT-11 which was used as a positive control. As illustrated, SEQ ID NO:1 treatment resulted in significant delay of tumour growth compared to saline control. SEQ ID NO:1 is as effective as CPT-11 and in combination the efficacy was greater than either treatment alone (see FIGS. 16A, B & C).

Results of SEQ ID NO:1 treatment of drug-resistant tumours alone or in combination with various chemotherapeutics are summarised in Table 4.

TABLE 3

Summary of SEQ ID NO: 1 Treatment of Drug Resistant Tumours

| Tumour resistance | Mouse | Treatment | Tumour weight as % of saline control | |
|---|---|---|---|---|
| LS513 (colon) multi-drug resistant (CPT-11 sensitive) | SCID | CPT-11 | 47 | |
| | | SEQ ID NO: 1 | 49 | |
| | | SEQ ID NO: 1 + CPT-11 | 3 | |
| MDA-CDDP-S4 (breast) Cisplatin | SCID | SEQ ID NO: 1 | 32 | |
| | | Taxol | 32 | |
| | | Cisplatin | 78 | |
| MDA-CDDP-S4 (breast) Cisplatin | SCID | SEQ ID NO: 1 | 18 | 41 |
| | | Taxol | 26 | 61 |
| | | SEQ ID NO: 1 + Taxol | 1 | 12 |
| MDA-MB435-To.1 (breast) Taxol | SCID | SEQ ID NO: 1 | 42 | |
| | | Taxol | 109 | |
| | | Cisplatin | 69 | |
| MDA-MB435-To.1 (breast) Taxol | CB-17/ SCID | SEQ ID NO: 1 | 37 | |
| | | Cisplatin | 56 | |
| | | SEQ ID NO: 1 + cisplatin | 22 | |
| HL-60 (leukemia) Taxol | SCID | SEQ ID NO: 1 | 38 | |
| | | Taxol | 119 | |
| BxPC-3 (pancreatic) Gemcitabine | CD-1 | SEQ ID NO: 1 | 5.8 | |
| | | Gemcitabine | 83 | |
| Hela S3 (cervix) hydroxyurea | SCID | SEQ ID NO: 1 | 24 | |
| | | Hydroxyurea (HU) | 92 | |
| | | Cisplatin | 63 | |
| | | SEQ ID NO: 1 + HU | 36 | |
| | | SEQ ID NO: 1 + Cisplatin | 13 | |

Results shown are mean tumour weights presented as a percentage of saline treated controls.

Example 3

In Vivo Testing of SEQ ID NO:1 Alone in Mouse Xenograft Models 3.1 HT-29 human colon cancer cells ($3 \times 10^6$ cells in 100 µl of PBS) were subcutaneously injected into the right flank of 6-7 week old CD-1 female nude mice. After the size of tumour reached an approximate volume of 100 mm$^3$, 4 days post tumour cell injection, SEQ ID NO:1 was administered by bolus infusion into the tail vein every other day at 10 mg/kg. Control animals received saline alone for the same period. Treatments lasted for 14 days thereafter. Antitumour activities were estimated by the inhibition of tumour volume, which was measured with a caliper on four different occasions over the treatment period. Each point represents mean tumour volume calculated from 5 animals per experimental group. As illustrated, SEQ ID NO:1 treatment demonstrated statistically significant inhibitory effects (P=0.0001) on the growth of human colon adenocarcinoma (see FIG. 17A).

Figure 17:
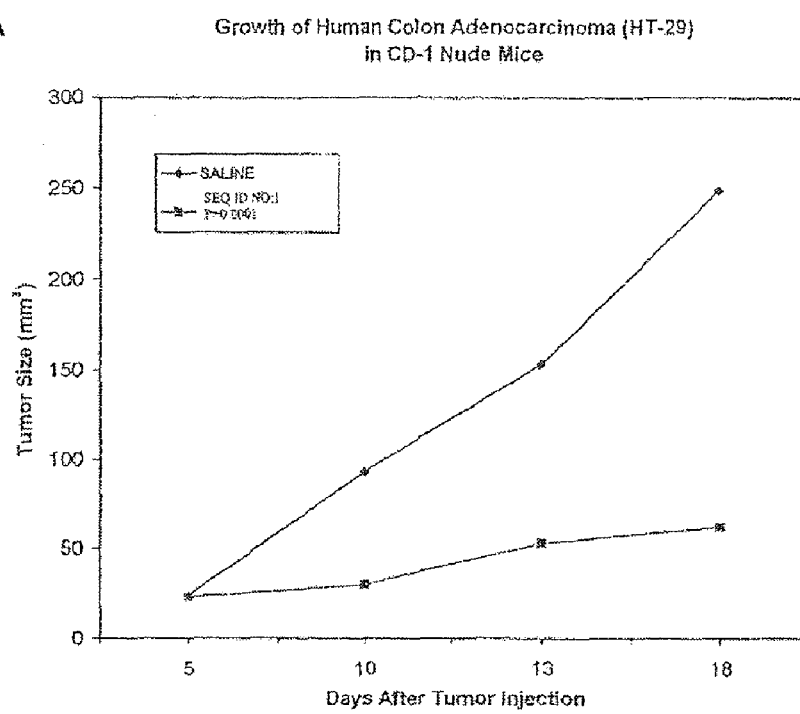
FIG. 17 depicts effects of SEQ ID NO: 1 on HT-29 colon tumour growth in CD-1 nude mice.
Figure 17:
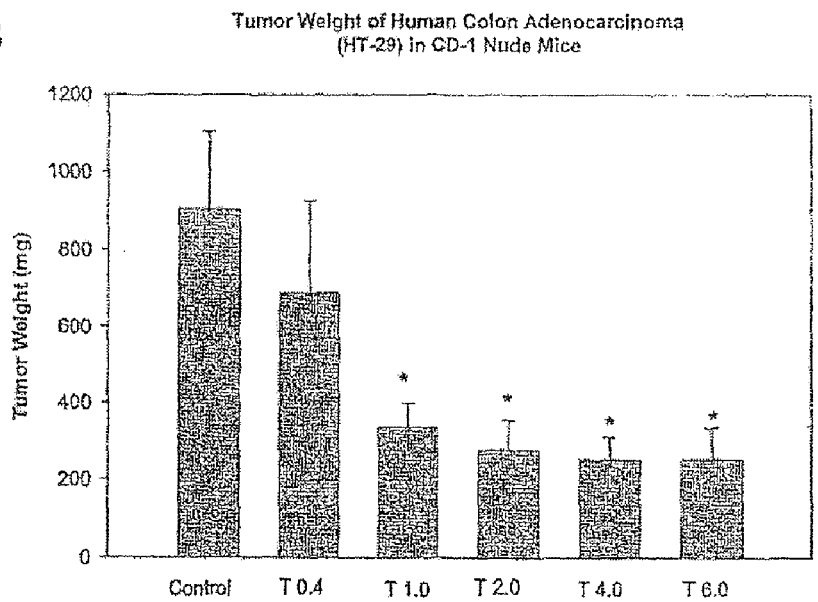

Antitumour effects of SEQ ID NO:1 were shown to be dose-dependent. HT-29 human colon cancer cells ($2 \times 10^6$ cells in 100 µl of PBS) were subcutaneously injected into the right flank of 6-7 week old CD-1 female nude mice. After the size of tumour reached an approximate volume of 100 mm$^3$, 5 days post tumour cell injection, increasing concentrations (0.4-6.0 mg/kg, designated as T0.4 to T6.0) of SEQ ID NO:1 were administered by bolus infusion into the tail vein every other day for 14 days. Control animals (control) received saline alone for the same period. At the end of the treatments, the animals were sacrificed, tumours were excised and their weights were measured. Each bar represents mean tumour weight calculated from 6 animals per experimental group. As illustrated in FIG. 17B, SEQ ID NO:1 exerted statistically significant inhibitory effects on the growth of human colon adenocarcinoma in a dose-dependent manner.

Figure 18:
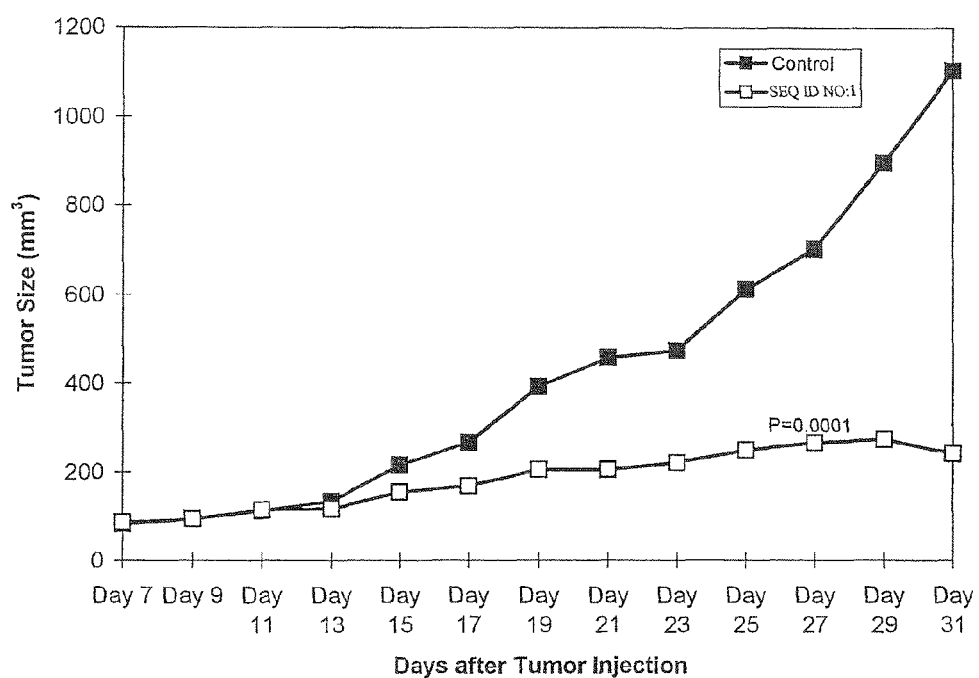
FIG. 18 depicts effects of SEQ ID NO: 1 on (A) A2058 melanoma growth in CD-1 nude mice, (B) MDA-MB-231 breast tumour growth in CD-1 nude mice, (C) SK-OV-3 ovary tumour growth in Balb/c nude mice, and (D) NCI-H460 lung tumour growth in CD-1 nude mice.

3.2 A2058 human skin cancer cells ($1 \times 10^7$ cells in 200 µl of PBS) were subcutaneously injected into the right flank of 6-7 week old CD-1 female nude mice. After the size of tumour reached an approximate volume of 100 mm$^3$, 7 days post tumour cell injection, SEQ ID NO:1 was administered by bolus infusion into the tail vein every other day at 10 mg/kg. Control animals received saline alone for the same period. Treatments lasted for 24 days thereafter. Antitumour activities were estimated by the inhibition of tumour volume, which was measured with a caliper at two-day intervals over the treatment period. Each point represents mean tumour volume calculated from 4 animals per experimental group. As illustrated in FIG. 18A, SEQ ID NO:1 exhibited strong inhibitory effects on the growth of human melanoma.

3.3 MDA-MB-231 human breast cancer cells ($1 \times 10^7$ cells in 200 µl of PBS) were subcutaneously injected into the right flank of 6-7 week old CD-1 female nude mice. After the size of tumour reached an approximate volume of 100 mm$^3$, 7 days post tumour cell injection, SEQ ID NO:1 was administered by bolus infusion into the tail vein every other day at 10 mg/kg. Control animals received saline alone for the same period. Treatments lasted for 24 days thereafter. Antitumour activities were estimated by the inhibition of tumour volume, which was measured with a caliper at two-day intervals over the treatment period. Each point represents mean tumour volume calculated from 4 animals per experimental group. As illustrated in FIG. 18B, SEQ ID NO:1 exhibited strong inhibitory effects on the growth of human breast carcinoma.

3.4 SK-OV-3 human ovarian cancer cells ($1\times10^7$ cells in 100 µl of PBS) were subcutaneously injected into the right flank of 5-6 week old Balb/c female nude mice. After the size of tumour reached an approximate volume of 100 mm$^3$, 11 days post tumour cell injection, SEQ ID NO:1 was administered by bolus infusion into the tail vein every other day at 10 mg/kg. Control animals received saline alone for the same period. Treatments lasted for 22 days thereafter. Antitumour activities were estimated by the inhibition of tumour volume, which was measured with a caliper on average at two-day intervals over the span of 22 days. Each point represents mean tumour volume calculated from 5 animals per experimental group. As illustrated in FIG. 18C, SEQ ID NO:1 exhibited statistically significant inhibitory effects on the growth of human ovary adenocarcinoma cells.

3.5 NCI-H460 human lung cancer cells ($5\times10^6$ cells in 100 µl of PBS) were subcutaneously injected into the right flank of 6-7 week old CD-1 female nude mice. After the size of tumour reached an approximate volume of 100 mm$^3$, 3 days post tumour cell injection, SEQ ID NO:1 was administered by bolus infusion into the tail vein every other day at 10 mg/kg. Control animals received saline alone for the same period. Treatments lasted for 14 days thereafter. Antitumour activities were estimated by the inhibition of tumour volume, which was measured with a caliper on four different occasions over 16-day period. Each point represents mean tumour volume calculated from 5 animals per experimental group. As illustrated in FIG. 18D, SEQ ID NO:1 treatment demonstrated strong inhibitory effects on the growth of human lung carcinoma.

Figure 19:
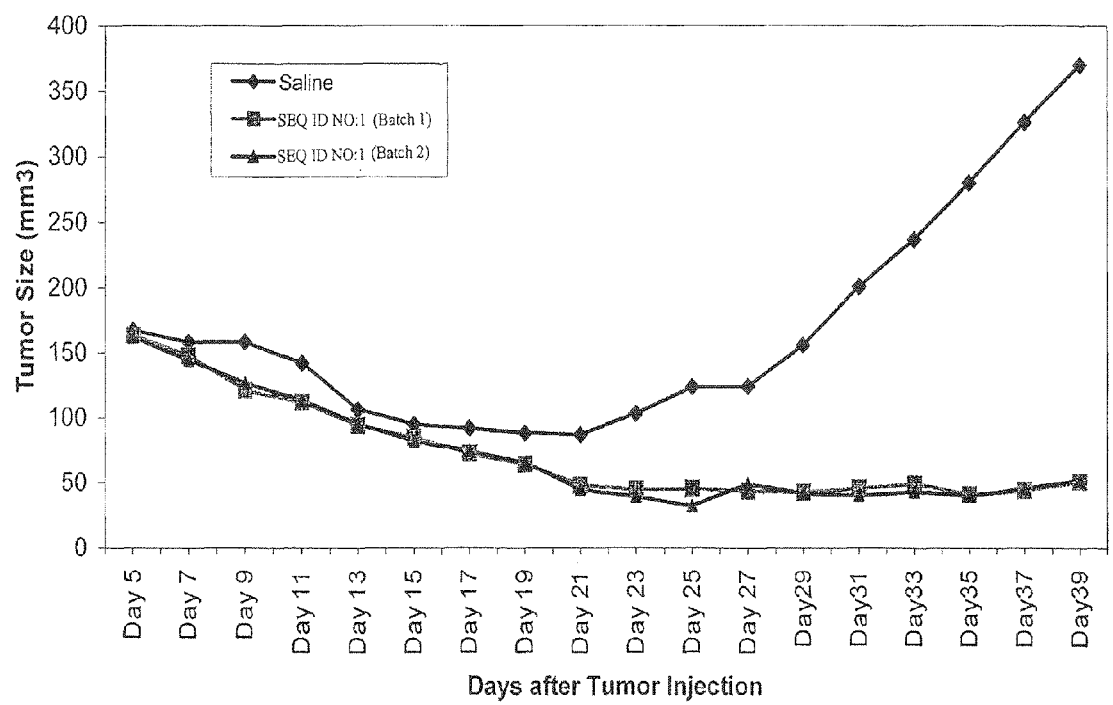
FIG. 19 depicts effects of SEQ ID NO: 1 on SU.86.86 pancreatic tumour growth in CD-1 nude mice.

3.6 SU.86.86 human pancreatic cancer cells ($1\times10^7$ cells in 100 µl of PBS) were subcutaneously injected into the right flank of 5-6 week old CD-1 female nude mice. After the size of tumour reached an approximate volume of 150 mm$^3$, 5 days post tumour cell injection, SEQ ID NO:1 was administered by bolus infusion into the tail vein every other day at 10 mg/kg. Two different batches of SEQ ID NO:1, synthesized at different times (designated as batch 1 and batch 2), were tested to detect possible batch-specific effects. Control animals received saline alone for the same period. Treatments lasted for 34 days thereafter. Antitumour activities were estimated by the inhibition of tumour volume, which was measured with a caliper at two-day intervals over the treatment period. Each point represents mean tumour volume calculated from 5 animals per experimental group. As illustrated in FIG. 19, SEQ ID NO:1 exhibited strong inhibitory effects on the growth of human pancreatic carcinoma and no batch-specific effects were evident.

Figure 20:
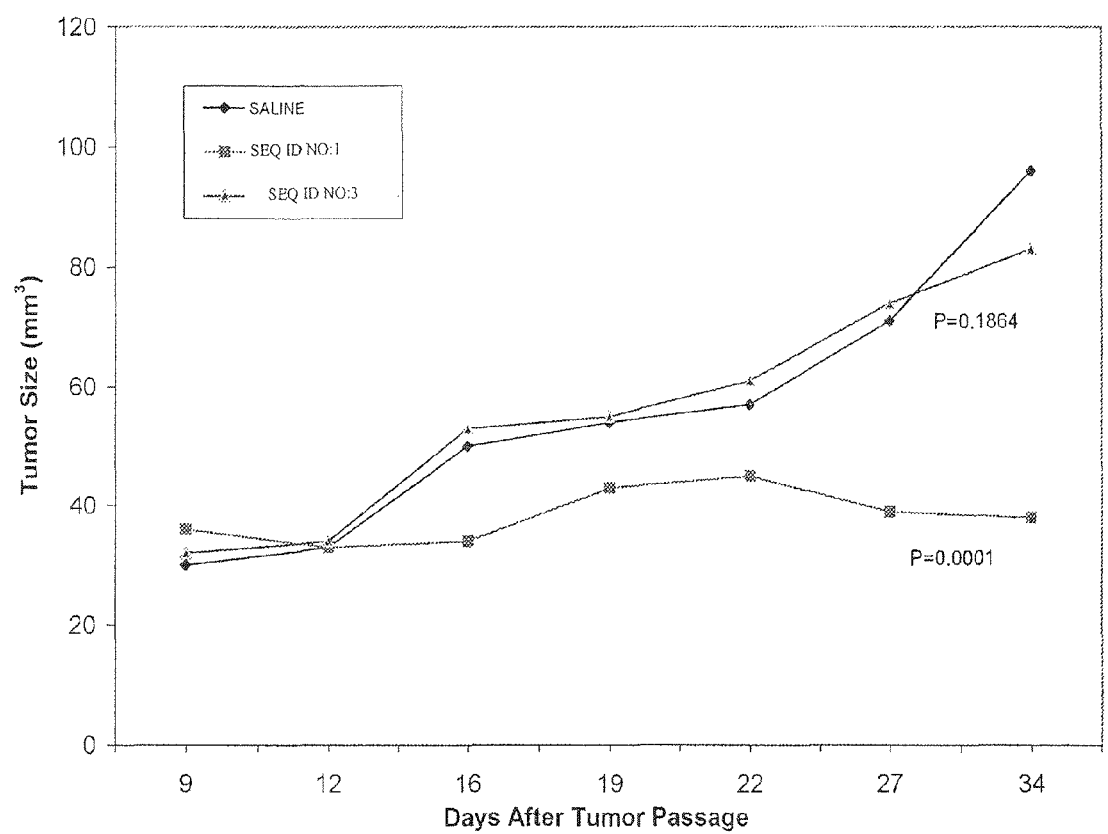
FIG. 20 depicts effects of SEQ ID NO: 1 on HepG2 liver tumour growth in CD-1 nude mice.

3.7 Hep G2 human liver cancer cells ($1\times10^7$ cells in 100 µl of PBS) were subcutaneously injected into the right flank of 7 week old CD-1 female nude mice. After the size of the tumour reached an approximate volume of 100 mm$^3$, each tumour mass was recovered and divided into approximately the same size before each piece (ca. 25 mg) was implanted into a new mouse. After 9 days of growth, SEQ ID NO:1 and scrambled control oligonucleotide (SEQ ID NO:3) were administered by bolus infusion into the tail vein every day at 2.5 mg/kg. Control animals received saline alone for the same period. Treatments lasted for 30 days thereafter. Antitumour activities were estimated by the inhibition of tumour volume, which was measured with a caliper at various time intervals over the span of 30 days. Each point represents mean tumour volume calculated from 6 animals per experimental group. As illustrated, SEQ ID NO:1 demonstrated significant inhibitory effects on the growth of human hepatoma cells, while tumour growth in mice treated with scrambled oligonucleotide did not differ from that in saline treated mice (see FIG. 20).

Figure 21:
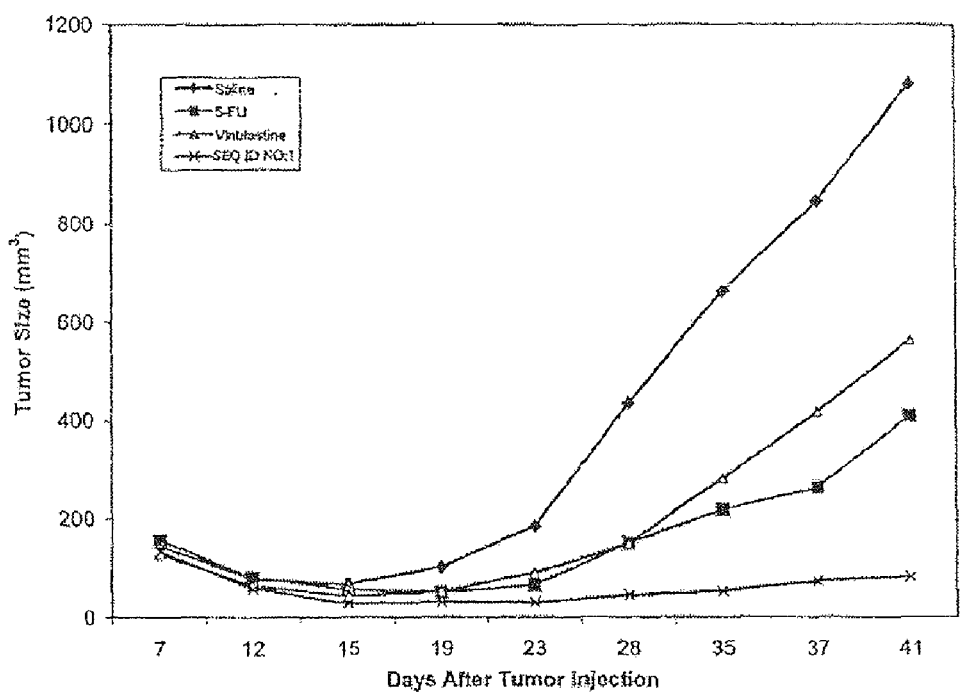
FIG. 21 depicts effects of SEQ ID NO: 1 on (A) Caki-1 kidney tumour growth in CD-1 nude mice, and (B) A498 kidney tumour growth in SCID mice.
Figure 21:
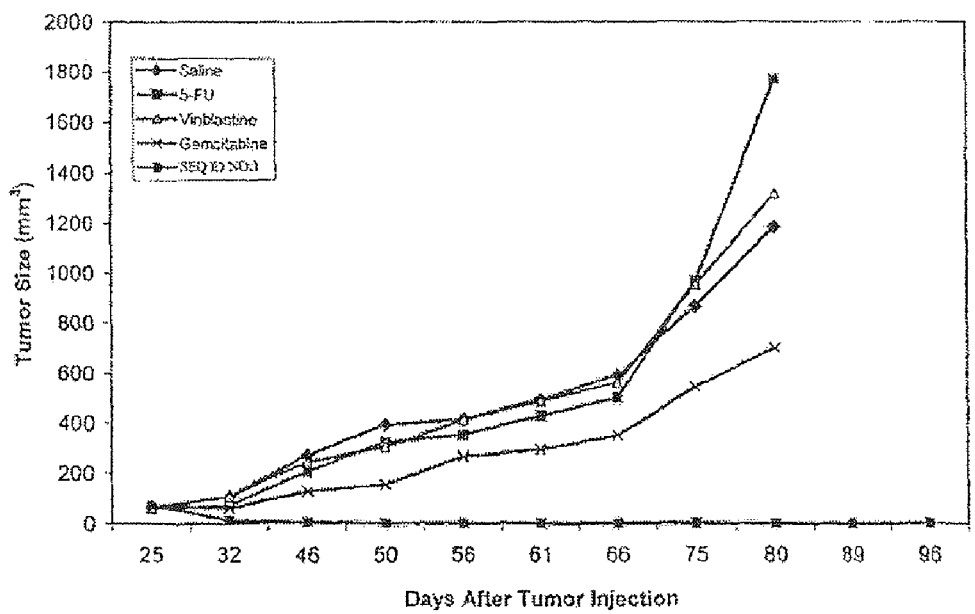

3.8 Caki-1 human kidney cancer cells ($1\times10^7$ cells in 100 µl of PBS) were subcutaneously injected into the right flank of 6-7 weeks old female CD-1 nude mice. After the size of tumour reached an approximate volume of 100 mm$^3$, 7 days post tumour cell injection, SEQ ID NO:1 was administered by bolus infusion into the tail vein every other day at 10 mg/kg. Control animals received saline alone for the same period. The antitumour effect of SEQ ID NO:1 was further compared to that of two chemotherapeutic agents: 5-FU and vinblastin. 5-FU was administered intraperitoneally at days 7-13, 21-28 and 35-36 with a dose of 13 mg/kg/day, while vinblastin was administered intraperitoneally at day 7, 14, 21, 28 and 35 at a dose of 0.6 mg/kg/week. All treatments were stopped at day 36. Antitumour activities were estimated by the inhibition of tumour volume, which was measured with a caliper. Each point represents mean tumour volume calculated from 5 animals per experimental group. As illustrated in FIG. 21A, SEQ ID NO:1 exhibited powerful inhibitory effects on the growth of human renal carcinoma cells, resulting in total regression of the tumours in three mice.

3.9 A498 human kidney cancer cells ($1\times10^7$ cells in 100 µl of PBS) were subcutaneously injected into the right flank of 6-7 weeks old female SCID mice. After the size of tumour reached an approximate volume of 100 mm$^3$, 25 days post tumour cell injection, SEQ ID NO:1 was administered by bolus infusion into the tail vein every other day at 10 mg/kg. Control animals received saline alone for the same period. The antitumour effect of SEQ ID NO:1 was further compared to that of three chemotherapeutic agents: 5-FU, vinblastin and gemcitabine. 5-FU was administered intraperitoneally at days 26-32, and 39-46 at a dose of 13 mg/kg/day, while vinblastin and gemcitabine were administered intraperitoneally at day 26, 32, 39, 46 and 52 at a dose of 0.6 mg/kg/week or 80 mg/kg/week, respectively. All treatments were stopped at day 52. Mice treated with saline or one of the three chemotherapeutic agents were sacrificed at day 80 because the tumour became too large. Mice treated with SEQ ID NO:1 were kept for 16 days further to observe possible resurgence of resistant tumour growth. Antitumour activities were estimated by the inhibition of tumour volume, which was measured with a caliper. Each point represents mean tumour volume calculated from 5 animals per experimental group. As illustrated in FIG. 21B, SEQ ID NO: 1 exhibited powerful inhibitory effects on the growth of human renal carcinoma cells, resulting in total regression of the tumours.

Figure 22:
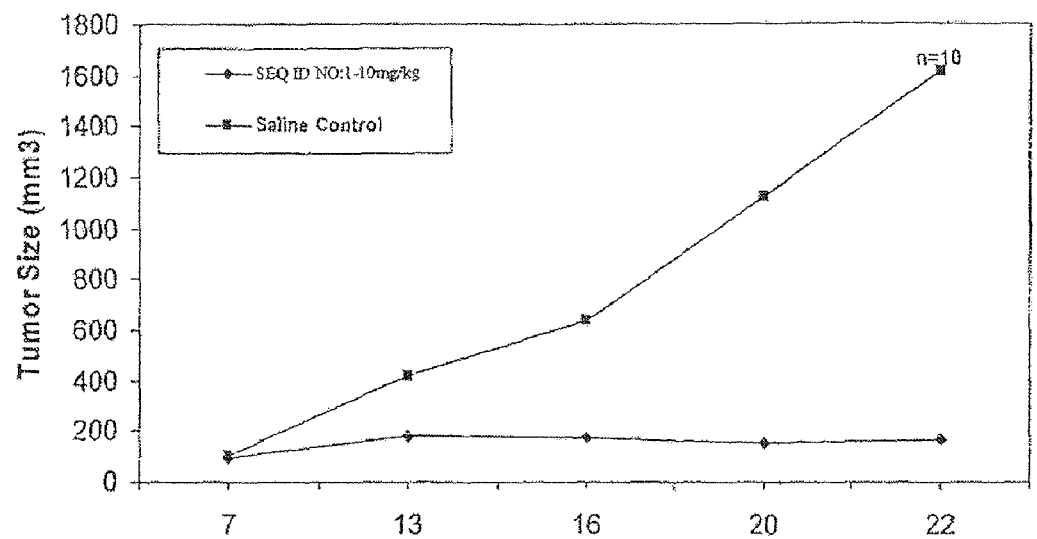
FIG. 22 depicts effects of SEQ ID NO: 1 on SIHA cervical tumour growth in SCID mice.
Figure 22:
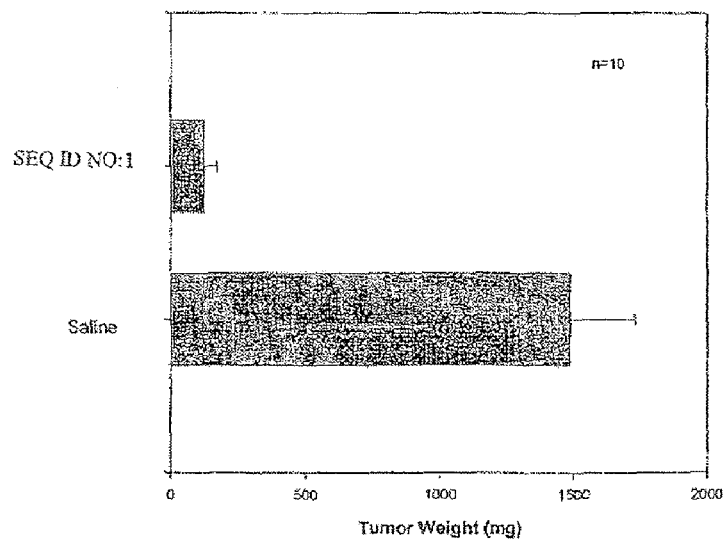

3.10 SIHA human cervical cancer cells ($1\times10^7$ cells in 100 µl of PBS) were subcutaneously injected into the right flank of 6-7 week old female SCID mice. After the size of tumour reached an approximate volume of 100 mm$^3$, 7 days post tumour cell injection, SEQ ID NO:1 was administered by bolus infusion into the tail vein every other day at 10 mg/kg. Control animals received saline alone for the same period. Treatments lasted for 16 days thereafter. Antitumour activities were estimated by the inhibition of tumour volume, which was measured with a caliper on five different occasions over 16-day period. Each point in FIG. 22A represents mean tumour volume calculated from 10 animals per experimental group. As illustrated, SEQ ID NO:1 treatment demonstrated strong inhibitory effects on the growth of human cervical carcinoma. FIG. 22B shows the results of weight measurements of tumours excised from the above animals at the end of the treatments, again demonstrating strong antitumour effect of SEQ ID NO:1.

Figure 23:
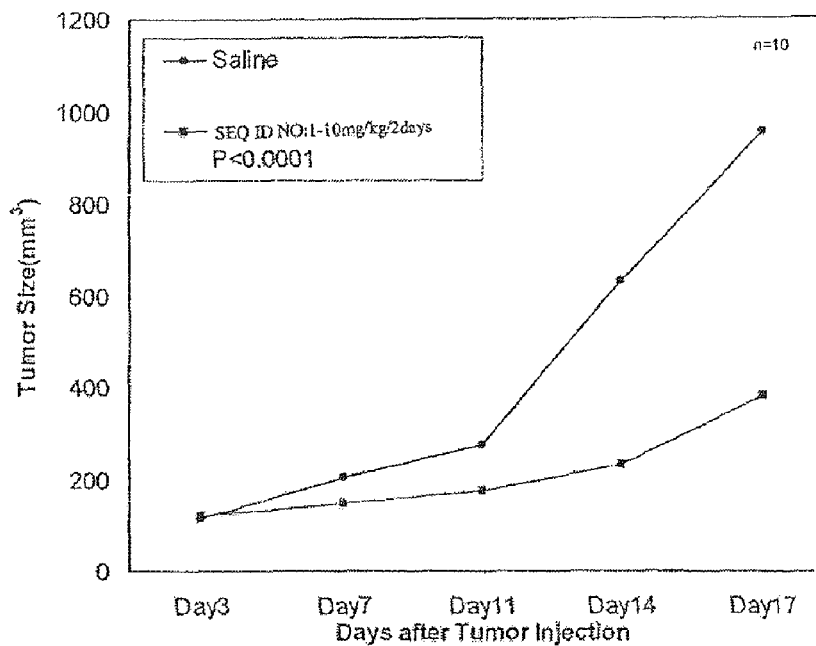
FIG. 23 depicts effects of SEQ ID NO: 1 on HeLa S3 cervical tumour growth in SCID mice.
Figure 23:
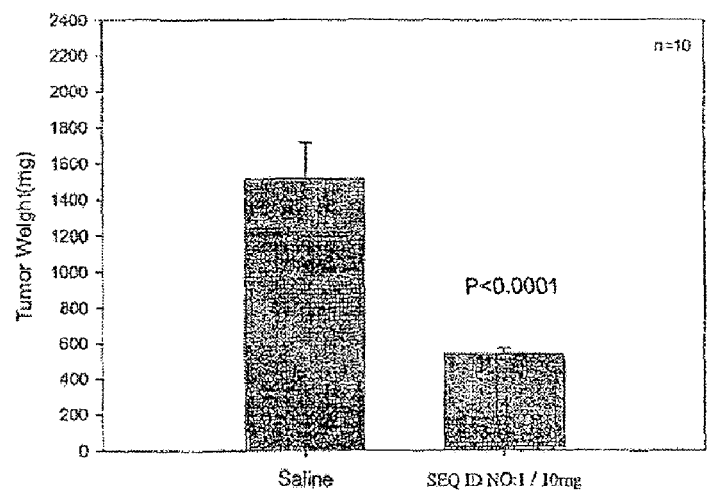

3.11 HeLa S3 human cervical cancer cells ($1 \times 10^7$ cells in 100 µl of PBS) were subcutaneously injected into the right flank of 6-7 week old female SCID mice. After the size of tumour reached an approximate volume of 100 mm$^3$, 3 days post tumour cell injection, SEQ ID NO:1 was administered by bolus infusion into the tail vein every other day at 10 mg/kg. Control animals received saline alone for the same period. Treatments lasted for 14 days thereafter. Antitumour activities were estimated by the inhibition of tumour volume, which was measured with a caliper on five different occasions over 14-day period. Each point in FIG. 23A represents mean tumour volume calculated from 10 animals per experimental group. As illustrated, SEQ ID NO:1 treatment demonstrated strong inhibitory effects on the growth of human cervical carcinoma. FIG. 23B shows the results of weight measurements of tumours excised from the above animals at the end of the treatments, again demonstrating strong antitumour effect of SEQ ID NO:1.

Example 4

Figure 24:
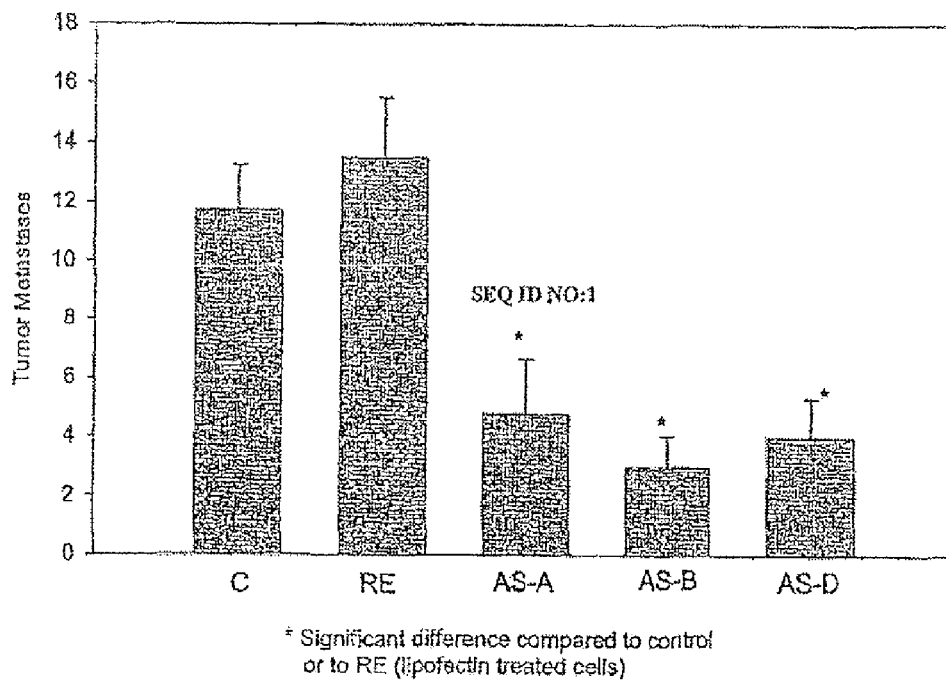
FIG. 24 depicts the reduction of lung nodule formation by SEQ ID NO: 1 in a mouse experimental model of metastasis using (A) mouse fibrosarcoma (R3) cells, and (B) C8161 human melanoma cells.
Figure 24:
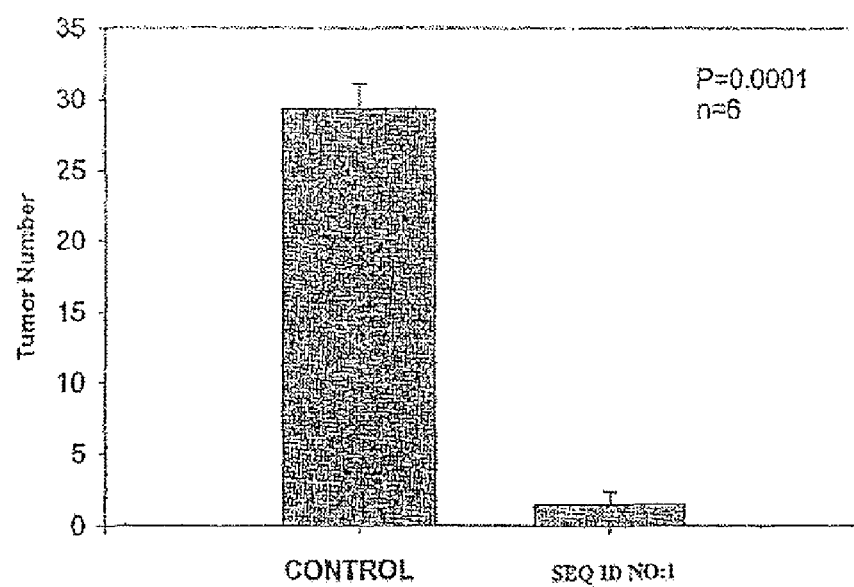

In Vivo Testing of SEQ ID NO: 1 in a Mouse Experimental Model of Metastasis 4.1 Experimental metastasis of mouse fibrosarcoma (R3) cells treated with different antisense oligonucleotides in a syngenetic model was estimated as follows. Aliquots of R3 cell suspension were seeded into 100 mm tissue culture dishes at a density of $2 \times 10^6$ and incubated overnight at 37° C. in α-MEM medium supplemented with 10% FBS. Cells were washed once in 10 ml of PBS and treated with 0.2 µM of SEQ ID NO: 1 in the presence of cationic lipid (Lipofectin reagent, final concentration, 10 µg/ml, Gibco BRL) for 4 hr. Cells were treated with either saline alone (C) or lipofectin alone (RE) as controls. Oligonucleotide was removed by washing the cells once with PBS and the cells were trypsinized. Cells were then collected by centrifugation, and approximately $1 \times 10^5$ cells suspended in 0.2 ml of PBS were injected into the tail veins of 10 week-old C3H female mice. Estimates of the number of lung tumours were made 20 days later, after excised lungs from individual mice were stained with picric acid dye solution (75% picric acid, 20% formaldehyde, 5% glacial acetic acid). The results are shown in FIG. 24a. Bars represent mean number of tumour nodules in lungs obtained from 4 to 5 animals per experimental group. Treatment of R3 cells with SEQ ID NO: 1 (AS-A) significantly reduced the formation of lung colonies (P=0.0006).

4.2 Experimental metastasis of C8161 human melanoma cells treated with SEQ ID NO:1 was estimated as follows. Aliquots of C8161 cell suspension were seeded into 100 mm tissue culture dishes at a density of $2 \times 10^6$ and incubated overnight at 37° C. in α-MEM medium supplemented with 10% FBS. Cells were washed once in 10 ml of PBS and treated with 0.2 µM of SEQ ID NO: 1 in the presence of cationic lipid (Lipofectin reagent, final concentration, 10 µg/ml, Gibco BRL) for 4 hr. Cells were treated with lipofectin alone (CONTROL) as a control. SEQ ID NO:1 was removed by washing the cells once with PBS and the cells were trypsinized. Cells were then collected by centrifugation, and approximately $1 \times 10^5$ cells suspended in 0.2 ml of PBS were injected into the tail veins of 6-8 week-old CD-1 athymic female nude mice. Estimates of the number of lung tumours were made 4 weeks later, after excised lungs from individual mice were stained with picric acid dye solution (75% picric acid, 20% formaldehyde, 5% glacial acetic acid). The results are shown in FIG. 24b. Bars represent mean number of tumour nodules in lungs obtained from 6 animals per experimental group. Treatment of C8161 cells with SEQ ID NO:1 significantly reduced the formation of lung colonies (P=0.0001).

Example 5

Prolonged Survival of SCID Mice Bearing Human Burkitt's Lymphoma

In vivo studies were conducted to assess the therapeutic potential of SEQ ID NO:1 in the treatment of lymphoma. Viable human Burkitt's lymphoma (Raji) cells ($5 \times 10^6$) collected from subconfluent logarithmically growing cultures were injected i.v. via the tail vein of each animal and disease was allowed to establish for 2 days. SEQ ID NO:1 in normal saline was administered by tail vein injections every second day at a dose of 10 mg/kg. Control animals received saline alone, without oligonucleotide. Treatment with SEQ ID NO:1 was stopped at day 42. The mice in both groups (n=10) were sacrificed at day 73. Antitumour effects of SEQ ID NO:1 treatment were assessed by the examination of survival of mice.

Figure 25:
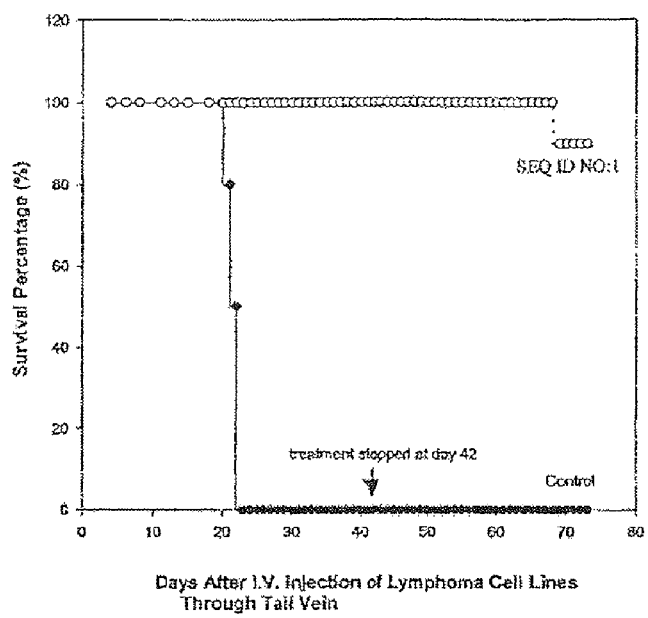
FIG. 25 depicts survival time of SCID mice bearing human lymphoma (Raji)
Figure 25:
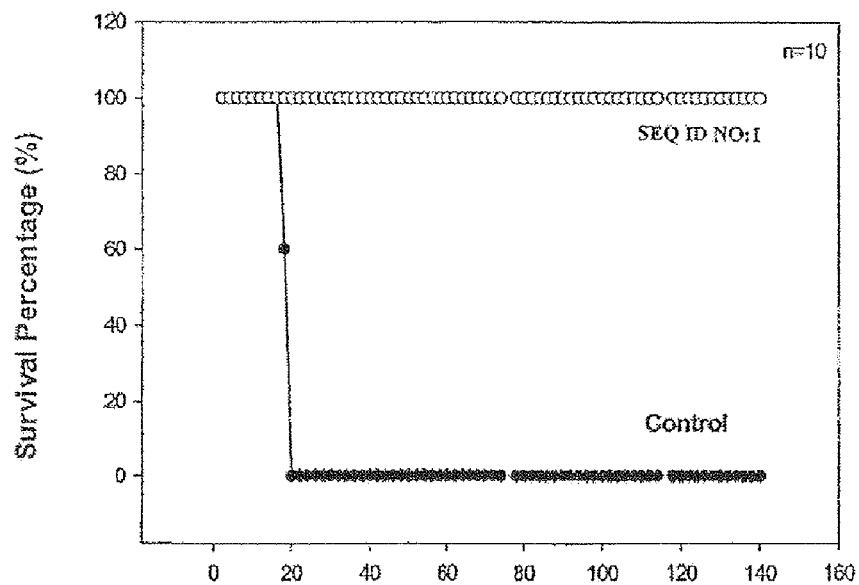

The results are shown in FIG. 25A. All mice died as a consequence of tumour progression within 23 days when left untreated. All SEQ ID NO:1 treated animals, on the other hand, survived beyond day 73 except one mouse, which died at day 69. In a similar study control oligonucleotides (mismatched sequence SEQ ID NO:2 and scrambled sequence SEQ ID NO:3) were administered with no observed efficacy suggesting SEQ ID NO:1 acts via a specific mechanism. These results suggest that the treatment with SEQ ID NO:1 may be an effective therapeutic strategy to prolong survival and to improve clinical outcome of human lymphoma patients.

A second independent study confirmed the anti-tumour activity of SEQ ID NO:1 as shown in FIG. 25B. Mice with established human Burkitt's lymphoma tumours were treated every second day with either saline or SEQ ID NO:1 for 44 days as described above. The control group mice all died from disease progression by day 20. At day 44, the SEQ ID NO:1 mice continued treatment on a weekly basis until stopping the treatment at day 73. All mice survived to the end of the experimental period (140 days).

Example 6

Prolonged Survival of SCID Mice Bearing Mouse Erythroleukaemia

In vivo studies were conducted to assess the therapeutic potential of SEQ ID NO:1 in the treatment of mouse Erythroleukaemia. CB7 Friend retrovirus-induced mouse Erythroleukaemia cells ($5 \times 10^6$) collected from subconfluent logarithmically growing cultures were injected i.v. via the tail vein of each animal and disease was allowed to establish for 2 days. SEQ ID NO:1 in normal saline was administered by tail vein injections every second day at a dose of 10 mg/kg. Control animals received saline alone, without oligonucleotide. Treatment with SEQ ID NO:1 was stopped at day 71. Antitumour effects of SEQ ID NO:1 treatment were assessed by the examination of survival of the mice.

Figure 26:
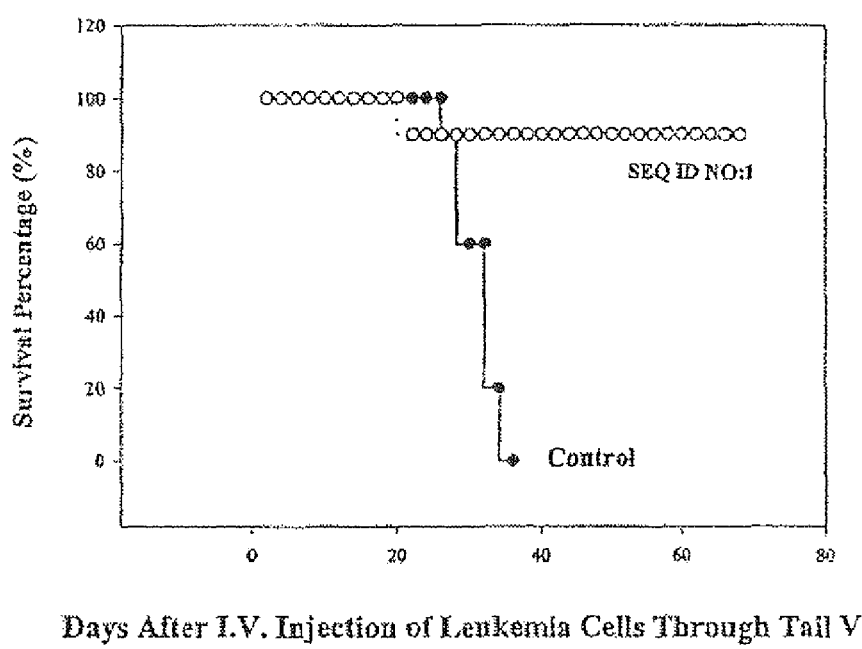
FIG. 26 depicts survival time of CB-17 SCID mice bearing erythroleukaemia (CB7)

The results are shown in FIG. 26. All mice died as a consequence of tumour progression within 36 days when left untreated. All SEQ ID NO:1 treated animals, on the other hand, survived beyond day 71 except one mouse, which died at day 22. The results suggest that the treatment with SEQ ID NO:1 may be an effective therapeutic strategy to prolong survival of human leukaemia patients.

Some of the results of in vivo assays conducted in mice with SEQ ID NO:1 are summarised in Table 5.

TABLE 5

Summary of Effects of SEQ ID NO: 1 on Tumour Growth and Metastasis

| Assay | Tumour Placed in Mouse | Results |
| --- | --- | --- |
| Tumour Growth | Mouse Fibrosarcoma[1] | Inhibition of tumour volume in C3H mice by approximately 80% on Day 15 after tumour laimpntation<br>Inhibition of tumour weight by approximately 80%<br>Dose-dependent decrease in tumour weight in C3H mice at doses of 0.5 to 30 mg/kg |
| | Human Colon Adenocarcinoma | Inhibition of tumour size in CD-1 nude mice by approximately 80% on Day 18 after tumour implantation<br>Inhibition of tumour weight by approximately 80%<br>Dose-dependent decrease in tumour weight in CD-1 nude mice at doses of 1.0 to 6.0 mg/kg |
| | Human Melanoma | Inhibition of tumour size by approximately 80 to 85% on Days 31 after tumour implantation<br>Inhibition of tumour weight of approximately 80% |
| | Human Breast Adenocarcinoma | Inhibition of tumour weight by approximately 80% on Day 31 after tumour implantation<br>Inhibition of tumour size by approximately 80% |
| | Human Pancreatic Adenocarcinoma | Complete inhibition of tumour growth up to 39 days after tumour implantation<br>Inhibition of tumour weight by approximately 65% |
| | Human Ovary Adenocarcinoma | Inhibition of tumour size by approximately 35% in Balb/c Nu-Nu mice on Days 19 to 25 after tumour implantation (FIG. 9) Inhibition of tumour weight of approximately 50% |
| | Human Lung Carcinoma | Inhibition of tumour size by approximately 85% in CD-1 Nude mice on Days 14 to 19 after tumour implantation<br>Inhibition of tumour weight of approximately 70% |
| | Human Liver Carcinoma | Inhibition of tumour size by 45% in CD-1 nude mice on Day 30 after tumour implantation<br>Inhibition of tumour weight of approximately 65% |
| | Human Glioblastoma-Astrocytoma | Inhibition of tumour weight of approximately 65% |
| | Human Renal Carcinoma | Approximately 90% inhibition of tumour size |
| | Human Renal Carcinoma[2] | Approximately 97% inhibition of tumour size |
| | Human Renal Carcinoma[2] | Complete regression of all tumours in treated mice |
| | Human Cervical Carcinoma[2] | Inhibition of tumour size by approximately 90% in SCID mice on Day 22 after tumour implantation<br>Inhibition of tumour weight of approximately 90% |
| | Human Cervical Carcinoma[2] | Inhibition of tumour size and weight by approximately 60% in SCID mice on Day 17fter tumour implantation |
| Metastasis | Mouse Fibrosarcoma (ex vivo) | Decrease by approximately 65% in the number of tumour metastases to lungs |
| | Human Melanoma (ex vivo and in vivo) | Decrease by approximately 95% in the number of tumour metastases to lungs |

Example 7

In Vivo Anti-Tumour Activity of SEQ ID NO:1

Cell Lines and Cell Culture

Unless noted otherwise in this Example human tumour cell lines were purchased from the American Type Culture Collections (ATCC) (Rockville, Md.). Human colon adenocarcinoma (HT-29), non-small cell lung carcinoma (NCI-H460), melanoma (A2058), breast adenocarcinoma (MDA-MB-231), pancreatic carcinoma (AsPC-1 and SU.86.86), glioblastoma-astrocytoma (U-87 MG), renal carcinoma (A498 and Caki-1), ovarian carcinoma (SK-OV-3), cervical carcinoma (HeLa S3), prostate carcinoma (PC-3), bladder carcinoma (T24), Burkitt's lymphoma (Raji) and hepatocellular carcinoma (Hep G2) were maintained, according to ATCC recommendation, in α-MEM, RPMI1640, or McCoy's 5a medium (Invitrogen Canada Inc. Burlington, Ontario) supplemented with 10-20% fetal calf serum (FCS) at 37° C. in a humidified atmosphere containing 5% $CO_2$. Normal human cell lines, WI-38 (human lung fibroblast) and HUVEC (human umbilical vein endothelial cells) and murine R3 (fibrosarcoma) and L (Ltk⁻ fibroblast) cells were maintained as mentioned above. C8161 metastatic melanoma cells were obtained from Dr. D. R. Welch, University of Pennsylvania, Hershey, Pa., and were maintained as above (Welch, et al., *Int J Cancer* 47:227-37 (1991)). All media used in these experiments contain an antibiotic-antimycotic solution at a final concentration of 100 units/ml penicillin and 100 μg/ml streptomycin (Invitrogen Canada Inc. Burlington, Ontario).

In Vivo Treatment with Antisense Oligonucleotides

CD-1 athymic female nude mice, BALB/c nu/nu nude mice, SCID, and SCID beige mice were purchased from Charles River Laboratories (Montreal, Canada) and experiments were typically initiated when the mice were 6-7 weeks old. Human tumour cells were grown in appropriate growth medium and $3 \times 10^6$–$1 \times 10^7$ cells suspended in 100 μl of PBS were subcutaneously injected into the right flank of the animals with a 23 gauge needle (cell number indicated in the figure legends). Each experimental group typically contained 10 mice. After the size of tumour reached a mean tumour volume of 50-100 $mm^3$, treatment was initiated. Antisense oligonucleotides (dissolved in saline) were administered by bolus infusion into the tail vein of animal every other day at the indicated dose. Treatment with 5-fluorouracil (Pharmacia), vinblastine (Faulding) and gemcitabine (Eli Lilly) was as indicated in the figure legend. Anti-tumour activity was estimated by the measurement of tumour volume with a calliper at two-three day intervals. Tumour volume was calculated by a formula $L \times W \times H/2$, where L indicates length, W indicates width and H indicates height. Within 24 hours after the last treatment, the animals were sacrificed and tumour and body weights were measured. Results of statistical analyses of the data are presented as P values in the figure legends.

Lymphoma Survival Assay

Viable human Burkitt's lymphoma (Raji) cells ($5 \times 10^6$) collected from subconfluent logarithmically growing cultures were injected intravenously into SCID mice, via the tail vein of each animal, and disease was allowed to establish for 2 days. Antisense oligonucleotides in normal saline, were administered by tail vein injections every second day at a dose of 10 mg/kg. Control animals received saline alone, without antisense oligonucleotide or with mismatched and scrambled control antisense oligonucleotides. Each treatment group typically contained 10 animals. The anti-tumour efficacy of treatment was assessed by the examination of the survival of the mice. Survival is reported as a percentage of the starting number of mice in the treatment group.

Experimental Metastasis Assay

C8161 human melanoma cells were seeded into 100 mm tissue culture dishes at a density of $2 \times 10^6$ and incubated overnight at 37° C. in α-MEM medium supplemented with 10% FBS. The cells were trypsinized, collected by centrifugation and aliquots were removed from the suspension to determine the cell viability using trypan blue exclusion test. Approximately $1 \times 10^5$ cells suspended in 0.1 ml of PBS were injected into the tail vein of 6-8 week old CD-1 athymic female nude mice. Treatment was initiated after 2 days. Estimates of the number of lung nodules were made 5-7 weeks later, after excised lungs from individual mice were stained with picric acid dye solution (75% picric acid, 20% formaldehyde, 5% glacial acetic acid).

Results

Figure 27:
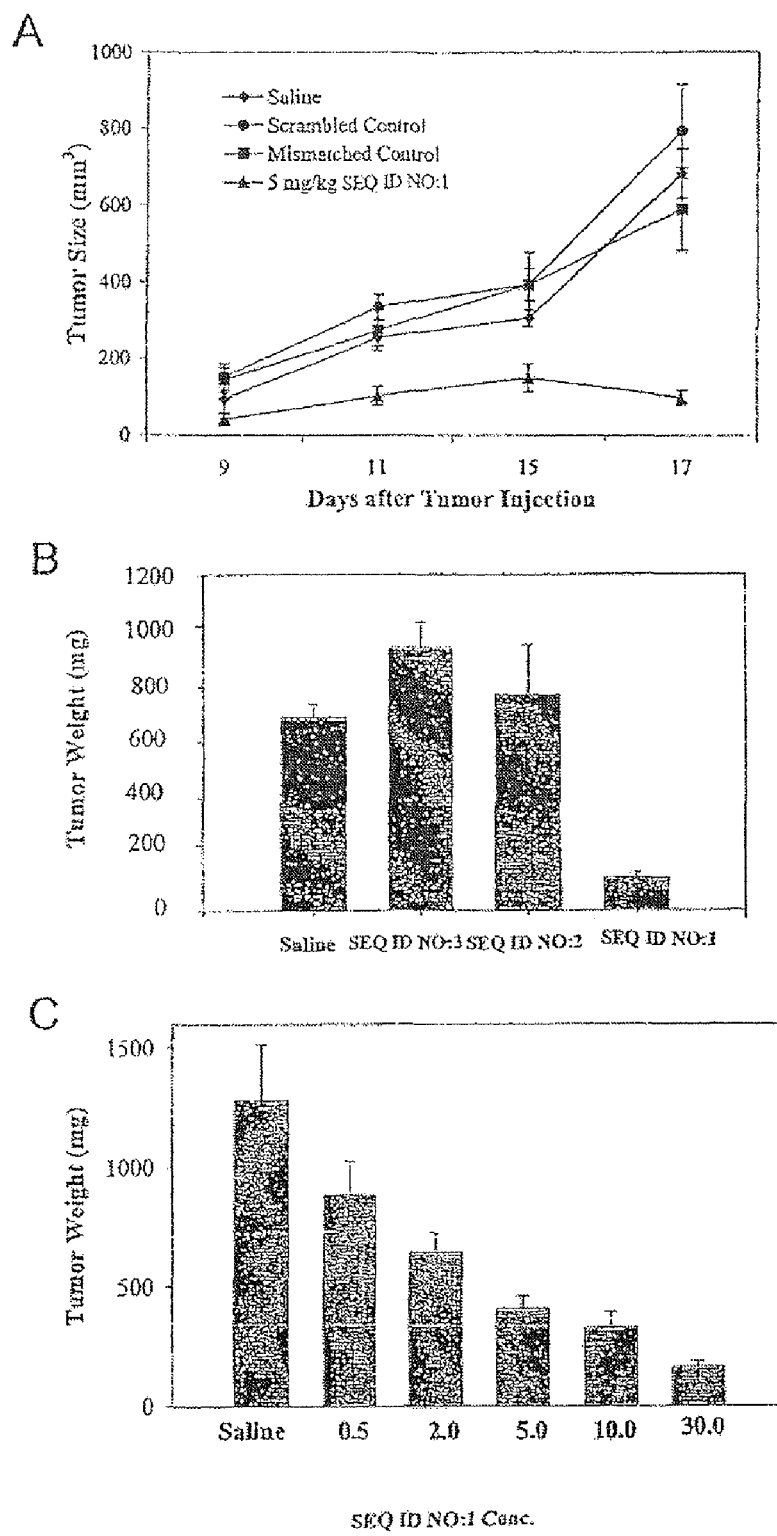
FIG. 27 depicts the effect of SEQ ID NO:1 on the growth of R3 mouse fibrosarcoma cells in C3H mice.

SEQ ID NO:1 Displays Sequence-Specific and Dose-Dependant Anti-Tumour Activity In Vivo R3 mouse fibrosarcoma cells ($1.5 \times 10^6$ cells in 100 μl of PBS) were subcutaneously injected into the right flank of 6-8 week old C3H female mice. After the size of tumour reached an approximate volume of 100 $mm^3$, 3 days post tumour cell injection, SEQ ID NO:1, SEQ ID NO:2 and SEQ ID NO:3 were administered by bolus infusion into the tail vein every other day at 5 mg/kg. Control animals received saline alone for the same period. Treatments lasted for 14 days thereafter. Anti-tumour activities were estimated by the inhibition of tumour volume, which was measured with a calliper at two-day intervals starting from day 9. Each point in FIG. 27A represents the mean tumour volume calculated from 6-7 animals per experimental group. The SEQ ID NO:1 treatment group had significant anti-tumour efficacy compared to saline, scrambled and mismatched controls (P=0.0001) FIG. 27B shows the mean weight of tumours excised from the above animals at the end of treatment. SEQ ID NO:1 had significant anti-tumour activity compared to saline (P=0.0006), scrambled (P=0.0001) and mismatched (0.0002) controls.

R3 mouse fibrosarcoma cells ($2 \times 10^6$ cells in 100 μl of PBS) were subcutaneously injected into the right flank of 6 week old C3H female mice. After the size of tumour reached an approximate volume of 100 $mm^3$, 4 days post tumour cell injection, increasing concentrations (0.5-30 mg/kg, designated as 0.5 to 30) of SEQ ID NO:1 were administered by bolus infusion into the tail vein every other day for 10 days. Control animals received saline alone for the same period. At the end of the treatments, the animals were sacrificed, tumours were excised and their weights were measured. Each bar in FIG. 27C represents mean tumour weight and standard error calculated from 6-8 animals per experimental group. P values compared to saline were as follows: 0.5 mg/kg (P=0.04), 2 mg/kg (P=0.0001), 5 mg/kg (P=0.0015), 10 mg/kg (P=0.0001), 30 mg/kg (P=0.0001).

FIG. 27C shows that SEQ ID NO:1 demonstrates dose-dependent anti-tumour activity against both murine (R3).

Figure 28:
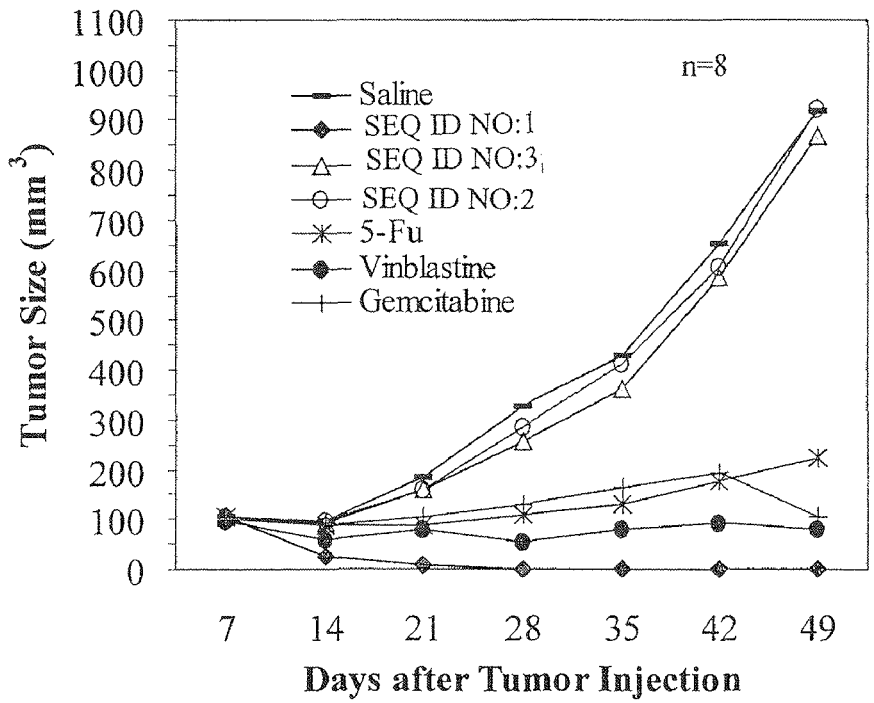
FIG. 28 depicts the effect of SEQ ID NO:1 on the growth of Caki-1 human kidney cancer cells and A498 human kidney cells in SCID mice.
Figure 28:
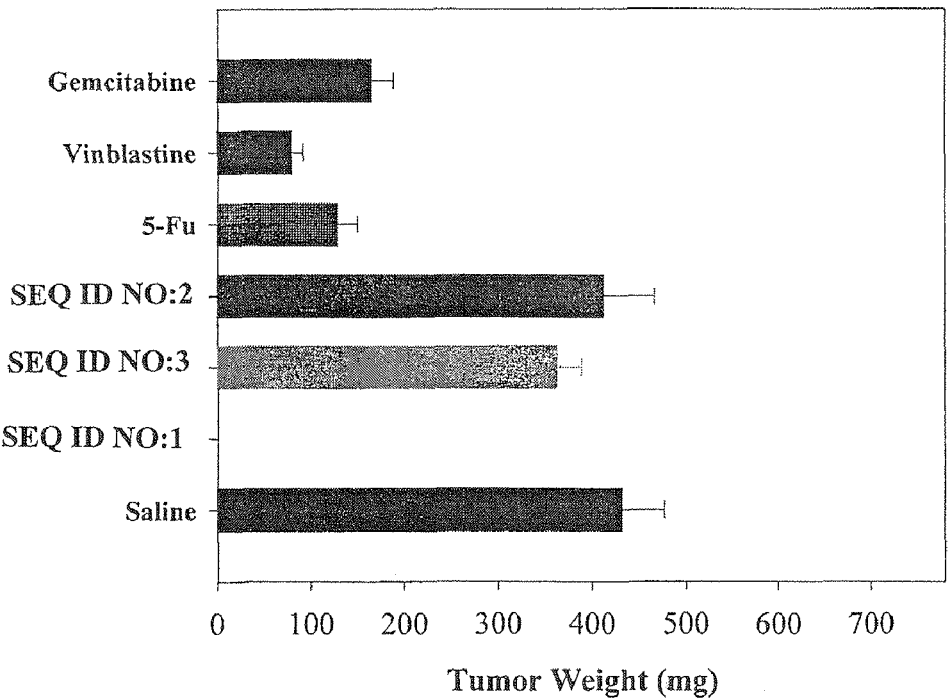

Interestingly, SEQ ID NO:1 has exceptional efficacy against renal cell carcinomas. FIG. 28 shows the results from xenograft experiments with Caki-1 human kidney cancer cells in which $5 \times 10^6$ cells in 100 μl of PBS were subcutaneously injected into the right flank of 6-7 weeks old female SCID mice. After the size of tumour reached an approximate volume of 100 $mm^3$, 7 days post tumour cell injection, SEQ ID NO:1, SEQ ID NO:2, or SEQ ID NO:3 were administered (10 mg/kg/2 days, i.v.). Three additional treatment groups received: 5-FU (13 mg/kg/day×5), vinblastine (1 mg/kg/week) and gemcitabine (100 mg/kg/week). Control animals received saline alone for the same period. Calliper measurements at 1-week intervals were used to calculate tumour volumes. Each point in FIG. 28A represents mean tumour volume calculated from 10 animals per experimental group (with the exception of SEQ ID NO:1 which was 8 animals). P values compared to saline: SEQ ID NO:1 (P<0.0001), scrambled (P=0.4032), mismatched (P=0.8555), 5-FU (P<0.0001), vinblastine (P<0.0001), gemcitabine (P<0.0001).

After 49 days the mice were sacrificed and the tumours weighed. The results are shown in FIG. 28B. Each bar represents the mean tumour weight and standard error calculated for each treatment group. P values compared to saline: SEQ ID NO:1 (P=0.0001), scrambled (P=0.7183), mismatched (P=0.3254), 5-FU (P=0.0002), vinblastine (P=0.0001), gemcitabine (P=0.0007).

FIGS. 28C & D show results using A498 human kidney cancer cells. $5 \times 10^6$ cells in 100 µl of PBS were subcutaneously injected into the right flank of 6-7 weeks old female SCID mice. After the size of tumour reached an approximate volume of 100 mm$^3$, 19 days post tumour cell injection, SEQ ID NO:1, SEQ ID NO:2, or SEQ ID NO:3 were administered (10 mg/kg/2 days, i.v.). Three additional treatment groups received: 5-FU (13 mg/kg/day×5), vinblastine (1 mg/kg/week) and gemcitabine (100 mg/kg/week). Control animals received saline alone for the same period. Caliper measurements at 1-week intervals were used to calculate tumour volumes. Each point in FIG. 28C represents mean tumour volume calculated from 10 animals per experimental group (with the exception of SEQ ID NO: 1 which was 8 animals). P values compared to saline: SEQ ID NO:1 (P=0.0001), scrambled (P=0.8786), mismatched (P=0.8224), 5-FU (P=0.8826), vinblastine (P<0.0001), gemcitabine (P<0.0001). After 54 days the mice were sacrificed and the A498 tumours weighed. The results are shown in FIG. 28D. Each bar represents the mean tumour weight and standard error calculated for each treatment group. P values compared to saline: SEQ ID NO:1 (P<0.0001), SEQ ID NO:3 (P=0.5145), SEQ ID NO:2 (P=0.5741), 5-FU (P=0.9548), vinblastine (P=0.0582), gemcitabine (P=0.0012). SEQ ID NO:1 treatment can be seen to result in dramatic inhibition in growth of Caki-1 and A498 renal tumours as assessed by both tumour volume and tumour weight at the experimental end point. Treatment resulted in a rapid tumour stabilization and shrinkage within the first week of treatment. Tumour regression was complete within 3 weeks of treatment (day 28, post implantation of tumour). At the same dose, treatment with the control oligonucleotides resulted in tumour growth that was indistinguishable from saline treatment.

Figure 29:
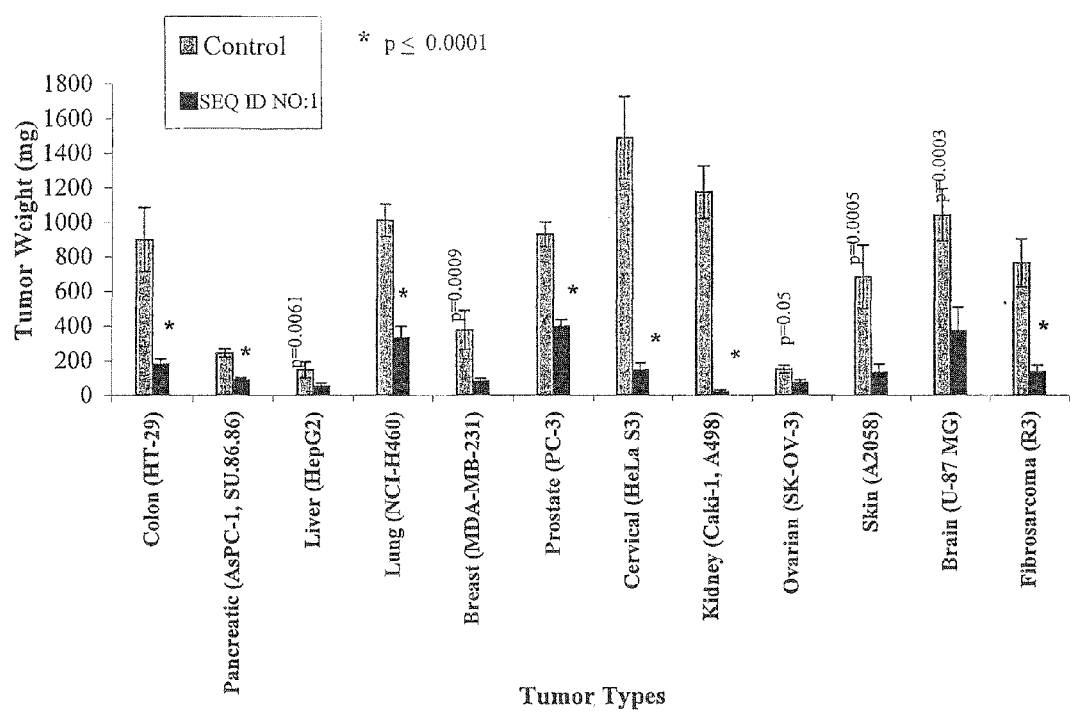
FIG. 29 depicts the effect of SEQ ID NO:1 in a variety of human tumour cell lines in xenograft experiments.

Consistent with a RNR having a general role in tumour growth, SEQ ID NO:1 displays anti-tumour activity against a wide range of solid tumours in vivo. FIG. 29 summarizes the results of a statistical analysis of data compiled from a number of experiments in which the effect of SEQ ID NO:1 on tumour growth was assessed in human tumour cell xenografts in mice. Each data point represents tumour weight and standard error. The experiments were carried out as follows: Tumour cell suspensions ($1.5 \times 10^6$ to $10^7$) were injected s.c. into the right flank of the mice for the tumour lines shown (except for hepatocellular carcinoma cells, which were subcutaneously implanted as a tumour mass). Treatment started when a tumour mass was palpable, usually ranged between 50 to 100 mm3. Oligonucleotide concentrations used in treatments ranged from 2.5 mg/kg to 10 mg/kg, administered i.v., every second day. Tumour weight is expressed in mg and was obtained approximately 2 weeks after the start of oligonucleotide treatments, except for slow growing tumours such as hepatocellular carcinoma where tumour weight was obtained after 4 weeks of treatment. Differences in tumour weight between control and oligonucleotide treated groups were statistically significant in all cases (p<0.05).

Unlike examples of antisense compounds developed against specific tumours (e.g. Bcl-2), SEQ ID NO:1 appears to be active against a range of cancer types. In all cancer cell lines tested, SEQ ID NO:1 treatment resulted in a significant decrease in tumour growth (volume over time) and endpoint weight.

SEQ ID NO:1 has Superior Anti-Tumour Efficacy Compared to RNR-Based Therapeutic Compounds In order to assess the clinical potential of SEQ ID NO:1, its efficacy against human tumour cell xenografts in mice was compared to that of 5-FU, gemcitabine and vinblastine (FIG. 28). These compounds are currently in clinical use and are thought to act, at least partially, by decreasing RNR activity. Without exception SEQ ID NO:1 was superior to any of these compounds against two human renal tumours, Caki-1 and A498 tumours (FIG. 28). In addition, SEQ ID NO:1 was the only compound that displayed long term protection from tumour growth. In A498 tumour xenografts, 5-FU, gemcitabine and vinblastine treatments were all ineffective in stabilization of the tumours. By day 54, mice treated with 5-FU had tumours that were equal in volume and weight to tumours of saline-treated animals. While vinblastine and gemcitabine displayed better efficacy than 5-FU there was, at best, a delay in the rate of tumour growth (FIG. 28C). These results are significant in that SEQ ID NO:1 is the only RNR-based compound developed to date that is highly specific for its target, thereby decreasing the potential for toxicity.

SEQ ID NO:1 Treatment Dramatically Prolongs Survival in Xenograft Model

Figure 30:
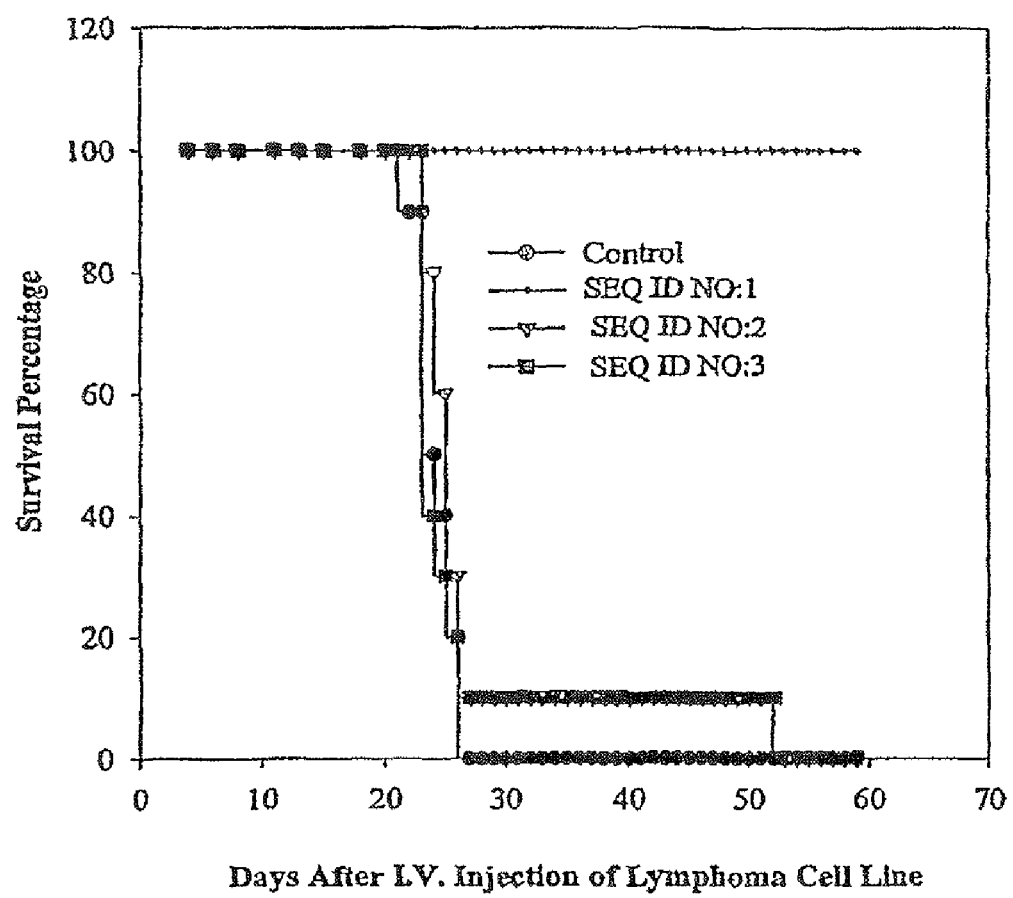
FIG. 30 depicts the effect of SEQ ID NO:1 on the survival of mice injected with human Burkitt's lymphoma (Raji) cells.

As an additional test of efficacy SEQ ID NO:1 was administered to SCID mice bearing active Burkitt's lymphoma (FIG. 30). Viable human Burkitt's lymphoma (Raji) cells ($5 \times 10^6$) collected from subconfluent logarithmically growing cultures were injected i.v. into each animal and disease was allowed to establish for 2 days. SEQ ID NO:1, SEQ ID NO:3 and SEQ ID NO:2, in normal saline were administered by tail vein injection every second day at a dose of 10 mg/kg. At day 40 the treatment schedule was reduced to 10 mg/kg every 3 days. Control animals received saline alone, without oligonucleotide. Survival is presented as a percentage of the starting number of mice over time. All the SEQ ID NO:1-treated mice survived to the end of the study and were sacrificed at day 72 due to animal housing limitations.

SEQ ID NO:1 treatment leads to a dramatic increase in survival time of mice well beyond the treatment period (up to 72 days post-end of treatment). In addition to prolonged survival, the SEQ ID NO:1-treated mice appeared to recover from the symptoms associated with the lymphoma. As treatment progressed the SEQ ID NO:1-treated mice changed from having rough coats and weight loss to smooth coats and weight gain. Although strictly qualitative, these observations would suggest that the disease is not only stabilizing, but also regressing, consistent with the prolonged survival post-end of treatment.

Finally, neither SEQ ID NO:3 nor SEQ ID NO:2 control ODNs prolonged survival, consistent with SEQ ID NO:1 acting via a sequence-specific mechanism.

Figure 31:
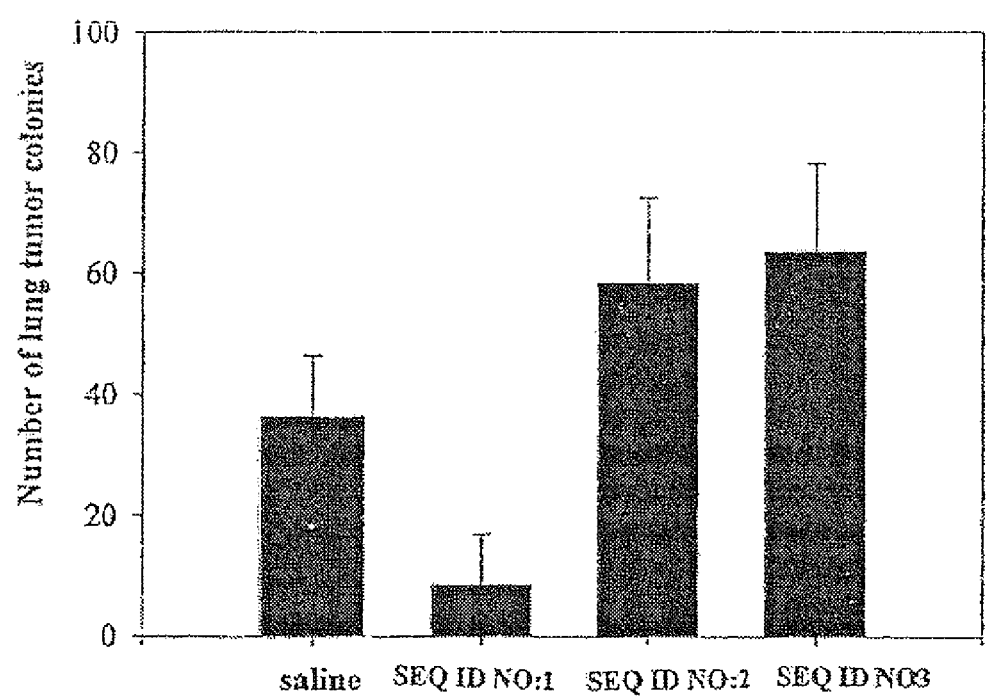
FIG. 31 depicts the effect of SEQ ID NO:1 on metastasis of C8161 melanoma cells in SCID mice.

SEQ ID NO:1 Treatment Dramatically Decreases Lung Nodule Formation in an Experimental Metastasis Model Murine R3 fibrosarcoma and human C8161 melanoma cells injected into the tail vein of mice form observable lung nodules 2 weeks post-injection. Pre-treatment of these tumour cells with 0.2 µM SEQ ID NO:1 in culture, prior to injection into mice, significantly reduces the extent of lung nodule formation. To more accurately reflect the clinical situation, mice were treated with SEQ ID NO:1 post tumour cell injection. C8161 human metastatic melanoma cells were seeded into 100 mm tissue culture dishes at a density of $2\times10^6$ and incubated overnight at 37° C. in α-MEM medium supplemented with 10% FBS. The cells were trypsinized, collected by centrifugation and aliquots were removed from the suspension to determine the cell viability using trypan blue exclusion test. Approximately $1\times10^5$ cells suspended in 0.1 ml of PBS were injected into the tail veins of 6-8 week old female SCID mice. Treatment was initiated after 2 days. Estimates of the number of lung nodules were made 5-7 weeks later, after excised lungs from individual mice were stained with picric acid dye solution (75% picric acid, 20% formaldehyde, 5% glacial acetic acid). The results are shown in FIG. 31, bars represent the mean number of nodules per mouse with standard error. In the SEQ ID NO:1 treatment group only one of the 9 mice had lung nodules.

As with the tumour and survival assays, there was no anti-metastatic activity associated with treatment with control ODNs (FIG. 31, SEQ ID NO:2 and SEQ ID NO:3), again confirming the sequence-specific effect of SEQ ID NO:1.

Example 8

Immune Stimulation

The following experiments were conducted in order to determine whether SEQ ID NO:1 produces non-specific immune stimulation that is not a result of target sequence interactions. Immune stimulation can be the result of un-methylated CpG di-nucleotides, which stimulate innate immune responses in vertebrates and can further augment acquired immune responses to both pathogens and tumour cells. The presence of un-methylated CpGs in an oligonucleotide can have the same effect if in an optimal sequence context.

Figure 32:
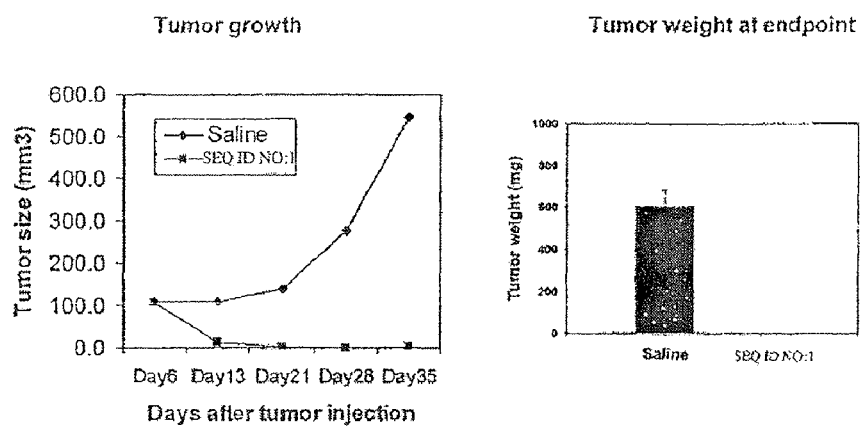
FIG. 32 depicts effects of SEQ ID NO:1 on Caki renal tumour xenografts in SCID/Beige mice.
Figure 32:
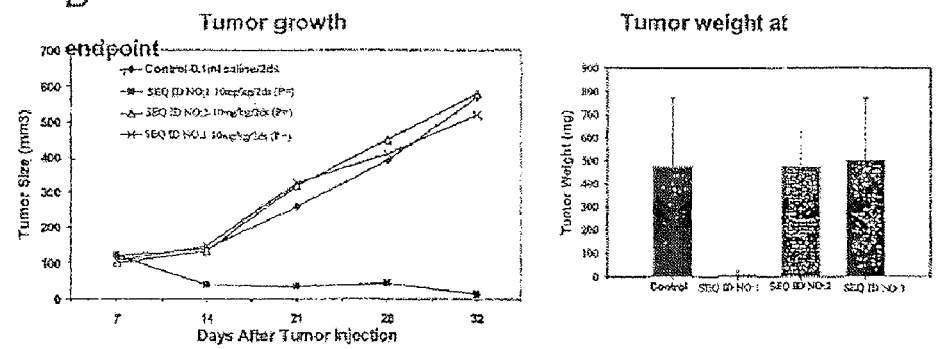

To directly determine whether SEQ ID NO:1 treatment results in CpG stimulation of NK-mediated anti-tumour activity, the efficacy of SEQ ID NO:1 on human tumour xenografts in SCID/beige mice was assessed (FIG. 32). SCID/beige mice lack B, T and NK cell function and as such these mice cannot mount a significant innate or acquired immune response. It is clear from tumour growth data that Caki renal tumour xenografts in SCID/beige mice are effectively treated with SEQ ID NO:1 (FIG. 32A). Clearly, the anti-tumour effect of SEQ ID NO:1 in the SCID/beige model is equivalent in extent and kinetics to that obtained in the SCID mouse model. Data from experiments comparing SEQ ID NO:1 to the mismatched and scrambled control ODNs (SEQ ID NOs:2 and 3, respectively) once again demonstrate that the anti-tumour activity is specific to the R2 complementary sequence (FIG. 32B). Given that published reports have demonstrated a requirement for intact NK, T and B cell function for maximal CpG mediated effects, these results suggest that the primary mechanism of action of SEQ ID NO:1 is independent of immune stimulation.

Although these data suggest that CpG-mediated immune stimulation is not a major contributor to the anti-tumour efficacy of SEQ ID NO:1, immune stimulation, in addition to sequence specific anti-tumour activity may not be a negative side effect in immune competent individuals. In fact, mild immune stimulation may off-set immunodeficiency brought about by chemotherapy.

Methylated Oligonucleotide Data

CpG dinucleotide motifs must be unmethylated in order to stimulate immune responses in vertebrates. Therefore, one approach to addressing the question of CpG mediated immune stimulation is to methylate the C residue in the CpG motif, thereby abrogating a CpG mediated immune response (Krieg, A. M. *Annu. Rev. Immunol.* 20:709-760 (2002)).

Figure 33:
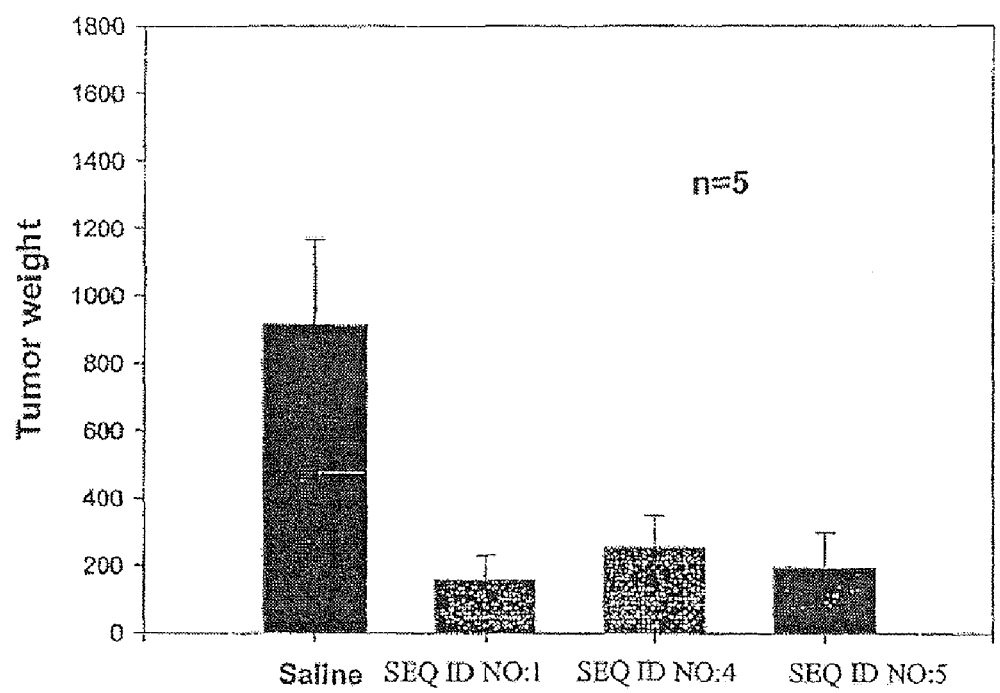
FIG. 33 depicts effects of SEQ ID NOs:1, 4 and 5 on HT29 tumour xenografts in CD-1 nude mice.

For treatment of HT29 tumour xenografts in CD-1 nude mice, methylation at the CpG (C9; SEQ ID NO:4) does not abrogate the anti-tumour activity of SEQ ID NO:1, supporting a mechanism by which SEQ ID NO:1 anti-cancer activity is the result of sequence specific antisense action and not CpG-mediated immune stimulation (FIG. 33). There is a measurable, but not significant, effect on the anti-tumour activity that is also seen with the control oligonucleotide SEQ ID NO:5 (met-11C), suggesting that the methylation itself may affect to a small extent the compound's ability to act via an antisense mechanism, possibly by reducing target binding, oligonucleotide half-life or oligonucleotide-uptake into tumour cells. These results indicate that SEQ ID NO:1 can act independently of any immune stimulatory activity attributable to the CpG.

Example 9

Pharmacokinetics in the Monkey and Rat

Toxicity studies were conducted with SEQ ID NO:1 in order to understand the safety profile of this oligonucleotide. It is informative to note that SEQ ID NO:1 target sequence in R2 mRNA is absolutely conserved across human, rat and monkey, as the sequences were determined by direct sequencing of R2 cDNAs prepared by RT-PCR amplifications of mRNA extracted from rat and monkey cells.

The toxicokinetics and tissue distribution of SEQ ID NO:1 (and related oligonucleotide metabolites obtained from exonuclease-mediated chain shortening) were determined in rats and monkeys. In addition to investigating the pharmacokinetics and tissue distribution of SEQ ID NO:1, the purpose of the studies was to correlate adverse effects in the animal studies to the concentrations of SEQ ID NO:1 (and metabolites) in tissue and blood. A capillary electrophoresis (CE) method was used to measure the concentrations of SEQ ID NO:1 (and metabolites) in plasma and tissues.

9.1 Absorption
Pharmacokinetics in the Rat

In a pharmacokinetic study, groups of male rats were administered one or two bolus i.v. injections (tail vein) of SEQ ID NO:1 at a dose of 50 mg/kg (295 mg/m$^2$) and intravenously infused (abdominal vena cava) for up to 48 h at a dose of 50 mg/kg/day (295 mg/m$^2$/day). Blood samples were collected into EDTA-containing tubes from subsets of animals in each group at various sampling times up to 56 h after initiation of infusion or bolus injection. Parent SEQ ID NO:1 concentrations were measured in plasma by a validated CE method.

Since the plasma concentrations of SEQ ID NO:1 in rats were similar after one and two consecutive daily bolus injections, the pharmacokinetic parameters were calculated after the second bolus injection. Table 6 presents the pharmacokinetic parameters calculated on the basis of the mean levels after bolus injection and after 24-hours continuous intravenous infusion at 50 mg/kg/day. The plasma half-life of SEQ ID NO:1 after bolus injection was 1.36 h. The mean plasma steady state concentration of SEQ ID NO:1 (Css) during infusion was 9.62 μg/mL and the level was achieved at approximately 3 hr after infusion initiation. Plasma clearance (Cl) was calculated to be 154 mL/hr/kg after bolus injection and 216 mL/hr/kg after infusion.

Pharmacokinetics in the Monkey

SEQ ID NO:1 was administered to monkeys by continuous intravenous infusion for 21 days followed by a 21-day recovery period. Twenty-eight monkeys were administered one of the following dose levels; vehicle control, 2, 10, or 50 mg/kg/day (24.6, 123, and 615 mg/m²/day). Toxicokinetic samples were collected prior to the initiation of infusion, approximately 8, 24, 48, and 96 hours following the start of infusion, and on Day 20 prior to the change in dose-syringes.

Plasma concentrations of SEQ ID NO:1 in the 2 mg/kg dose group could not be detected. Plasma concentrations appear to reach steady state by eight hours after dosing. Table 6 presents the pharmacokinetic parameters for the 10 mg/kg and 50 mg/kg dose groups. The median $T_{max}$ were 480 and 24 hours for the 10 mg/kg and the 50 mg/kg dose groups, respectively.

TABLE 6

Mean Pharmacokinetic Parameters in Rats and Monkeys Administered Repeated Doses of SEQ ID NO: 1

| Parameter | Rat SEQ ID NO: 1 Dose (50 mg/kg/day) by | | Monkey SEQ ID NO: 1 Dose in mg/kg/day | |
|---|---|---|---|---|
| | Bolus | Infusion | 2 | 10 | 50 |
| $C_{max}$ (μg/mL) | 679 | — | — | 2.94 | 20.3 |
| $T_{max}$ (hour) | 0.083 | — | — | 325 | 171 |
| $K_{el}$ (1/hour) | 0.5109 | — | — | — | — |
| Css (μg/mL) | — | 9.62 | — | 2.10 ± 0.48 | 16.2 ± 2.2 |
| $T_{1/2}$ (hour) | 1.36 | — | — | — | — |
| AUC(0-t) (μg*hr/mL) | 637 | — | — | — | — |
| AUC(0-24) (μg*hr/mL) | 369 | 208 | — | — | — |
| AUC(0-inf) (μg*hr/mL) | 650 | — | — | — | — |
| Cl (mL/hr/kg) | 154 | 216 | — | 208 ± 52 | 130 ± 16 |

9.2 Distribution

The concentrations of SEQ ID NO:1 (and related n+1, n−1 to n−15 oligonucleotide metabolites) in the following rat and monkey tissues were measured by a validated CE method (Southwest Bio-Labs, Inc.): kidney, liver, spleen, heart, lung, bone marrow (rat), lymph nodes (monkey) and brain tissues. The tissue samples were collected from the designated animals as described in the 21-day toxicity studies: rats, administered bolus intravenous injections of SEQ ID NO:1 every other day at 2, 10, or 50 mg/kg; and monkeys administered SEQ ID NO:1 by continuous intravenous infusion at 2, 10, or 50 mg/kg/day.

The results indicated that the tissue biodistribution of SEQ ID NO:1 in the rat and monkey was similar to that reported for other phosphorothioate oligonucleotides. In both species, the highest concentrations of SEQ ID NO:1 were observed in the kidney>liver>bone marrow>spleen>heart>lung. SEQ ID NO:1 concentrations in the brain were below the limits of detection in both species (lower limits for detection is 1 μg/g in the rat and 0.2 μg/g in the monkey; see Tables 7a and 6b).

Whereas evidence of metabolites was observed in all of the assessed tissues, the highest concentrations were observed in the kidney and liver, organs known to be critical to metabolism and the primary route of elimination for phosphorothioate oligonucleotides. The organs with the highest concentrations of parent oligonucleotide and metabolites are also the ones demonstrating histopathological abnormalities. The results suggested that there was a relationship between the concentration of SEQ ID NO:1 (and its metabolites) in the tissues with morphological and functional changes found in those tissues such as elevated transaminases, increased creatinine, or decreased platelet counts.

Upon discontinuation of dosing with SEQ ID NO:1, there was evidence that both the parent compound and its metabolites decrease over time. Specifically, these studies in rat and monkey, provides evidence of reversibility of the observed effects on the sampled tissues after a 21-day recovery period.

TABLE 7a

Extraction of SEQ ID NO: 1 and metabolites (n + 1 through n − 13) from Rat and Monkey Tissues with Analysis by Capillary Electrophoresis

| | | Mean Concentration (μg/g) SEQ ID NO: 1 at: | | | | |
|---|---|---|---|---|---|---|
| Tissue | Dose (mg/kg/day) | 4 hrs | 48 hrs | 4 hrs | Necropsy Day 22 | Necropsy Day 43 |
| | | RAT | | Monkey | | |
| Liver | 2 | 6.9 | BDL | 13.8 | 137.8 | ND |
| | 10 | 19.7 | 4.7 | 38.1 | 129.0 | ND |
| | 50 | 51.9 | 19.8 | 91.6 | 316.6 | 0.9 |
| Kidney | 2 | 6.7 | 1.0 | 28.0 | 176.2 | ND |
| | 10 | 31.1 | 13.3 | 129.5 | 246.5 | ND |
| | 50 | 86.1 | 48.2 | 286.6 | 1425.2 | 1.6 |
| Heart | 2 | 0.8 | BDL | BDL | BDL | ND |
| | 10 | 1.5 | BDL | BDL | 1.9 | ND |
| | 50 | 14.5 | 2.5 | 20.8 | 46.3 | 0.5 |
| Lung | 2 | BDL | BDL | 0.9 | BDL | ND |
| | 10 | 1.6 | BDL | 2.1 | 1.6 | ND |
| | 50 | 13.3 | 2.1 | 18.2 | 39.2 | BDL |
| Spleen | 2 | 1.0 | BDL | 1.8 | 17.8 | ND |
| | 10 | 2.6 | BDL | 3.2 | 82.1 | ND |
| | 50 | 32.7 | 1.4 | 18.4 | 260.6 | 57.2 |
| Brain | 2 | BDL | BDL | BDL | BDL | ND |
| | 10 | BDL | BDL | BDL | BDL | ND |
| | 50 | BDL | BDL | BDL | BDL | BDL |
| Bone Marrow/ Lymph node* | 2 | BDL | BDL | 1.8 | 2.2 | ND |
| | 10 | 2.7 | BDL | 3.6 | 13.1 | ND |
| | 50 | 13.2 | 2.8 | 29.9 | 253.5 | 59.9 |

[a]Post first dose
[b]Post last dose
BDL: below detectable limits (1 μg/g rat; 0.2 μg/g monkey)
*bone marrow in the rat; lymph node in the monkey
ND: Not Determined TABLE 7b Extraction of SEQ ID NO: 1 and metabolites (n + 1 through n − 13) from Rat and Monkey Tissues with Analysis by Capillary Electrophoresis

| | | Mean Concentration (μg/g) total metabolites (n + 1 through n − 13) at: | | | | |
|---|---|---|---|---|---|---|
| Tissue | Dose (mg/kg/day) | 4 hrs[a] | 48 hrs[a] | 4 hrs[b] | Necropsy Day 22 | Necropsy Day 43 |
| | | Rat | | Monkey | | |
| Liver | 2 | 16.9 | BDL | 42.1 | 425.7 | ND |
| | 10 | 47.9 | 8.3 | 105.9 | 486.2 | ND |
| | 50 | 79.9 | 68.7 | 279.7 | 806.6 | 2.3 |
| Kidney | 2 | 20.8 | 3.6 | 122.8 | 605.8 | ND |
| | 10 | 88.1 | 68.4 | 613.5 | 886.1 | ND |
| | 50 | 187 | 287.6 | 1373.6 | 3230.8 | 10.5 |
| Heart | 2 | 0.3 | BDL | BDL | BDL | ND |
| | 10 | 4.2 | BDL | 9.4 | 4.6 | ND |
| | 50 | 13.0 | 7.2 | 42.5 | 113.8 | 3.5 |
| Lung | 2 | BDL | BDL | 0.2 | BDL | ND |
| | 10 | 2.3 | BDL | 3.3 | 4.2 | ND |
| | 50 | 21.8 | 3.8 | 30.0 | 124.0 | BDL |
| Spleen | 2 | 1.2 | BDL | 6.5 | 71.4 | ND |
| | 10 | 7.8 | BDL | 13.5 | 198.3 | ND |
| | 50 | 19.9 | 2.2 | 60.8 | 1097 | 367.8 |

TABLE 7b-continued

Extraction of SEQ ID NO: 1 and metabolites (n + 1 through n − 13) from Rat and Monkey Tissues with Analysis by Capillary Electrophoresis

| Tissue | Dose (mg/kg/day) | Mean Concentration (µg/g) total metabolites (n + 1 through n − 13) at: | | | | |
|---|---|---|---|---|---|---|
| | | 4 hrs[a] | 48 hrs[a] | 4 hrs[b] | Necropsy Day 22 | Necropsy Day 43 |
| | | Rat | | Monkey | | |
| Brain | 2 | BDL | BDL | BDL | BDL | ND |
| | 10 | BDL | BDL | BDL | BDL | ND |
| | 50 | BDL | BDL | BDL | BDL | BDL |
| Bone Marrow/ Lymph node* | 2 | BDL | BDL | 3.8 | 21.0 | ND |
| | 10 | 3.5 | BDL | 6.6 | 86.2 | ND |
| | 50 | 19.5 | 4.4 | 67.4 | 801.2 | 371.3 |

[a]Post first dose
[b]Post last dose
BDL: below detectable limits (1 µg/g rat; 0.2 µg/g monkey)
*bone marrow in the rat; lymph node in the monkey
ND: Not Determined Example 10

Toxicology in Monkey and Rat 10.1 Single Dose Toxicity
Acute Intravenous Toxicity Study of in the Monkey Intravenous infusion of SEQ ID NO:1 for 24 hours at doses up to 80 mg/kg/day (984 mg/m$^2$/day) was well-tolerated by rhesus monkeys. There were no deaths during the study. No treatment-related clinical signs or changes in body weight, blood pressure, heart rate, serum biochemistry or haematology parameters were observed at any dose. Mild treatment-related changes in APTT were observed at the end of infusion at 40 mg/kg/day (492 mg/m$^2$/day) and 80 mg/kg/day (984 mg/m$^2$/day), and slight treatment-related increases in complement split product Bb were observed at the end of infusion at 20, 40, and 80 mg/kg/day (246, 492, and 984 mg/m$^2$/day). These effects indicate an apparent inhibition of the intrinsic coagulation pathway, and modest activation of the alternative complement pathway, respectively. These treatment-related changes were typical class effects of phosphorothioate oligonucleotide administration.

10.2 Repeat Dose Toxicity
21-Day Intravenous Toxicity Study in the Rat with a 21-Day Recovery SEQ ID NO:1 was administered to Sprague-Dawley rats via intravenous bolus injection every second day up to 21 days, with a 21-day recovery period. The study design included 4 treatment groups; vehicle controls, 2 mg/kg, 10 mg/kg, and 50 mg/kg. The main study group consisted of 10 animals/sex, and an additional 5 animals/sex were included in the control and high-dose groups for a recovery phase. Satellite animals (6/sex/group) were also included for toxicokinetic analysis.

A single mortality resulted from the 50 mg/kg dose as well as various adverse clinical signs, a decrement in body weight gain (associated with diminished food consumption), lymphocytosis, moderate anemia and thrombocytopenia, and various relatively mild changes in serum chemistry parameters. At the 10 mg/kg dose level, there were no clinical signs, no effects on body weight or food consumption, a lesser degree of anemia and thrombocytopenia, and only minor changes in a few serum chemistry parameters. The 2 mg/kg/dose level had no remarkable effects on any of the above parameters. Histopathological findings indicated the lymphoid system, kidneys, and liver as target organs at 10 and 50 mg/kg, with evidence of recovery at the highest dose level. Again, these findings were consistent with the known toxicity profile of phosphorothioates.

21-Day Continuous Infusion Toxicity Study of SEQ ID NO: 1 in the Monkey with a 3-Week Recovery A second repeat-dose study was conducted in monkeys to evaluate the toxicity associated with administration of test article by continuous intravenous infusion for 21 days followed by a 21-day recovery period. Twenty-eight monkeys were administered one of the following dose levels; vehicle control, 2 mg/kg/day, 10 mg/kg/day, or 50 mg/kg/day. Toxicokinetic samples were collected prior to the initiation of infusion, approximately 8, 24, 48, and 96 hours following the start of infusion, and on Day 20 prior to the change in dose-syringes. No unplanned deaths occurred during the study. Effects seen at the 10 and 50 mg/kg/day dose levels included splenic histiocytosis, anticoagulant effects, complement activation, and continuous infusion effects such as formation of thrombi and vascular damage, inflammation in the lungs and leakage at the infusion site. Target organs were clearly identified through histopathologic changes as kidneys, liver, and lymph nodes. In general, the SEQ ID NO: 1-related changes were dose-dependent in severity and/or incidence, and were reversed either completely or partially (with the suggestion of eventual complete recovery) during the 3-week post-dosing treatment-free period. As in the previous rat study, the 2 mg/kg/day dose level was identified as the no-adverse-effect-level (NOAEL).

Intravenous Compatibility Assay

SEQ ID NO: 1 injection was tested for its potential to cause haemolytic activity based on cell lysis and haemoglobin release in human whole blood and did not cause haemolysis under static or dynamic conditions.

Example 11

Clinical Trials Using SEQ ID NO:1 in Combination with Various Chemotherapeutics

Examples of potential designs for clinical trials to test SEQ ID NO:1 in combination with various known chemotherapeutics are provided in Table 8.

Examples of ongoing clinical trials and other clinical trials that have been approved by the NCI using SEQ ID NO: 1 are outlined below. Details of the protocols involved for each of trials 2-7 are provided in Table 9. Trial 1 (renal carcinoma is described in more detail in Examples 12 and 13.

1. PROTOCOL LO1-1409 (RENAL CELL CARCINOMA)
Study Description:
SEQ ID NO: 1 and capecitabine combination therapy in patients with advanced or metastatic renal cell carcinoma (Phase I/II)
Population: Advanced or metastatic renal cell carcinoma having failed standard therapy
Study regimen: SEQ ID NO: 1 (CIV infusion)+capecitabine cycles: 14 days+7 days rest
Phase I/II
Status: Ongoing in Phase II
Dosing: SEQ ID NO: 1 was administered as a continuous intravenous infusion for 21 days at a starting dose of 148.0 mg/m$^2$/day in combination with capecitabine administered orally at a fixed dose of 1660 mg/m$^2$/day (divided into two daily doses for 21 days) followed by 7 days of rest.

2. PROTOCOL L6093 (BREAST)
Study Description
A Phase I Study of SEQ ID NO: 1 and Capecitabine in the treatment of Metastatic Breast Cancer
Population: Breast cancer, metastatic and failing 2 or more prior regimens Study regimen; SEQ ID NO: 1+Capecitabine 14 days in 21 day cycle
Subjects: 40 (2 Stages: 20 ea)
Phase II
Status: Design under review 3. PROTOCOL L6104 (NSCLC)
Study Description
A Phase I/II Trial of SEQ ID NO: 1 and Docetaxel in Metastatic or Advanced Non-Small Cell Lung Cancer
Population: Metastatic or unresectable locally advanced NSCLC
Study regimen SEQ ID NO: 1+Docetaxel
Subjects: 42 (12 Phase I; 30 Phase II)

4. PROTOCOL L6090 (SOLID TUMOURS)
Study Description
A Phase I Study of SEQ ID NO: 1 and Gemcitabine in Patients with Solid Tumours
Population: Solid tumours metastatic or unresectable and for which curative or palliative measures do not exist or are no longer effective.
Study regimen SEQ ID NO:1+Gemcitabine
Subjects: 34

5. PROTOCOL L6108 (AML)
Study Description
A Phase I Trial of SEQ ID NO:1 in combination with high-dose cytarabine in refractory or relapsed acute myeloid leukaemia (AML)
Population: Acute myeloid leukaemia refractory or relapsed.
Study regimen SEQ ID NO:1+cytarabine
Subjects: 30

6. PROTOCOL L6099 (COLORECTAL)
Study Description
A Phase I Trial of SEQ ID NO: 1, Oxaliplatin and Capecitabine in Refractory Unresectable Colorectal Cancer
Population: Locally advanced or metastatic colorectal cancer (refractory, unresectable). Patients must have had at least one standard prior chemotherapy with no prior oxaliplatin-containing regimen.
Study regimen SEQ ID NO: 1+oxaliplatin & capecitabine
Subjects: 15-20
Phase I
Status: Design under review 7. PROTOCOL L6102 (PROSTATE)
Study Description
A Phase II Study of SEQ ID NO: 1 and Docetaxel in Patients with Hormone-Refractory Prostate Cancer
Population: Patients with hormone-refractory prostate cancer and rising PSA levels (PSA$\geq$20). ECOG 0-2, with adequate organ function
Study regimen SEQ ID NO: 1+Docetaxel
Subjects: 40
Phase II
Status: awaiting Phase II dose from ongoing trial.

TABLE 8

Examples of Clinical Trials designed for Antisense Oligonucleotide SEQ ID NO: 1 in Combination with Various Chemotherapeutic Agents*

| Disease | Performance Status (PS) and Organ Function | Prior Therapy | Trial Design Schedule |
| --- | --- | --- | --- |
| Solid tumours | PS $\geq$ 2<br>Must have adequate hematologic, renal, and metabolic function | No limit stated<br>$\geq$4 wks since prior RT<br>$\geq$3 wks since prior therapy (6 wks for nitrosourea or mitomycin C) | SEQ ID NO: 1:<br>CIV day 1-21<br>148-185 mg/m$^2$/day<br>Capecitabine:<br>PO BID day 1-21<br>500-1500 mg<br>28-day cycle |
| Solid tumours | PS 0-2<br>Creatinine: <2.0 mg/dL<br>SGOT: <2 x normal<br>Bilirubin: <1.5 mg/dL<br>WBC: >4000<br>PLT: >100,000 | No limit stated<br>$\geq$4 wks since prior tx | SEQ ID NO: 1:<br>CIV day 1-21<br>100-185 mg/m$^2$/day<br>Capecitabine:<br>PO BID day 1-21<br>1100-2000 mg/m$^2$/day<br>28-day cycle |
| Breast | PS 60-100%<br>Must have adequate hematologic, renal, and hepatic function | $\geq$2 prior regimens<br>No prior capecitabine or 5-FU unless in adjuvant setting | SEQ ID NO: 1:<br>CIV day 1-21<br>74-185 mg/m$^2$/day<br>Capecitabine:<br>PO BID day 8-21<br>600-1000 mg/m$^2$<br>28-day cycle |
| Colorectal | PS 0-2<br>bilirubin $\leq$ 1.5 x ULN<br>SGOT/SGPT $\leq$ 3 x ULN | 1 prior CT or adjuvant | SEQ ID NO: 1:<br>CIV day 1-21<br>185 mg/m$^2$/day<br>Capecitabine:<br>PO BID day 1-14<br>start at 850 mg/m$^2$<br>28-day cycle |
| Colorectal | PS 60-100%<br>Must have adequate hematologic, renal, and hepatic function | No prior oxaliplatin | SEQ ID NO: 1:<br>CIV day 1-21<br>74-185 mg/m$^2$/day<br>Capecitabine:<br>PO BID d2-15<br>600-1000 mg/m$^2$ |

TABLE 8-continued

Examples of Clinical Trials designed for Antisense Oligonucleotide
SEQ ID NO: 1 in Combination with Various Chemotherapeutic Agents*

| Disease | Performance Status (PS) and Organ Function | Prior Therapy | Trial Design Schedule |
|---|---|---|---|
| Solid tumours | PS 0-2<br>Abnormal organ function permitted | ≧1 prior regimens<br>No prior docetaxel | Oxaliplatin:<br>IV day 2<br>130 mg/m$^2$/day<br>28-day cycle<br>SEQ ID NO: 1:<br>CIV day 1-21<br>50-185 mg/m$^2$/day<br>Docetaxel:<br>IV weekly x 3<br>30-35 mg/m$^2$<br>28-day cycle |
| Solid tumours | PS 0-1<br>Abnormal organ function not permitted | No restrictions | SEQ ID NO: 1:<br>CIV day 1-21<br>148-185 mg/m$^2$/day<br>Docetaxel:<br>IV day 1, 8, 15<br>30-35 mg/m$^2$<br>28-day cycle |
| NSCLC & other solid tumours | PS 0-1<br>Abnormal organ function not permitted | ≦2 prior CT | SEQ ID NO: 1:<br>CIV day 1-22<br>1-5 mg/kg/day<br>Docetaxel:<br>IV day 8, 15, 22<br>35 mg/m$^2$<br>28-day cycle |
| NSCLC | PS 0-2<br>Must have adequate hematological, renal, & hepatic function | Prior platinum-based CT required<br>No prior taxane CT<br>>1 systemic tx not permitted<br>≧28 days since prior surgery or RT | SEQ ID NO: 1:<br>CIV day 1-14<br>74-185 mg/m$^2$/day<br>Docetaxel:<br>IV day 3 1st cycle,<br>day 1 2nd cycle<br>60-75 mg/m$^2$/day<br>21-day cycle |
| Prostate | PS 0-2<br>Abnormal organ function not permitted | No prior CT<br>Must have failed front-line hormonal treatment | SEQ ID NO: 1:<br>CIV day 1-21<br>3-5 mg/kg/day<br>Docetaxel:<br>IV day 1, 8, 15<br>30-36 mg/m$^2$/day<br>28-day cycle |
| Genitourinary | PS 0-2<br>creatinine 2X ULN,<br>liver function <1.5 ULN | 3 prior CT | SEQ ID NO: 1:<br>CIV day 1-21<br>100-185 mg/m$^2$/day<br>Docetaxel:<br>IV<br>40-80 mg/m$^2$ every 3 wks |
| Solid tumours | PS 0-2<br>Abnormal organ function not permitted | ≦2 prior tx | Schedule A:<br>SEQ ID NO: 1:<br>CIV day 1-21<br>90-190, RP2D<br>mg/m$^2$/day<br>Gemcitabine:<br>IV day 1, 8, 15<br>1000-1200 mg/m$^2$<br>Schedule B:<br>SEQ ID NO: 1:<br>CIV day 1-21 (RP2D)<br>Gemcitabine:<br>CIV day 1-21<br>750-1200 mg/m$^2$<br>28-day cycles |
| Solid tumours | PS 0-2<br>Abnormal organ function not permitted | No restrictions | SEQ ID NO: 1:<br>CIV day 2-21 cycle 1<br>(100-185 mg/m$^2$)<br>CIV day 1-21 for subsequent cycles<br>Gemcitabine:<br>IV day 1, 8, 15<br>400-1000 mg/m$^2$<br>28-day cycle |
| Colon cancer | PS ≧ 60%<br>survival ≧ 3 mo<br>Must have adequate | Must have progressed following 5-FU, irinotecan, & oxaliplatin CT | SEQ ID NO: 1:<br>CIV day 1-21<br>85-185 mg/m$^2$/day |

TABLE 8-continued

Examples of Clinical Trials designed for Antisense Oligonucleotide
SEQ ID NO: 1 in Combination with Various Chemotherapeutic Agents*

| Disease | Performance Status (PS) and Organ Function | Prior Therapy | Trial Design Schedule |
|---|---|---|---|
| | hematologic, renal, and hepatic function | | Gemcitabine: IV day 1, 8 every 6 wks 1000 mg/m$^2$ Capecitabine: PO BID d1-14 every 3 wks 650 mg/m$^2$ |
| NSCLC | PS > 60% survival > 3 mo Must have adequate hematologic, renal, and hepatic function | No prior gemcitabine or SEQ ID NO: 1 ≧4 wks since prior CT ≧6 wks since prior mitomycin C CT ≧2 wks since prior RT | SEQ ID NO: 1: CIV day 1-21 74-185 mg/m$^2$/day Gemcitabine: IV day 2, 9, 16 800-1000 mg/m$^2$ 28-day cycle |
| Renal cell carcinoma | PS 0-2 Must have adequate hematologic, renal, and hepatic function | Phase 1 No prior gemcitabine CT Phase 2 ≦2 prior tx allowed ≧4 wks since prior RT, surgery, or tx | SEQ ID NO: 1: CIV day 1-21 111-185 mg/m$^2$/day Gemcitabine: IV weekly x 3 800-1000 mg/m$^2$ 28-day cycle |
| Breast cancer | PS 60-100% Must have adequate hematologic, renal, and hepatic function | ≦1 prior tx no prior platinum or gemcitabine allowed | SEQ ID NO: 1: CIV day 1-21 74-185 mg/m$^2$/day Gemcitabine: IV day 2, 9 600-1000 mg/m$^2$/day Oxaliplatin: IV day 2 130 mg/m$^2$/day 28-day cycle |
| AML | PS 0-2 Abnormal organ function permitted: Cr ≦ 2.0 mg/dL total bilirubin <2.0 mg/dL AST/ALT < 5 x ULN | Prior therapy O.K. | SEQ ID NO: 1: CIV day 1-21 120-280 mg/m$^2$/day Idarubicin: IV day x3 12 mg/m$^2$/day |
| AML | PS 0-2 Abnormal organ function permitted: Cr ≦ 2.0 mg/dL total bilirubin ≦2.0 mg/dL | Prior therapy O.K. | SEQ ID NO: 1: CIV day 1-21 120-280 mg/m$^2$/day Ara-C: IV day x4 1 g/m$^2$/day |
| AML, CML | PS 0-2 Cr < 2 bilirubin < 2 | At least 1 prior therapy | SEQ ID NO: 1: CIV day 1-5 2-10 mg/kg/day Ara-C: IV day 1-5 1 g/m$^2$/day |
| AML | PS ECOG 0-2 Abnormal organ function not permitted | Chemotx, including auto or allo SCT | SEQ ID NO: 1: CIV day 1-8 3.5, 5 mg/kg/day Mitoxantrone: IV day 4-8 6 mg/m$^2$/day Etoposide: IV day 4-8 80 mg/m$^2$/day Ara-C: IV day 4-8 500-1000 mg/m$^2$/day |
| CML | PS 0-2 Abnormal organ function permitted: Cr ≦ 2.0 mg/dL total bilirubin <2.0 mg/dL AST/ALT < 5 x ULN | Imatinib mesylate failed | SEQ ID NO: 1: CIV day 1-21 120-280 mg/m$^2$/day Fludarabine: IV day 3-7 30 mg/m$^2$/day Ara-C: IV day 3-7 2 g/m$^2$/day Filgrastim: |

TABLE 8-continued

Examples of Clinical Trials designed for Antisense Oligonucleotide
SEQ ID NO: 1 in Combination with Various Chemotherapeutic Agents*

| Disease | Performance Status (PS) and Organ Function | Prior Therapy | Trial Design Schedule |
|---|---|---|---|
| Metastatic cancer | ECOG ≦ 2<br>Must have adequate hematologic, renal, and hepatic function | ≧4 wks since prior RT<br>Phase 1: unlimited chemotherapy<br>Phase 2: must have prior paclitaxel and carboplatin | 5 mcg/kg/day, start day 8<br>SEQ ID NO: 1:<br>CIV day 1-14<br>125-185 mg/m$^2$/day<br>Carboplatin:<br>AUC = 5, 6<br>Paclitaxel:<br>IV weekly<br>135-175 mg/m$^2$<br>Cycles repeat every 21 days |
| Head & Neck, esophagus, lung | PS 0-2<br>Abnormal organ function not permitted | One prior multimodality tx permitted (including platinum-based) | SEQ ID NO: 1:<br>CIV day 1-21 (dose TBD)<br>Cisplatin:<br>IV weekly<br>15-40 mg/m$^2$<br>28-day cycle |
| SCLC | PS 0-2<br>Abnormal organ function not permitted | No prior chemotx | SEQ ID NO: 1:<br>CIV day 1-21<br>3-5 mg/kg/day<br>Cisplatin:<br>IV day 1<br>50-60 mg/m$^2$/day<br>Irinotecan:<br>IV day 1, 8, 15<br>50-60 mg/m$^2$/day |
| Pancreatic adenocarc | PS 0-2<br>Abnormal organ function not permitted | Prior gemcitabine required<br>≧4 wks since gemcitabine regimen<br>No prior irinotecan allowed | SEQ ID NO: 1:<br>CIV day 1-14<br>104-185 mg/m$^2$/day<br>Irinotecan:<br>IV day 1, 8<br>75-125 mg/m$^2$/day<br>21-day cycle |
| Pancreas, gall bladder, & biliary ducts | PS 0-2<br>Total bilirubin <3X ULN eligible | 1 prior tx: either gemcitabine or bryo/Taxol | SEQ ID NO: 1:<br>CIV day 1-21 (dose TBD)<br>5-FU:<br>CIV day 1-21<br>100-225 mg/m$^2$/day<br>28-day cycle |
| Pancreas cancer | PS = ≧60%<br>AGC > 1,500/mcL<br>Hgb ≧ 9 mg/dL<br>plts > 100,000/mcL<br>creat ≦ 1.5 ULN<br>bilirubin ≦ 1.5 ULN<br>ALP/SGOT/SGPT ≧ 3 x iULN | Must have PD after previous gemcitabine chemotx for metastatic pancreatic cancer | SEQ ID NO: 1:<br>CIV day 1-21<br>85-185 mg/m$^2$/day<br>Oxaliplatin:<br>IV day 1<br>130 mg/m$^2$/day<br>Capecitabine:<br>PO BID d1-14<br>1000 mg/m$^2$/day<br>Cycles repeat every 21 days<br>Schedule modified if significant toxicity in 2/3 patients @ dose level 1:<br>SEQ ID NO: 1:<br>CIV day 1-14<br>85-185 mg/m$^2$/day<br>Oxaliplatin and capecitabine: as above<br>Cycles repeat every 21 days |
| Prostate cancer | PS ≦ 2<br>ANC ≧ 1.5 x 10e9/L<br>plts ≧ 100 x 10e9/L<br>creat ≦ 2 x ULN or<br>CrCl ≧ 40 mL/min<br>bili ≦ 1.5 x ULN | Hormone-refractory;<br>no prior chemotx;<br>≧4 wks since prior XRT | SEQ ID NO: 1:<br>CIV day 1-14<br>111-185 mg/m$^2$/day<br>Mitoxantrone:<br>IV every 3 weeks<br>12 mg/m$^2$ |

TABLE 8-continued

Examples of Clinical Trials designed for Antisense Oligonucleotide SEQ ID NO: 1 in Combination with Various Chemotherapeutic Agents*

| Disease | Performance Status (PS) and Organ Function | Prior Therapy | Trial Design Schedule |
|---|---|---|---|
| | AST/ALT $\leq$ 3xULN<br>LVEF $\geq$ 50% | | Prednisone:<br>PO BID<br>5 mg<br>Cycles repeat every 21 days to 10 cycles or PD |

*Abbreviations are as follows:
AGC: Absolute granulocyte count
Allo SCT: Allogenic stem cell transplantation
Auto SCT: Autologous stem cell transplantation
ALP: Alkaline phosphatase
ALT: Alanine aminotransferase
ANC: Absolute neutrophil count
AST: Aspartate aminotransferase
Bili: bilirubin
CIV: Continuous intravenous infusion
Cr and Creat: Creatinine
CT: Computerized axial tomography
Hgb: Haemoglobin
LVEF: Left ventricular ejection fraction
PLT and plts: Platelet count
PO BID: By mouth, 2 times a day
RT: Radiotherapy
Rx: Therapy
SGOT: Serum glutamic-oxalacetic transferase
SGPT: Serum glutamic pyruvic transaminase
Tx: Treatment
ULN: Upper limit of normal
WBC: White blood cell/white blood count

TABLE 9

NCI Approved Clinical Trial Protocols

| Protocol | Objectives | Drug Regimen |
|---|---|---|
| 2. (L6093) | To evaluate the response rate and response duration<br>To evaluate the toxicity<br>To determine pharmacokinetic data<br>To investigate potential markers of RNR inhibition and fluoropyrimidine metabolism. | SEQ ID NO: 1 (148-185 mg/m2/day) + Capecitabine (600-1000 mg/m2 bid for 14 days). 28 day treatment cycle. SEQ ID NO: 1 will be administered as a 21-day continuous IV infusion on days 1-21 with a starting dose of 74 mg/m2/day. The starting dose of capecitabine will be 600 mg/m2 orally bid on days 8-21. Patients will have one week rest and then resume cycle two on day 29. |
| 3. (L6104) | To determine the recommended Phase II dose<br>To assess the objective tumour response rate<br>To assess the toxicity, stable disease rate, time to disease progression, objective response duration and duration of stable disease.<br>To investigate PK parameters<br>To measure the baseline and post-treatment levels of RNR activity | SEQ ID NO: 1 (3-5 mg/kg/day) + Docetaxel (60-75 mg/m2 IV) SEQ ID NO: 1 continuous IV infusion day 1 to 14 every 21 days Docetaxel IV day 3 in cycle 1, day 1 subsequent cycles, every 21 days |
| 4. (L6090) | Primary<br>To determine the toxicity profile and MTD<br>Secondary<br>To examine PK and PD<br>To determine the effects on RNR R2 subunit mRNA and | SEQ ID NO: 1 (100-185 mg/m2/day) + Gemcitabine (400-1000 mg/m2) In Cycle 1, the SEQ ID NO: 1 CIV is given from day 2-16 every 28 days. Only from cycle 2 onwards, SEQ ID NO: 1 CIV is |

TABLE 9-continued

NCI Approved Clinical Trial Protocols

| Protocol | Objectives | Drug Regimen |
|---|---|---|
| | protein expression<br>To examine the effects on apoptotic markers and cell cycle regulatory proteins and to analyze the serum biomarkers | given from day 1-15 every 28 days.<br>For all cycles, gemcitabine is given weekly on days 1, 8, and 15 every 28 days. |
| 5. (L6108) | To determine the MTD<br>To document therapeutic responses<br>To evaluate PK<br>To measure R2 mRNA<br>To assess apoptosis in leukemic cells<br>To measure RNR enzymatic activity | Cohort 1<br>SEQ ID NO: 1 (3.5-5 mg/kg/day) + Cytarabine (2000-3000 mg/m2 q12 hours)<br>SEQ ID NO: 1 will be administered by continuous IV infusion for a total of 168 days (days 1 to 7).<br>Cytarabine will be administered IV over 2 hours every 12 hours for a total of 12 doses (day 2 to 7)<br>Cohort 2<br>SEQ ID NO: 1 (3.5-5 mg/kg/day) + Cytarabine (1500-2000 mg/m2 q12 hours)<br>SEQ ID NO: 1 will be administered by continuous IV infusion for a total of 144 hours (days 1 to 6).<br>Cytarabine will be administered IV over 4 hours every day for 5 days (days 2 to 6) for a total of 5 doses. |
| 6. (L6099) | Primary<br>To establish maximum tolerated dose<br>To describe the toxicities at each dose level studied.<br>Secondary<br>To evaluate the pharmacokinetics of the combination therapies.<br>To evaluate levels of ribonucleotide reductase - M2 subunit (RR-M2) mRNA levels.<br>To quantify changes in dCTIP levels in peripheral mononuclear cells as surrogate marker of RR inhibition. | SEQ ID NO: 1 (3-5 mg/kg/day) + Oxaliplatin (130 mg/m2) & Capecitabine (600-1200 mg/m2/ BID)<br>The dose of oxaliplatin will be fixed at 130 mg/m2 and administered IV over 2 hours on day 2 of a 21 day treatment cycles. After the first cycle, oxaliplatin will be given on day 1.<br>The starting dose of capecitabine will be 600 mg/m2 twice orally and will be given beginning on day 2 of the first cycle for 28 doses and subsequently on day 1 after initiation of SEQ ID NO: 1.<br>SEQ ID NO: 1 will be given as a continuous infusion through a central line over 14 days beginning on day 1 of treatment. |
| 7. (L6102) | Primary<br>To establish the efficacy using PSA-response rate<br>Secondary<br>To estimate objective tumour response<br>To estimate the median time to progression<br>To investigate safety and tolerability<br>To estimate the median of duration of PSA-response<br>To measure baseline and post-treatment levels of RNR activity | SEQ ID NO: 1 + Docetaxel (Dose to be determined)<br>SEQ ID NO: 1: Continuous IV infusion for 14 days of a 21-day cycle to start with a docetaxel bolus.<br>Docetaxel: Administered IV every 21 days. For cycle 1 only administered on day 3.<br>Prednisone: 5 mg po bid continuously |

Example 12

Phase I Study of SEQ ID NO:1 Given by Continuous Intravenous Infusion (CVI) in Patients with Advanced Cancer Eligibility Criteria
  Histologically confirmed diagnosis of solid tumour or lymphoma for which no effective therapy is available
  Measurable or evaluable disease
  Age=18y; KPS=70%; Informed consent
  No other cancer treatment within 28 days prior to study (42 days for nitrosourea or mitomycin)
  Adequate organ function; INR and aPTT WNL
  No requirement for aspirin, NSAIDs or anticoagulation
  No pregnancy, lactation or bleeding diathesis
Trial Design
  Open label, single centre, dose escalation
  First phase escalation: cohorts of 1-3 patients; dose doubling until Grade 2 toxicity or dose of 148 mg/m² is completed
  Any toxicity equivalent to Grade 2 requires entry of 3 patients and switch to second phase escalation
  Second phase escalation: At least 3 patients/cohort; dose escalation of 20-30% until DLT
Treatment Plan
  SEQ ID NO:1 administered as 21 day CVI in 250 mL saline via CADD pump followed by one week rest
  Starting dose: 18.5 mg/m² (⅙ the dose producing minimal and reversible toxicity in monkeys)
  Tumour re-assessment after every 2 cycles in absence of DLT or rapid tumour progression
DLT Definition
  Grade 4 ANC lasting=3 days or associated with fever
  Grade 4 platelets or grade 3 platelets with grade 1 or higher hemorrhage
  Grade 3 or higher coagulopathy with grade 1 or higher hemorrhage
  Nausea, vomiting or diarrhea=Grade 3 despite maximal supportive care
  Any other non-heme tox.=Grade 3
  DLT based on cycle 1 events
MTD Definition
  The dose level at which at least one-third of the patients experience DLT
  Recommended phase II dose is one level below MTD
Pharmacokinetic and Pharmacodynamic Sampling On Day 1 a heparinized blood sample was collected at baseline and then at 1, 2, 3, 4 and 6 hours after start of infusion. On Days 8 and 15, a single heparinized sample was taken. On Day 22 a heparinized blood sample was collected prior to the end of infusion and at 0.25, 0.5, 1, 2, 4 and 6 hours following the end of infusion. Plasma was decanted and stored at −70° C.

| Patient characteristics | |
|---|---|
| Characteristic | No. of Patients |
| Patients enrolled | 36 |
| Men | 25 |
| Women | 11 |
| Median Age, y (range) | 60 (29-78) |
| Karnovsky Performance Status (KPS) | |
| 100 | 7 |
| 90 | 12 |
| 80 | 13 |
| 70 | 4 |

| Patient characteristics | |
|---|---|
| Characteristic | No. of Patients |
| Prior Therapy | |
| Chemotherapy/Immunotherapy | 36 |
| Chemotherapy and Radiation | 10 |
| Diagnosis | |
| Kidney | 15 |
| Colorectal | 9 |
| Mesothelioma | 3 |
| Pancreatic | 2 |
| Unknown Primary | 2 |
| Hepatoma | 2 |
| Other | 3 |

| Dose Levels | | |
|---|---|---|
| SEQ ID NO: 1 (mg/m²/day) | No. of assessable patients | No. of cycles |
| 18.5 | 2 | 5 |
| 37 | 1 | 2 |
| 74 | 1 | 2 |
| 148 | 6 | 11 |
| 185 | 9 | 14 |
| 222 | 7 | 16 |

Figure 34:
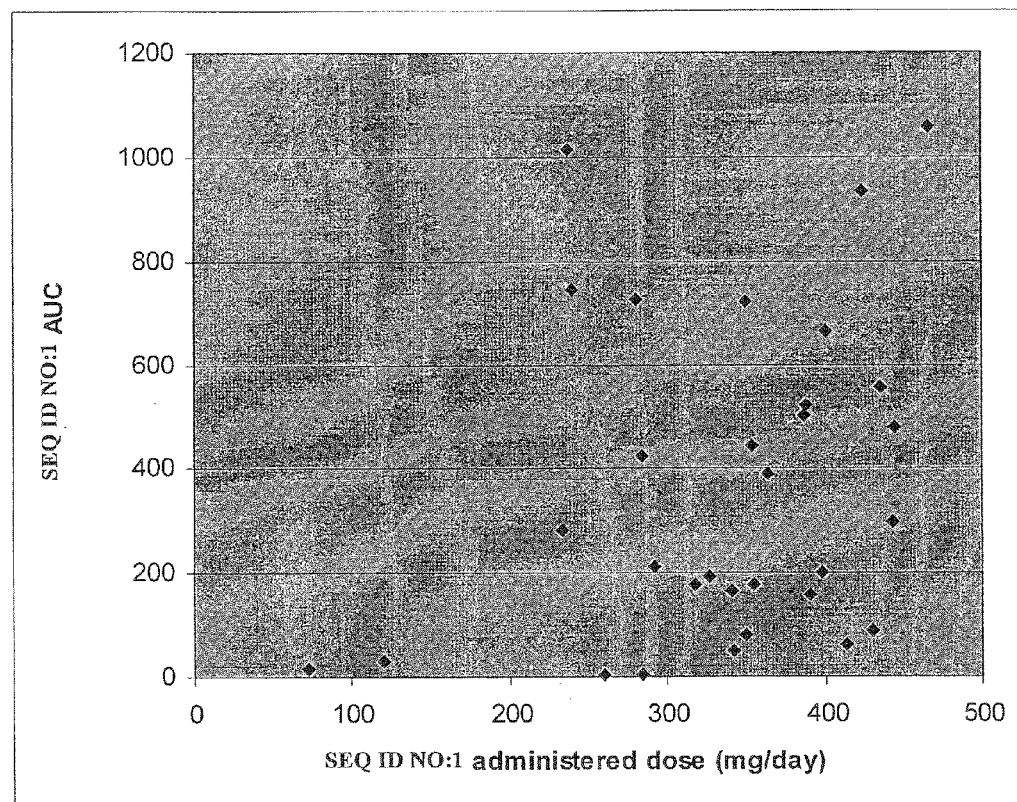
FIG. 34 presents the results from Phase I clinical trials for SEQ ID NO:1, (A) depicts the AUC vs. Actual Dose plot for SEQ ID NO:1, and (B) depicts the plasma concentration of SEQ ID NO:1 vs. time.
Figure 34:
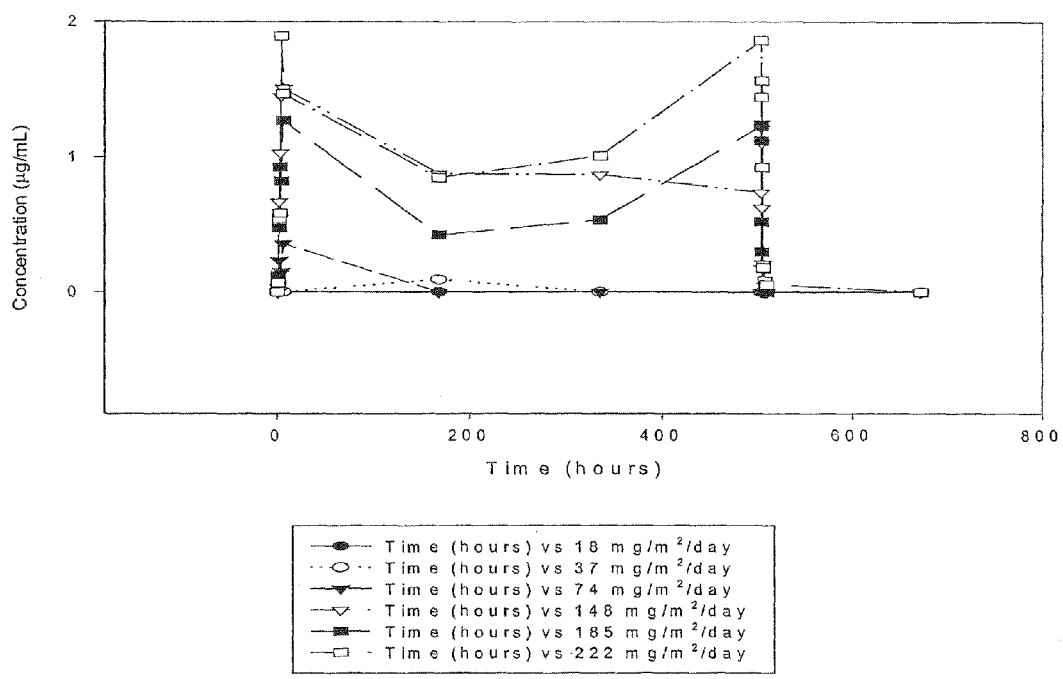

This study was conducted to determine the dose-limiting toxicity (DLT) and maximum tolerated dose (MTD) of SEQ ID NO:1 in patients with advanced malignancies. Pharmacokinetic parameters were assessed. SEQ ID NO:1 was administered using a portable infusion pump in cycles of 21 days CVI followed by one week of rest. The starting dose was 18.5 mg/m²/day, corresponding to ¹/₁₀ and ⅙ the dose that produced minimal toxicity in rodents and monkeys, respectively. Doses were doubled in cohorts of 1-3 patients until the appearance of Gr 1 toxicity, with subsequent escalation of 20-30% in cohorts of 3 patients. DLT was defined as Gr 4 neutropenia lasting 3 days or with fever; Gr 4 thrombocytopenia (T) or Gr 3 T with Gr 1 bleeding; or Gr 3 non-hematologic toxicity. Thirty-six patients [25 males, median age: 60 (29-78), median KPS 90 (70-100); 15 renal cell, 9 colorectal cancer and 12 other] received 49 cycles of therapy at doses ranging from 18.5 to 222 mg/m²/day (6 levels). Three DLTs were observed in 25 patients assessable for toxicity: Gr 3 fatigue at 148 mg/m²/day (1/6 patients), Gr 4 transaminase elevation (2/6 patients) at 222 mg/m²/day (MTD); other serious toxicities were: Gr 3 non-neutropenic infection (2 patients) and bowel obstruction (1 patient). Hematologic toxicity was mild; common (Gr 1-2) non-hematologic toxicities were: fatigue (69%), anorexia (42%), and nausea (38%). Four patients had stable disease (SD) after 2 cycles. SEQ ID NO:1 was well tolerated by 11 patients at the recommended phase II dose of 185 mg/m²/day. Preliminary analysis of the pharmacokinetic (PK) parameters suggests a $t_{1/2}$ of about 2 hrs and mean steady-state plasma concentration of 0.6 µg/ml at the phase II dose. Results are summarised in Tables 10-12 (below) and FIGS. 34A & B.

TABLE 10

Cycle 1 Toxicity

| Dose Level SEQ ID NO: 1 (mg/m²/day) | No. of Patients | Fatigue 1 | 2 | 3 | Anorexia 1 | 2 | Neutropenia 2 | 3 | 4 | Anemia 1 | 2 | 3 | DLT |
|---|---|---|---|---|---|---|---|---|---|---|---|---|---|
| 18.5 | 2 | 1 | | | 1 | | | | | | | | |
| 37 | 1 | | | | | | | | | | | | |
| 74 | 1 | 1 | | | 1 | | | | | | | | |
| 148 | 6 | 1 | 1 | 1* | 1 | 1 | | 1 | | | | | 1 |
| 185 | 9 | 3 | 2 | | 2 | | | | | | | | |
| 222 | 7 | 3 | 1 | | | 1 | 1 | | | | 2 | | |

*DLT

TABLE 11

Cycle 1 Toxicity

| Dose Level SEQ ID NO: 1 (mg/m²/day) | No. of Patients | Transaminases 2 | 3 | 4 | Bilirubin 2 | 3 | 4 | Rash 1 | 2 | 3 | Nausea 1 | 2 | DLT |
|---|---|---|---|---|---|---|---|---|---|---|---|---|---|
| 18.5 | 2 | | | | | | | | | | | | |
| 37 | 1 | | | | | | | | | | | | |
| 74 | 1 | | | | | | | | | | 1 | | |
| 148 | 6 | | | | | | | | | | | 1 | |
| 185 | 9 | | | | | | | | | 3 | | | |
| 222 | 7 | 1 | | 2* | 1 | | 1* | | 1 | 3 | | | 2 |

*DLT

TABLE 12

Pharmacokinetics -- Summary*

| Dose Level (mg/m²/day) | AUC (μg·hr/ml) | $C_{ss}$ (μg/ml) | $C_{max}$ (μg/ml) | $T_{1/2}$ (hr) | Clearance (L/m²/day) |
|---|---|---|---|---|---|
| 37 | 7.54 (141)$ (2)** | 0.03 (141) (2) | 0.09 (141) (2) | N/A | 595 (1) |
| 74 | 15.5 (141) (2) | N/A (1) | 0.61 (141) (2) | N/A | N/A |
| 148 | 426 (87) (8) | 0.77 (94) (8) | 2.2 (41) (8) | 0.79 (25) (4) | 244 (90) (6) |
| 185 | 340 (67) (11) | 0.63 (98) (11) | 2.15 (57) (11) | 2.74 (171) (7) | 558 (119) (9) |
| 222 | 380 (94) (11) | 1.24 (87) (10) | 2.98 (99) (11) | 1.43 (46) (3) | 483 (161) (9) |

*Reported values represent mean values for each parameter
**Number of samples available for analysis of the parameter
N/A: Parameters not available due to missing samples or values below level of detection
$Coefficient of variation for each measured parameter Example 13

Phase I/II Study of SEQ ID NO:1 and Capecitabine Combination Therapy in Patients with Advanced or Metastatic Renal Cell Carcinoma Status:
  Of 31 patients entered in the study to date, 29 patients received study drug (SEQ ID NO:1), 2 patients were withdrawn prior to receiving study drug.
  One patient is ongoing on study treatment.
Population Studied:
  Advanced or metastatic renal cell carcinoma.
Enrolment Status:
  Phase I dose escalation (N=9)
  Phase II: (N=20)
Methodology:
  Open-label, non-randomized
  The Phase I portion escalated the dose of SEQ ID NO:1 in combination with a fixed dose of capecitabine in order to develop the recommended dose for the Phase II portion.
  A Simon two-stage design was utilized for the Phase II portion with a target activity level of 25% and a lower activity level of 10% and scheduled first assessment after 18 patients are evaluable for efficacy in the Phase II portion.

Objectives
Primary:
To determine the recommended phase II dose of SEQ ID NO:1 when given in combination with capecitabine in this patient population
To determine the response rate of SEQ ID NO:1 plus capecitabine in this patient population.
Secondary:
To assess the toxicity of SEQ ID NO:1 plus capecitabine in this patient population
Pharmacokinetic:
To characterize the pharmacokinetic profile of SEQ ID NO:1 and capecitabine in this patient population
Dose Regimens Studied
SEQ ID NO:1-148 mg/m$^2$/day (N=5 patients dosed) combined with capecitabine 1,660 or 1,250 or 850 mg/m$^2$/day (and dose reduction of capecitabine to 1,250 or 850 mg/m$^2$, if necessary)
SEQ ID NO:1-185 mg/m$^2$/day (N=28) combined with capecitabine 1,660 mg/m$^2$/day (and dose reduction of capecitabine to 1,250 or 850 mg/m$^2$, if necessary)
Note: 2 patients increased dose of SEQ ID NO:1 and 4 patients decreased dose of capecitabine
Route of Administration:
SEQ ID NO:1—continuous intravenous infusion for the first 21 days in each 28 day cycle
Capecitabine—given orally in two divided doses daily for the first 21 days in each 28 day cycle
Study medication was given as second, third, or fourth line therapy, and, for patients for whom standard therapy is not suitable, as first line therapy.
Recommended Phase II Dose Determination
SEQ ID NO:1 mg/m$^2$/day combined with capecitabine 1,660 mg/m$^2$/day was identified as the safe combination dose for Phase II based on Phase I safety data in 9 patients including 6 at this recommended Phase II dose.
Interim Evaluation Status
Preliminary evaluability assessment was performed to determine whether sufficient data were available for the scheduled efficacy assessment required per protocol. Taking Phase I and Phase II together, data have been collected to date on 21 patients evaluable for tumour assessment on combination SEQ ID NO:1 and capecitabine of 29 evaluable for drug safety/toxicity. One patient is still ongoing after more than 8 months of therapy.

The majority of patients had failed two or more prior therapies before entering the study, exhibited extensive metastases and were representative of a population with very poor prognostic outcome in renal cell cancer. Treatment has been well tolerated with few treatment-related toxicities other than those already known to occur with these drugs with acceptable frequency.

Preliminary unaudited data showed that more than half of the 21 patients with evaluable tumour assessments exhibited disease stabilization (10 patients) or partial response (1 patient) with stable disease duration ranging up to more than eight months. Persistent tumour shrinkages of index tumours compared to baseline measurements were observed in two patients who to date have had up to 23% and 40% reductions respectively in tumour sum longest diameters. A full assessment of tumour responses will be done only following completion of the patient accrual required for evaluation of the Phase II efficacy data, which is the primary efficacy assessment specified in protocol.

Adverse Events and Safety
Adverse Events
All adverse events for this study are subjected to a translation procedure using the MedDRA dictionary. All of the treated patients have experienced at least one adverse event. Adverse events occurred most frequently in the following classes: gastrointestinal disorders; general disorders and administration site conditions; metabolism and nutrition disorders; blood and lymphatic system disorders; nervous system disorders; skin and subcutaneous tissue disorders; musculoskeletal and connective tissue disorders; respiratory, thoracic and mediastinal disorders; infections and infestations; investigations; and psychiatric disorders. Adverse events in other classes were experienced by less than 25% of the patients.
Serious Adverse Events
To date, serious adverse events have been reported for 13 patients enrolled this study. The events were considered to be unrelated or unlikely to be related to protocol therapy for 6 patients, and possibly, probably or definitely related for 7 patients.
Reason for Completion/Withdrawal Phase I
The nine patients enrolled in the Phase I component were removed from the study. Eight patients were removed as a result of progressive disease and one patient refused further treatment after seven cycles. One patient received only one cycle of protocol therapy before removal from the study due to progressive disease. Three patients received two cycles of protocol therapy. Five patients went on to receive more than two cycles: one patient received three cycles, two patients received four cycles, and three patients received seven cycles of treatment. Two patients required dose reductions in study therapy. No other Phase I patients required dose reductions in study therapy.
Reason for Completion/Withdrawal Phase I
Nineteen patients enrolled and treated in the Phase II component were removed from the study to date. Ten patients were removed as a result of progressive disease, six patients were removed because of patient refusal on request, two patients were removed due to serious adverse events and one patient died while on-study. One patient remains on-study.

Ten patients discontinued treatment after two cycles. Two patients received four cycles of study treatment before removal from the study due to progressive disease. One patient received four cycles of study treatment before removal from the study due to SAEs (Grade 3 catheter-related infection, Grade 3 platelet transfusion and Grade 4 cardiovascular pulmonary embolism, all possibly related to study therapy). One patient went off-study after two cycles due to progressive disease, and one patient discontinued after six cycles with progressive disease. Three patients received one cycle of study therapy before going off-study. One patient was taken off study due to a Grade 3 thrombotic event which required anticoagulation, and was considered inevaluable for efficacy. One patient was taken off study due to the development of neurologic symptoms requiring radiation therapy and one patient died on-study of respiratory failure secondary to pulmonary metastases from renal cell carcinoma, accompanied by acute renal failure secondary to renal cell carcinoma. One additional patient remains on-study and is receiving treatment. The patient has received seven cycles of therapy and has begun Cycle 8. One patient required a 25% reduction in the dose of capecitabine due to elevations in ALT and AST.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are as follows:

1. A method of treating acute myeloid leukemia in a human patient comprising administering to said patient an antisense oligonucleotide consisting of the sequence as set forth in SEQ ID NO:1 at a dose of between about 3 mg/kg/day and about 5 mg/kg/day, in combination with cytarabine.

2. The method according to claim 1, wherein said antisense oligonucleotide is a modified or substituted oligonucleotide.

3. The method according to claim 1, wherein said antisense oligonucleotide is a phosphorothioated oligonucleotide.

4. The method according to claim 1, wherein said antisense oligonucleotide is administered to said patient at a dose of about 3.5 mg/kg/day.

5. The method according to claim 1, wherein said antisense oligonucleotide is administered to said patient at a dose of about 5 mg/kg/day.

6. The method according to claim 1, wherein said antisense oligonucleotide is administered systemically.

7. The method according to claim 1, wherein said antisense oligonucleotide is administered intravenously.

8. The method according to claim 7, wherein said antisense oligonucleotide is administered by continuous intravenous infusion.

9. The method according to claim 1, wherein said cytarabine is administered to said patient at a dose of between about 1500 mg/m$^2$/12 hours and 3000 mg/m$^2$/12 hours.

10. The method according to claim 1, wherein said cytarabine is administered to said patient at a dose of between about 1500 mg/m$^2$/12 hours and 2000 mg/m$^2$/12 hours.

11. The method according to claim 1, wherein said cytarabine is administered to said patient at a dose of between about 2000 mg/m$^2$/12 hours and 3000 mg/m$^2$/12 hours.

12. The method according to claim 1, wherein said cytarabine is administered intravenously.

13. The method according to claim 1, wherein said antisense oligonucleotide is administered prior to said cytarabine.

14. The method according to claim 1, wherein said antisense oligonucleotide is administered concurrently with said cytarabine.

15. The method according to claim 1, wherein said antisense oligonucleotide is administered after said cytarabine.

16. The method according to claim 1, where said acute myeloid leukemia is a refractory acute myeloid leukemia.

17. The method according to claim 1, where said acute myeloid leukemia is a relapsed acute myeloid leukemia.

18. The method according to claim 1, wherein said patient has undergone prior chemotherapy.

19. The method according to claim 1, wherein said patient has undergone prior autologous or allogeneic stem cell transplantation.

* * * * *